United States Patent
Duhaylongsod

(12) 
(10) Patent No.: US 6,711,436 B1
(45) Date of Patent: *Mar. 23, 2004

(54) COMPOSITIONS, APPARATUS AND METHODS FOR FACILITATING SURGICAL PROCEDURES

(75) Inventor: Francis G. Duhaylongsod, Honolulu, HI (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/406,333

(22) Filed: Sep. 27, 1999

Related U.S. Application Data

(63) Continuation-in-part of application No. 09/131,075, filed on Aug. 7, 1998, now Pat. No. 6,060,454.
(60) Provisional application No. 60/055,127, filed on Aug. 8, 1997.

(51) Int. Cl.[7] .............................. A61N 1/18; A61N 1/20; A61N 1/22; A61N 1/24; A61N 1/26

(52) U.S. Cl. .............................. 607/9; 607/10; 607/11; 607/16; 607/27; 607/28; 607/30; 600/16; 600/17; 600/18; 604/507; 604/508; 604/509; 604/510; 604/96; 604/272; 604/523; 604/532

(58) Field of Search .................................. 607/9, 10, 11, 607/16, 27, 28, 30; 600/16, 17, 18; 604/507, 508, 509, 510, 96, 272, 523, 532

(56) References Cited

U.S. PATENT DOCUMENTS

| | | |
|---|---|---|
| 3,241,556 A | 3/1966 | Zacouto |
| 3,640,269 A | 2/1972 | Delgado |
| 3,797,485 A | 3/1974 | Urquart |
| 4,162,679 A | 7/1979 | Reenstierna |
| 4,166,470 A | 9/1979 | Neumann |
| 4,230,119 A | 10/1980 | Blum |
| 4,248,214 A | 2/1981 | Hannah et al. |

(List continued on next page.)

FOREIGN PATENT DOCUMENTS

| | | |
|---|---|---|
| EP | 0 525 475 A2 | 2/1993 |
| EP | 0 528 776 A1 | 2/1993 |
| EP | 0 403 578 B1 | 10/1994 |
| EP | 0 664 104 A2 | 7/1995 |
| EP | 0 783 902 A2 | 7/1997 |
| EP | 0 791 332 A1 | 8/1997 |
| SU | 1731184 | 5/1992 |

(List continued on next page.)

OTHER PUBLICATIONS

"MIDCAB Technique" *Cardiac Surgery Renaissance*, The Advisory Board Company, Washington, D.C., pp. 108–111 (Jun. 1996).

Acuff, T.E. et al., "Minimally invasive coronary artery bypass grafting" *Ann. Thorac. Surg.* 61:135–137 (1996).

Addetia et al., "Perfusion in cardioplegia: an experimental study" *Canadian J. Surg.* 23(2):146–150 (1980).

Agnarsson et al., "Carbachol depolarizes and accelerates pacemaker activity in the sinoatrial node of chicks treated with pertussis toxin" *J. Pharmacol. Exp. Ther.* 247(1):150–155 (1988).

American Hospital Formulary Service, "Miotics" *AHFS Drug Information* 52(20): 2167–2176 (1997).

Avis, K.E. "Parenteral Preparations," Chapter 87, 19th edition *In Remington: The Science and Practice of Pharmacy.* A.R. Gennaro ed., Mack Publishing Company: Easton, Pennsylvania, vol. 2, pp. 1524–1548 (1995).

Bachelard et al., "Regional haemodynamic effects of carbachol injected into the hypothalamic paraventricular nuclei of conscious, unrestrained rats" *Neuropharmacology* 33(6):769–788 (1994).

Backman et al., "Different properties of the bradycardia produced by neostigmine and edrophonium in the cat" *Can. J. Anaesth.* 43(7):731–740 (1996).

(List continued on next page.)

Primary Examiner—Frederick Krass
(74) Attorney, Agent, or Firm—Morrison & Foerster LLP

(57) ABSTRACT

Methods are provided for conducting diagnostic or therapeutic medical or surgical procedures in a patient wherein, during the procedure, autonomous ventricular electrical conductivity and escape beats are reversibly and transiently suppressed to facilitate the procedure. Also provided are compositions which are capable of inducing ventricular asystole in a patient. The compositions may include an atrioventricular (AV) node blocker. In one embodiment, compositions including an AV node blocker and a β-blocker are provided, wherein the β-blocker is present in an amount sufficient to substantially reduce the amount of AV node blocker required to induce ventricular asystole in the patient. The compositions and methods may be used for inducing temporary ventricular asystole in a beating heart, and to facilitate the performance of a variety of techniques, including minimally invasive microsurgical techniques. Methods for performing a diagnostic or therapeutic procedure on a human patient are provided wherein a composition capable of inducing transient reversible ventricular asystole is administered to the heart, for example by intracoronary injection. In one embodiment, the heart then is electrically paced using an electrical pacing system, thereby to maintain the patient's blood circulation. The electrical pacing then is selectively intermittently stopped to allow ventricular asystole to occur, and the steps of the diagnostic or therapeutic procedure, such as suturing, are conducted during the time that the electrical pacing is intermittently stopped. In one embodiment, pacing is not required, and at least one step of a procedure is conducted during a period of ventricular asystole. The methods and compositions advantageously may be used in a range of different diagnostic or therapeutic procedures including imaging procedures, placement of stents, grafts, and embolic devices, and cardiac, vascular and neurosurgical procedures.

45 Claims, 19 Drawing Sheets

U.S. PATENT DOCUMENTS

| | | | |
|---|---|---|---|
| 4,309,776 A | 1/1982 | Berguer | |
| 4,377,704 A | 3/1983 | Gero et al. | |
| 4,404,971 A | 9/1983 | LeVeen et al. | |
| 4,445,892 A | 5/1984 | Hussein et al. | |
| 4,562,596 A | 1/1986 | Kornberg | |
| 4,573,966 A | 3/1986 | Weikl et al. | |
| 4,581,017 A | 4/1986 | Sahota | |
| 4,605,399 A | 8/1986 | Weston et al. | |
| 4,633,882 A | 1/1987 | Matsuo et al. | |
| 4,661,509 A | 4/1987 | Gordon et al. | |
| 4,673,563 A | 6/1987 | Berne et al. | |
| 4,726,356 A | 2/1988 | Santilli et al. | |
| 4,736,024 A | 4/1988 | Della Valle et al. | |
| 4,739,768 A | 4/1988 | Engelson | |
| 4,771,777 A | 9/1988 | Horzewski et al. | |
| 4,827,906 A | 5/1989 | Robicsek et al. | |
| 4,829,985 A | 5/1989 | Couetil | |
| 4,857,552 A | 8/1989 | Rosenberg et al. | |
| 4,884,575 A | 12/1989 | Sanders | |
| 4,923,457 A | 5/1990 | Ellingsen | |
| 4,935,004 A | 6/1990 | Cruz | |
| 4,962,095 A | 10/1990 | Grover et al. | |
| 5,025,779 A | 6/1991 | Bugge | |
| 5,083,564 A | 1/1992 | Scherlag | |
| 5,087,243 A | 2/1992 | Avitall | |
| 5,095,903 A | 3/1992 | DeBellis | |
| 5,096,929 A | 3/1992 | Chiesi et al. | |
| 5,116,851 A | 5/1992 | Krapcho et al. | |
| 5,122,136 A | 6/1992 | Guglielmi et al. | |
| 5,124,326 A | 6/1992 | Mutschler et al. | |
| 5,139,789 A | 8/1992 | Baumgarten | |
| 5,152,277 A | 10/1992 | Honda et al. | |
| 5,162,374 A | 11/1992 | Mulieri et al. | |
| 5,176,638 A | 1/1993 | Don Michael | |
| 5,182,102 A | 1/1993 | DeSantis, Jr. et al. | |
| 5,229,127 A | 7/1993 | McKinzie | |
| 5,287,861 A | 2/1994 | Wilk | |
| 5,290,766 A | 3/1994 | Choong | |
| 5,312,344 A | 5/1994 | Grinfeld et al. | |
| 5,320,604 A | 6/1994 | Walker et al. | |
| 5,354,295 A | 10/1994 | Guglielmi et al. | |
| 5,356,427 A | 10/1994 | Miyata et al. | |
| 5,380,316 A | 1/1995 | Aita et al. | |
| 5,389,096 A | 2/1995 | Aita et al. | |
| 5,425,705 A | 6/1995 | Evard et al. | |
| 5,428,039 A | 6/1995 | Cohen | |
| 5,433,700 A | 7/1995 | Peters | |
| 5,442,053 A | 8/1995 | della Valle et al. | |
| 5,443,489 A | 8/1995 | Ben-Haim | |
| 5,452,733 A | 9/1995 | Sterman et al. | |
| 5,455,229 A | 10/1995 | Hahn et al. | |
| 5,458,574 A | 10/1995 | Machold et al. | |
| 5,459,140 A | 10/1995 | Gramer | |
| 5,474,783 A | 12/1995 | Miranda et al. | |
| 5,478,309 A | 12/1995 | Sweezer et al. | |
| 5,489,295 A | 2/1996 | Piplani et al. | |
| 5,506,229 A | 4/1996 | Dow et al. | |
| 5,543,419 A | 8/1996 | Cross et al. | |
| 5,558,644 A | 9/1996 | Boyd et al. | |
| 5,591,195 A | 1/1997 | Taheri et al. | |
| 5,593,428 A | 1/1997 | Jamshidi | |
| 5,634,895 A | 6/1997 | Igo et al. | |
| 5,651,378 A | 7/1997 | Matheny et al. | |
| 5,735,290 A | 4/1998 | Sterman et al. | |
| 5,738,096 A | 4/1998 | Ben-Haim | |
| 5,792,135 A | 8/1998 | Madhani et al. | |
| 5,797,900 A | 8/1998 | Madhani et al. | |
| 5,807,377 A | 9/1998 | Madhani et al. | |
| 5,830,222 A | 11/1998 | Makower | |
| 5,873,366 A | 2/1999 | Chim et al. | |
| 5,893,848 A | 4/1999 | Negus et al. | |
| 5,913,876 A | 6/1999 | Taylor et al. | |
| 6,060,454 A * | 5/2000 | Duhaylongsod | 514/26 |
| 6,087,394 A * | 7/2000 | Duhaylongsod | 514/26 |
| 6,101,412 A * | 8/2000 | Duhaylongsod | 514/26 |
| 6,127,410 A1 * | 1/2001 | Duhaylongsod | 514/26 |

FOREIGN PATENT DOCUMENTS

| | | |
|---|---|---|
| WO | WO 94/18881 | 9/1994 |
| WO | WO 95/08364 | 3/1995 |
| WO | WO 95/10218 | 4/1995 |
| WO | WO 95/15192 | 6/1995 |
| WO | WO 95/15715 | 6/1995 |
| WO | WO 95/21573 | 8/1995 |
| WO | WO 95/35065 | 12/1995 |
| WO | WO 96/00033 | 1/1996 |
| WO | WO 96/05773 | 2/1996 |
| WO | WO 96/21489 | 7/1996 |
| WO | WO 97/25098 | 7/1997 |
| WO | WO 97/40885 | 11/1997 |
| WO | WO 98/10828 | 3/1998 |
| WO | WO 98/10829 | 3/1998 |
| WO | WO 98/10830 | 3/1998 |
| WO | WO 98/10831 | 3/1998 |
| WO | WO 98/10832 | 3/1998 |
| WO | WO 98/16164 | 4/1998 |
| WO | WO 99/03533 | 1/1999 |

OTHER PUBLICATIONS

Backman et al., "Mechanism of the bradycardia produced in the cat by the anticholinesterase neostigmine" *J. Pharmacol. Exp. Ther.* 265(1):194–200 (1993).

Backman et al., "Neostigmine decreases heart rate in heart transplant patients" *Can J. Anaesth.* 43(4):373–378 (1996).

Badeer et al., "Factors affecting pulsus alternans in the rapidly driven heart and papillary muscle" *Am. J. Physiology* 213(5):1095–1101 (1967).

Baker, A.B. et al., "Intentional asystole during endoluminal thoracic aortic surgery without cardiopulmonary bypass" *Br. J. Anaesth.* 78:444–448 (1997).

Beal, "Changes in renal haemodynamics and electrolyte excretion after intraventricular infusion of carbachol in conscious sheep" *Quarterly Journal of Experimental Physiology* 65:159–171 (1980).

Bel et al., "Inhibition of the pacemaker current: a bradycardic therapy for off–pump coronary operations" *Ann. Thorac. Surg.* 66:148–52 (1998).

Belardinelli et al., "Evidence for adenosine mediation of atrioventricular block in the ischemic canine myocardium" *J. Clin. Invest.* 68(1): 195–205 (1981).

Benetti, F.J. and Ballester, C., "Use of thoracoscopy and a minimal thoracotomy, in mammary–coronary bypass to left anterior descending artery, without extracorporeal circulation" *J. Cardiovasc. Surg.* 36(2):159–161 (1995).

Benetti, F.J. et al., "Video assisted coronary bypass surgery" *J. Card. Surg.* 10:620–625 (1995).

Bjork et al., "Coronary angiography during acetylcholine–induced cardiac arrest" *Acta. Soc. Med. Upsal.* 71:253–262 (1966).

Bjork et al., "Coronary angiography during acetylcholine–induced cardiac arrest in patients with angina pectoris" *The J. of Cardiovascular Surgery* 2(1):9–19 (1961).

Broadley, "The release of a coronary vasodilator metabolite from the guinea–pig isolated perfused heart stimulated by catecholamines, histamine and electrical pacing and by exposure to anoxia" *Br. J. Pharmac.* 58:89–100 (1976).

Broadley, K.J. and Rothaul, A.L., "Catecholamine–induced vasodilator metabolite release from guinea–pig hearts is not due to increased myocardial activity" *Pflügers Arch.* 391:147–153 (1981).

Brockman et al., "Experimental open heart surgery employing hypothermia, mecholyl arrest, and carotid perfusion" *Surgery* 43:815–823 (1958).

Buffolo et al., "Coronary artery bypass grafting without cardiopulmonary bypass" *Ann. Thorac. Surg.* 61:63–66 (1996).

Bufkin et al., "Controlled intermittent asystole for nonpump cardiac surgery: Pharmacologic potentiation of vagal–induced asystole" Conference Abstract (Jan. 1998).

Burger et al., "Prevention of urinary retention after general surgery: A controlled trial of carbachol/diazepam versus alfusozine" *J. Am. Coll. Surg* 185:234–236 (1997).

Calafiore, A.M. et al., "Left anterior descending coronary artery grafting via left anterior small thoracotomy without cardiopulmonary bypass" *Ann. Thorac. Surg.* 61:1658–1665 (1996).

Carbachol (definition). Source: http://www.rxmed.com/monographs/carba2.html (Aug. 6, 1997).

Chiba, S. et al., "Differences in chronotropic and dromotropic responses of the SA and AV nodes to adenosine and acetylcholine" *SHORT COMMUNICATIONS Japan J. Pharmacol.* 22: 273–274 (1972).

Chiba et al., "Blocking of acetylcholine–induced fibrillation by use of norepinephrine into the AV node artery" *The Japanese Journal of Physiology* 20:560–570 (1970).

Chiba et al., "Effect of bethanechol, methacholine and carbachol on AV conduction of the dog heart" *Jap. Heart J.* 13(4):347–353 (1972).

Chiba et al., "Interruption of atrial fibrillation by pacemaker shift induced by the selective use of noradrenaline into the A–V node artery" *Tohoku J. exp. Med.* 95:411–413 (1968).

Chinet et al., "Comparison of the dose–response curves obtained by forced oscillation and plethysmography during carbachol inhalation" *Eur. Respir. J.* 1:600–605 (1988).

Cooley, D.A., "Limited access myocardial revascularization" *Tex. Heart Inst. J.* 23(2):81–84 (1996).

Dake, M.D. et al., "Transluminal placement of endovascular stent–grafts for the treatment of descending thoracic aortic aneurysms" *N. Eng. J. Med.* 331:1729–1734 (1994).

Dorros et al., "Andenosine–induced transient cardiac asystole enhances precise deployment of stent–grafts in the thoracic or abdominal aorta" *J. Endovasc. Surg.* 3:270–272 (1996).

Dotter et al., "Coronary arteriography during induced cardiac arrest and aortic occlusion" *AMA Arch. Internal Med.* 104(1):58/720–67/729 (1959).

Ede, M. et al., "Beyond hyperkalemia: β–blocker–induced cardiac arrest for normothermic cardiac operations" *Ann. Thoracic Surg.* 63:721–727 (1997).

Emmerson et al., "The zig–zag tracheal strip" *J. Pharm. Pharmacol.* 31:798 (1979).

Gundry, S.R. et al., "Coronary artery bypass with and without the heart–lung machine: A Case Matched 6 Year Followup" *American Heart Assoc., 69th Scientific Sessions*, Atlanta, GA, p. I–52, Abstract No. 293 (Nov. 10–13, 1996).

Guntheroth et al., "Alternate deletion and potentiation as the cause of pulsus alternans" *Am. Heart J.* 78(5):669–681 (1969).

Guvendik et al., "Oral beta–blockade with hypothermic potassium cardioplegia in cardiac surgery: is there an additive protective effect?" *Thorac. Cardiovasc. Surg.* 34:25–29 (1986).

Hedlund et al., "Effects of prazosin and carbachol in patients with benign prostatic obstruction" *Scand. J. Urol. Nephrol.* 22:19–22 (1988).

Hesselvik et al., "The use of neostigmine to decrease the heart rate in a patient undergoing minimally invasive coronary artery bypass surgery" *J. of Cardiothorac. and Vascular Anesthesis* 11(7):883–884 (1997).

Hua et al., "Alpha$_{1A}$– and alpha$_{1B}$—adrenoreceptor–mediated positive chronotropic effects on isolation rat atrium" *Acta Pharmacologica Sinica* 14(4):317–319 (1993).

Kanter et al., "Beneficial effects of adding propranolol to multidose potassium cardioplegia" *Circulation* 64(2 Pt 2):II84–II90 (1981).

Khanna, R. and Cullen, H.C., "Coronary artery surgery with induced temporary asystole and intermittent ventricular pacing: An experimental study" *Cardiovasc. Surg.* 4(2):231–236 (1996).

Kihara et al., "Abnormal $Ca_1^{2+}$ handling is the primary cause of mechanical alternans: Study in ferret ventricular muscles" *Am. J. Physiol.* 261(6 Pt 2):H1746–H1755 (1991).

Koglin et al., "Antiadrenergic effect of carbachol but not of adenosine on contractility in the intact human ventricle in vivo" *J. Am. Coll. Cardiol.* 23(3):678–683 (1994).

Lam et al., "Experiences in the Use of Cardioplegia (Induced Cardiac Arrest) in the Repair of Interventricular Septal Defects" *J. Thoracic Surg.* 34:509–520 (1957).

Lam, C.R. et al., "Acetylcholine–induced asystole. An adjunct in open heart operations with extracorporeal circulation" *Extracorporeal Circulation* (J.G. Allen et al., Eds.), Charles C. Thomas, Springfield, IL, pp. 451–458 (1958).

Lam, C.R. et al., "Clinical experiences with induced cardiac arrest during intracardiac surgical procedures" *Ann. Surg.* 146:439–449 (1957).

Lam, C.R. et al., "Induced cardiac arrest (cardioplegia) in open heart surgical procedures" *Surgery* 43:7–13 (1958).

Lam, C.R. et al., "Induced cardiac arrest for intracardiac surgical procedures" *J. Thorac. Surg.* 30:620–625 (1955).

Lang et al., "Stimulation of sudomotor axon reflex mechanism by carbachol in healthy subjects and patients suffering from diabetic polyneuropathy" *Acta Neurologica Scandinavica* 91:251–254 (1995).

Larach, D.R. "Cardiovascular Drugs" *The Practice of Cardiac Anesthesia*, F.A. Hensley Jr. and D.E. Martin (eds.), Little, Brown and Company; Cardiology Roundtable interviews, pp. 108–111 (1990).

Lillehei et al., "Clinical experience with retrograde perfusion of the coronary sinus for direct vision aortic valve surgery with observations upon use of elective asystole or temporary coronary ischemia" *Extracorporeal Circulation*, (J.G. Allen et al., Eds.), Charles C. Thomas, Springfield, IL, pp. 466–485 (1958).

Lillehei et al., "The direct vision correction of calcific aortic stenosis by means of a pump–oxygenator and retrograde coronary sinus perfusion" *Diseases of the Chest* 30(2):123–132 (1956).

Lillehei et al., "The surgical treatment of stenotic or regurgitant lesions of the mitral and aortic valves by direct vision utilizing a pump–oxygenator" *J. Thoracic Surg.* 35:154–191 (1958).

Lin et al., "Warm blood cardioplegia (WBC) prevents dysfunction of endothelium–dependent relaxation (EDR) and endothelium–dependent contraction (EDC) of coronary artery after global ischemia & reperfusion (IR)" American Heart Association., *Abstracts From the 69th Scientific Sessions*, New Orleans, LA, Abstract (Nov. 10–13, 1996).

Lytle, B.W., "Minimially invasive cardiac surgery" *J. Thorac. Cardiovasc. Surg. 111*:554–555 (1996).

Martin et al., "Mechanisms of the cardiovascular response to posterior hypothalamic nucleus administration of carbachol" *J. Cardiovasc. Pharmacol. 27*:891–900 (1996).

Matheny et al., "Vagus nerve stimulation as a method to temporarily slow or arrest the heart" *Ann. Thorac. Surg. 63*:S28–9 (1997).

Mondini et al., "Pharmacologic arrest of the heart in experimental animals" *J. Intl. Coll. Surgeons 28*(1):20–29 (1957).

Nayler, W.G. and Robertson, P.G.C., "Mechanical alternans and the staircase phenomenon in dog papillary muscle" *Am. Heart J. 70*(4):494–498 (1965).

Nelson et al., "Discussions" *Extracorporeal Circulation*, Thomas, Charles, C., Springfield, IL, pp. 486–491 (1958).

Noble, R.J. et al., "The demonstration of alternating contractile state in pulsus alternans." *J. Clin. Invest 49*:1166–1177 (1970).

Otorii, T., "Effects of beta–adrenoreceptor blocking agents on the deslanoside–induced arrhythmia and cardiac arrest in guinea pigs" *Japanese Circ. J. 35*:1535–1540 (1971).

Parodi, J.C. et al., "Transfemoral intraluminal graft implantation for abdominal aortic aneurysms" *Ann. Vasc. Surg. 5*:491–499 (1991).

Philp et al., "Drug effects on the voiding cystometrogram: a comparison of oral bethanecol and carbachol" *British Journal of Urology 52*:484–487 (1980).

*Physicians' Desk Reference for Ophthalmology*, Medical Economics Co., Montvale, NJ, 25th edition, pp. 10–11, 221–223 (1997).

*Physicians' Desk Reference*, Medical Economics Co., Montvale, NJ, 50th edition, pp. 2728–2730 (1996).

Pick et al., "Third and fourth operations for myocardial ischemia short–term results and long–term survival" American Heart Assoc., *Abstracts From the 69th Scientific Sessions*, New Orleans, LA, Abstract (Nov. 10–13, 1996).

Porlier et al., "The effects of acetylstrophanthidin on the response of the AV junction to adrenergic stimulation studied in dogs" *American Heart Journal 91*(4):475–483 (1976).

Preusse et al., "Post–ischemic myocardial function after pre–ischemic application of propranolol or verapamil" *J. Cardiovasc. Surg. 25*:158–164 (1984).

Rials et al., "Effects of atropine on the cardiac arrest induced by propranolol and digitoxin in dogs" *J. Electrocardiology 15*(3):277–284 (1982).

Rivetti et al., "Initial experience using an intraluminal shunt during revascularization of the beating heart" *Ann. Thorac. Surg. 63*:1742–1747 (1997).

Robinson et al., "Transient ventricular asystole using adenosine during minimally invasive and open sternotomy coronary artery bypass grafting" *Ann. Thoracic Surg. 63*:S30–S34 (1997).

Ruiz et al., "Effects of carbachol and acetylcholine on intraocular pressure after cataract extraction" *Am. J. Ophthamol. 107*(1):7–10 (1989).

Sangster et al., "Two cases of carbachol intoxication" *Neth J. Med. 22*:27–8 (1979).

Schaff, H.V. et al., "Minimal thoracotomy for coronary artery bypass: value of immediate postprocedure graft angiography" American Heart Assoc., *Abstracts From the 69th Scientific Sessions*, New Orleans, LA, Abstract (Nov. 10–13, 1996).

Schwartz, D.S., "Surgery for Acquired Heart Disease" *J. Thorac. Cardiovasc. Surg. 111*(3):556–566 (1996).

Sealy, W.C. et al., "Potassium, Magnesium, and Neostigmine for Controlled Cardioplegia" *J. Thoracic Surg. 37*:655–659 (1959).

Sergeant et al., "Further studies in induced cardiac arrest using the agent acetylcholine" *The Heart* pp. 254–257. (1980).

Shumacker, "Induced cardiac arrest, coronary perfusion, deep hypothermia, and circulatory arrest" *The Evolution of Cardiac Surgery*, Ch. 32, Indiana University Press, pp. 280–292, 432–437 (1992).

Stevens, J.H. et al., "Port–access coronary artery bypass grafting: A proposed surgical method" *J. Thorac. Cardiovasc. Surg. 111*:567–573 (1996).

Stevens, J.H. et al., "Port–access coronary artery bypass with cardioplegic arrest: Acute and chronic canine studies" *Ann. Thorac. Surg. 62*:435–441 (1996).

Takeda et al., "Effects on atrio–ventricular conduction of alinidine and falipamil injected into the AV node artery of the anesthetized dog", *Arch int. Pharmacodyn. 297*:39–48 (1989).

Takeuchi et al., "Superior myocardial protection with histidine buffered crystalloid cardioplegia versus blood: A clinical trial" American Heart Association., *Abstracts From the 69th Scientific Sessions*, New Orleans, LA, Abstract (Nov. 10–13,1996).

The Royal Pharmaceutical Society, "Evaluated information on the world's drugs and medicines" Martindale: *The Extra Pharmacopoeia*, 31st edition, pp 1418–1419 (1996).

Thielmeier, K.A. et al., "Role of adenosine–induced ventricular asystole during minimally invasive CABG: Optimizing the surgical field" *Anesthesiology 85*(3A):A162 Abstract (1996).

Ullyot, D.J., "Look ma, no hands!" *Ann. Thorac. Surg. 61*:10–11 (1996).

USPDI, "Advice for the patient: Drug information in lay language", 17th edition, vol. 2, pp. 442–443 (1997).

USPDI, "Drug information for the health care professional", 17th edition, vol. 1, pp. 712–713 (1997).

Viljoen et al., "Propanolol and cardiac surgery" *The J. of Thoracic and Cardiovascular Surgery 64*(5):826–830 (1972).

von der Burchard et al., "A comparison between drug–induced cardioplegia and hypothermia on myocardial protection during ischemia" *Pflügers Archiv. 382*(suppl):R3 Abstract No. 11 (1979).

von der Burchard et al., "The effect of different kinds of drug–induced cardioplegia on myocardial protection during oxygen lack in normo– and hypothermia" *Arch. Pharmacol. 311*(suppl):R34 Abstract No. 134 (1980).

White, G.H. et al., "A new nonstented balloon–expandable graft for straight or bifurcated endoluminal bypass" *J. Endovasc. Surg. I*:16–24 (1994).

Wohlfart, B., "Analysis of mechanical alternans in rabbit papillary muscle" *Acta Physiol Scand. 115*:405–414 (1982).

Co–Pending application U.S. Ser. No. 09/131,075 filed Aug. 7, 1998 issued as U.S. Pat. No. 6,060,454 on May 9, 2000.

Co–Pending application U.S. Ser. No. 09/469,956 filed Dec. 21, 1999.
Co–Pending application U.S. Ser. No. 09/494,145 filed Jan. 28, 2000.
Co–Pending application U.S. Ser. No. 09/379,179 filed Aug. 23, 1999 issued as U.S. Pat. No. 6,087,394 on Jul. 11, 2000.
Co–Pending application U.S. Ser. No. 09/379,381 filed Aug. 23, 1999.

Co–Pending application U.S. Ser. No. 09/379,180 filed Aug. 23, 1999 issued as U.S. Pat. No. 6,043,273 on Mar. 28, 2000.
Co–Pending application U.S. Ser. No. 09/382,705 filed Aug. 23, 1999.
PCT application No. PCT/US98/16469 filed Aug. 7, 1998, Publication No. WO 99/07354, published on Feb. 18, 1999.

* cited by examiner

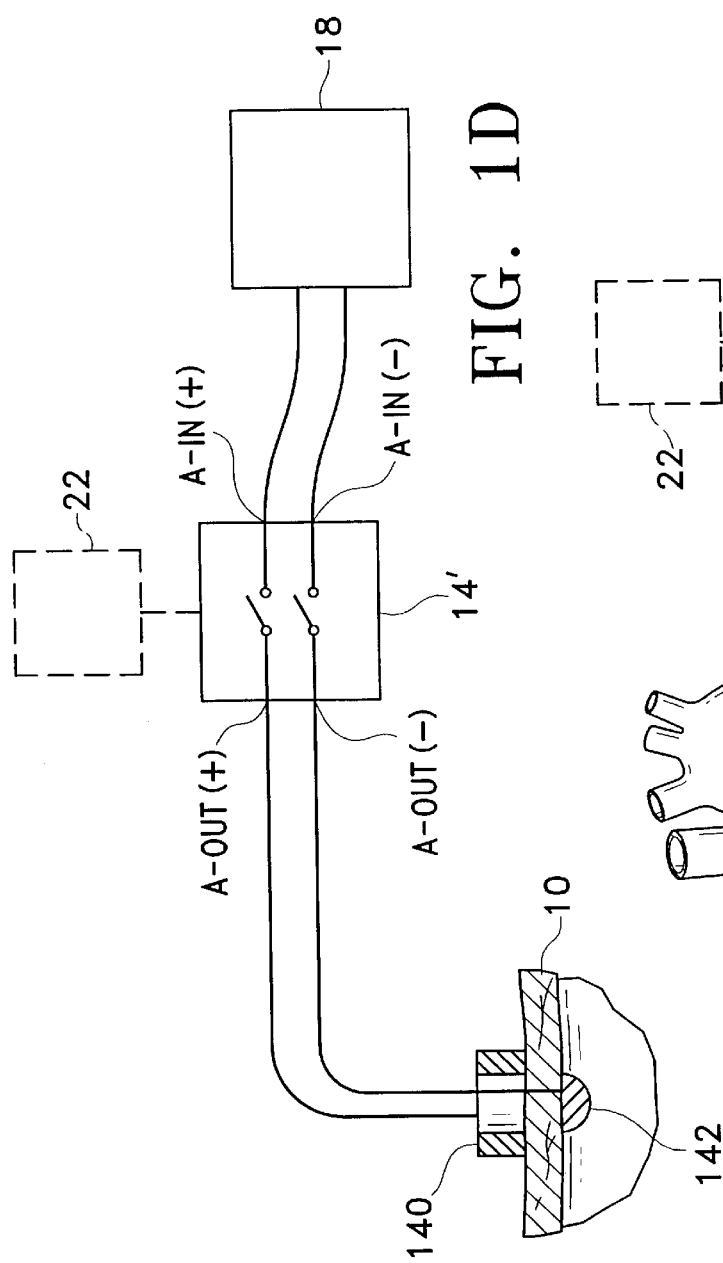
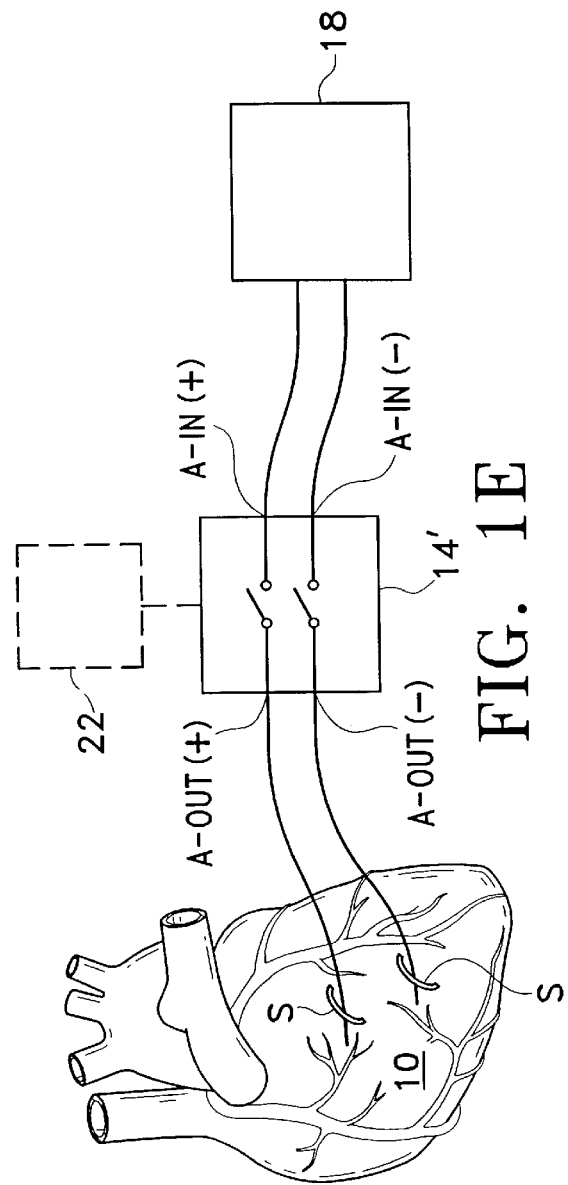
FIG. 1D
FIG. 1E

COMPOSITIONS, APPARATUS AND METHODS FOR FACILITATING SURGICAL PROCEDURES

CROSS REFERENCE TO RELATED APPLICATIONS

This application is a continuation-in-part of U.S. patent application Ser. No. 09/131,075, filed Aug. 7, 1998, now U.S. Pat. No. 6,060,454 which claims the benefit of U.S. Provisional Application Serial No. 60/055,127, filed Aug. 8, 1997, the disclosures of which are incorporated herein by reference.

TECHNICAL FIELD

The present invention relates to compositions, methods, and apparatus that facilitate the performance of diagnostic and therapeutic medical and surgical procedures, such as cardiac surgical procedures, including minimally invasive coronary bypass surgery.

BACKGROUND ART

Heart attacks and angina pectoris (chest pain) are caused by occlusions in the coronary arteries. Atherosclerosis, the major cause of coronary artery occlusions, is characterized by deposits of fatty substances, cholesterol, calcium and fibrin within the arterial wall. As the coronary arteries narrow, blood flow is reduced depriving the heart of much needed oxygen. This occurrence is called myocardial ischemia. Severe and prolonged myocardial ischemia produces irreparable damage to the heart muscle, pronounced cardiac dysfunction, and possibly death. Apart from medical therapy, atherosclerosis is treated with coronary artery bypass graft surgery (CABG), percutaneous transluminal coronary angioplasty (PTCA), stents, atherectomy, and transmyocardial laser revascularization (TMLR).

In patients where PTCA, stents, and atherectomy are unsuitable or unsuccessful, CABG is the procedure of choice. In the conventional CABG operation, a long vertical incision is made in the chest, the sternum is split longitudinally and the halves are spread apart to provide access to the heart. Two large bore tubes, or cannulas, are then inserted directly into the right atrium and the aorta in order to establish cardiopulmonary bypass (CPB). The aorta is occluded with an external clamp placed proximal to the aortic cannula. A third cannula is inserted proximal to the aortic clamp, and is used for the delivery of a cardioplegic solution into the coronary arteries. The hyperkalemic cardioplegic solution protects the heart by stopping atrial and ventricular contraction, thereby reducing its metabolic demand. When the heart is not beating, blood flow to the rest of the body is provided by means of CPB. Cardiopulmonary bypass involves removing deoxygenated blood through the cannula in the right atrium, infusing the blood with oxygen, and then returning it through the cannula in the aorta to the patient. With the heart motionless, the surgeon augments blood flow to the ischemic heart muscle by redirecting blood around the coronary artery occlusion. Although there are several methods to bypass an occlusion, the most important method involves using the left internal thoracic artery (LITA). The LITA normally originates from the left subclavian artery and courses along the anterior chest wall just lateral of the sternum. For this operation, the LITA is mobilized from the chest wall and, with its proximal origin left intact, the distal end is divided and sewn to the coronary artery beyond the site of occlusion (most commonly the left anterior descending coronary artery). After the LITA anastomosis is completed and any further arterial or vein grafts are completed, CPB is weaned as the heart resumes its normal rhythm. The cannulae are removed, temporary pacing wires are sewn to the heart, and plastic tubes are passed through the chest wall and positioned near the heart to drain any residual fluid collection. The two halves of the sternum are approximated using steel wire.

Because the traditional method of performing CABG involves significant operative trauma and morbidity to the patient, attention has been directed to developing less invasive surgical techniques that avoid splitting the sternum. The new techniques are performed with or without CPB through smaller incisions placed between the ribs. One method, called port-access, utilizes groin cannulation to establish CPB, while another, called minimally invasive direct coronary artery bypass or MIDCAB, is performed on the beating heart and therefore does not require CPB. Insofar as these techniques succeed in achieving less operative trauma compared to conventional CABG, postoperative pain is improved, the length of hospitalization is shortened, and the return to normal activity is hastened.

The port-access approach avoids the sternal splitting incision by employing femoral venoarterial CPB and an intraaortic (endoaortic) balloon catheter that functions as an aortic clamp by means of an expandable balloon at its distal end (Daniel S. Schwartz et al. "Minimally Invasive Cardiopulmonary Bypass With Cardioplegic Arrest: A Closed Chest Technique With Equivalent Myocardial Protection." *Journal of Thoracic & Cardiovascular Surgery* 1996; 11 1:556–566. John H. Stevens et al. "Port-Access Coronary Artery Bypass Grafting: A Proposed Method." *Journal of Thoracic & Cardiovascular Surgery* 1996; 111:567–573. John H. Stevens et al. "Port-Access Coronary Artery Bypass With Cardioplegic Arrest: Acute and Chronic Canine Studies." *Annals of Thoracic Surgery* 1996; 62:435–441). This catheter also includes a separate lumen for the delivery of cardioplegic solution and venting of the aortic root. Alternatively, a different catheter may be placed percutaneously into the internal jugular vein and positioned in the coronary sinus for delivery of retrograde cardioplegic solution. Coronary bypass grafting is performed through a separate limited left anterior thoracotomy incision with dissection of the LITA and anastomosis to the atherosclerotic coronary artery under direct vision. Other bypass grafts to coronary arteries can be accomplished using radial artery sewn to the LITA. A description of port-access procedures is found in U.S. Pat. No. 5,452,733, the complete disclosure of which is incorporated herein by reference. Thus, the port-access approach focuses on avoiding the sternal splitting incision while maintaining a motionless heart to facilitate a precise coronary anastomosis as the primary means to reduce operative trauma and morbidity. Compelling evidence to support this contention, however, is scarce. Furthermore, no evidence exists regarding the effectiveness of the coronary anastomosis performed through the limited incision, nor the safety of the intraaortic balloon clamp and the vascular sequelae of groin cannulation. Finally, the port-access approach does not avoid the damaging effects of cardiopulmonary bypass, which include: 1) a systemic inflammatory response; 2) interstitial pulmonary edema; 3) neuropsychological impairment; 4) acute renal insufficiency; and 5) nonmechanical microvascular hemorrhage.

The MIDCAB approach also avoids the sternal splitting incision, favoring instead a limited left anterior thoracotomy incision (Tea E. Acuff et al. "Minimally Invasive Coronary Artery Bypass Grafting." *Annals of Thoracic Surgery* 1996; 61:135–7. Federico J. Benetti and Carlos Ballester, "Use Of Thoracoscopy And A Minimal Thoracotomy, In Mammary-Coronary Bypass To Left Anterior Descending Artery, Without Extracorporeal Circulation." *Journal of Cardiovascular Surgery* 1995; 36:159–61. Federico J. Benetti et al. "Video Assisted Coronary Bypass Surgery." *Journal of Cardiac Surgery* 1995; 10:620–625). Similarly, dissection of the LITA and anastomosis to the coronary artery are then performed under direct vision. The principal difference between the MIDCAB and port-access techniques, however, involves the utilization of cardioplegic solution and CPB (Denton A. Cooley, "Limited Access Myocardial Revascularization" *Texas Heart Institute Journal* 1996; 23:81–84; and Antonio M. Calafiore et al., "Left Anterior Descending Coronary Artery Grafting via Left Anterior Small Thoracotomy without Cardiopulmonary Bypass," *Annals of Thoracic Surgery* 1996; 61:1658–65). Because MIDCAB is performed on the beating heart, cardioplegic solution, aortic cross-clamping and CPB are not required. This approach therefore focuses on the avoidance of cardiopulmonary bypass, aortic cross-clamping and the sternal splitting incision as the primary means to reduce operative trauma and morbidity after conventional CABG.

The potential advantages of MIDCAB compared to conventional CABG include: 1) the avoidance of CPB and aortic cross-clamping; 2) fewer embolic strokes; 3) less blood loss, hence a decreased transfusion requirement; 4) fewer perioperative supraventricular arrhythmias; 5) earlier separation from mechanical ventilatory support; 6) decreased or eliminated intensive care unit stay; 7) shorter length of hospitalization; 8) reduced total convalescence with earlier return to preoperative activity level; and 9) lower overall cost. Despite these potential benefits, however, the durability of the LITA to coronary artery anastomosis is uncertain. At the recent American Heart Association 69th Annual Scientific Session, the Mayo Clinic group reported on 15 patients undergoing MIDCAB. Of these 15 patients, three or 20% required reoperation to revise the anastomosis during the same hospitalization (Hartzell V. Schaff et al., "Minimal Thoracotomy For Coronary Artery Bypass: Value Of Immediate Postprocedure Graft Angiography," Abstract presented at the American Heart Association, 69th Scientific Sessions, Nov. 10–13, 1996, Atlanta, Ga.). Of greater significance, however, was a report from Loma Linda University Medical Center that demonstrated a seven-year LITA to left anterior descending coronary artery patency rate of 42% in a subset of patients who underwent beating heart surgery and presented with recurrent angina. In contrast, the patency rate in an age-, sex- and disease severity-matched control group was 92% (Steven R. Gundry et al., "Coronary Artery Bypass with and Without the Heart-Lung Machine: A Case Matched 6-year Follow-up," Abstract presented at the American Heart Association, 69th Scientific Sessions, Nov. 10–13, 1996, Atlanta, Ga.). Finally, because the MIDCAB approach is restricted mostly to patients with isolated disease of the left anterior descending coronary artery, the vast majority of patients with atherosclerotic heart disease are not appropriate candidates. Thus, despite the potential benefits of MIDCAB, its safety, efficacy, and applicability remain uncertain.

There are major obstacles to precise coronary anastomosis during MIDCAB. The constant translational motion of the heart and bleeding from the opening in the coronary artery hinder precise suture placement in the often tiny coronary vessel. Although bleeding can be reduced by using proximal and distal coronary occluders, by excluding diagonal and septal branches near the arterial opening when possible, and by continuous saline irrigation or humidified carbon dioxide insufflation, the incessant motion of the beating heart remains the Achilles heel of minimally invasive coronary artery bypass.

In summary, although port-access and minimally invasive direct coronary artery bypass techniques avoid the operative trauma and morbidity associated with the sternal splitting incision, both have serious disadvantages. The port-access approach is encumbered by the morbidity of cardiopulmonary bypass and aortic cross-clamping and the cost of the apparatus. Furthermore, the safety of the intraaortic balloon clamp and the vascular sequelae of groin cannulation are unresolved issues. The MIDCAB approach is imperiled by the constant motion of the beating heart which precludes a precise coronary anastomosis. Reports of poor graft patency rates and the need for early reoperation in a significant proportion of patients after MIDCAB attests to the technical difficulty of the procedure.

Conventional CABG requires arrest of the heart through the use of cardioplegic agents, aortic cross-clamping and cardiopulmonary bypass. These cardioplegic agents stop the beating heart to thereby allow precise suture placement and other surgical procedures. A mixture of magnesium sulfate, potassium citrate, and neostigmine has been used to induce cardioplegia during cardiopulmonary bypass. Sealy et al. "Potassium, Magnesium, And Neostigmine For Controlled Cardioplegia: A Report Of Its Use In 34 Patients," *Journal of Thoracic Surgery* 1959, 37:655–59. Although both magnesium and potassium remain integral components of modern cardioplegic solutions, neostigmine was ultimately eliminated. Potassium citrate is currently the most commonly used cardioplegic agent. Potassium impedes excitation-contraction coupling, however, making it impossible to pace the heart by electrical stimulation and necessitating the use of a cardiopulmonary bypass system to sustain the patient. Other chemical agents that have been used in human cardiac operations to slow the rate of ventricular contraction include acetylcholine, neostigmine, adenosine, lignocaine, and esmolol. Another agent, carbachol or carbamyl choline, has been used to induce cardiac arrest in experimental animals. Broadley and Rothaul, *Pflugers Arch.*, 391:147–153 (1981).

Acetylcholine has been used as a cardioplegic agent during cardiopulmonary bypass. Lam et al., "Induced Cardiac Arrest In Intracardiac Procedures, An Experimental Study," *Journal of Thoracic Surgery* 1955; 30:620–25; Lam et al., "Clinical Experiences With Induced Cardiac Arrest During Intracardiac Surgical Procedures," *Annals of Surgery* 1957; 146:439–49; Lam et al., "Induced Cardiac Arrest (Cardioplegia) In Open Heart Procedures," *Surgery* 1958; 43:7–13; and Lam et al., "Acetylcholine-induced Asystole. An adjunct In Open Heart Operations With Extracorporeal Circulation," in *Extracorporeal Circulation* 1958, pp. 451–48; Lillehei et al., "The Direct Vision Correction Of Calcific Aortic Stenosis By Means Of A Pump Oxygenator And Retrograde Coronary Sinus Perfusion," *Disease Of The Chest*, 1956, 30:123–132; Lillehei et al., "Clinical Experience With Retrograde Perfusion Of The Coronary Sinus For Direct Vision Aortic Valve Surgery With Observations Upon Use of Elective Asystole Or Temporary Coronary Ischemia," in *Extracorporeal Circulation*, 1958, pp. 466–85; Lillehei et al., "The Surgical Treatment Of Stenotic Or Regurgitant Lesions Of The Mitral And Aortic Valves By Direct Vision Utilizing A Pump Oxygenator," *Journal of Thoracic & Cardiovascular Surgery*, 1958; 35:154–91. Conrad R. Lam, et al. *Annals of surgery* 1957; 146:439–49. Intravenous adenosine has been used to facilitate MIDCAB. M. Clive Robinson, First International Live Teleconference. Least- Invasive Coronary Surgery, The John Radcliffe Hospital, Oxford, England, Mar. 21 and 22, 1996.

Ventricular asystole has been achieved by direct injection of lignocaine into the interventricular septum. Khanna and Cullen, "Coronary Artery Surgery With Induced Temporary Asystole And Intermittent Ventricular Pacing: An Experimental Study," *Cardiovascular Surgery* 1996; 4(2):231–236. Epicardial pacing wires were placed, and ventricular pacing was employed to maintain an adequate cardiac output. Esmolol has been used as a cardioplegic agent during cardiopulmonary bypass. Mauricio Ede et al., "Beyond Hyperkalemia: B-Blocker-Induced Cardiac Arrest For Normothermic Cardiac Operations," *Annals of Thoracic Surgery*, 1997; 63:721–727.

In summary, there is a need for a surgical approach that avoids the risks and costs of cardiopulmonary bypass while preserving the benefits of a motionless operative field to achieve a precise coronary anastomosis. There is a further need for methods and compositions that enable predictable, controllable, transient arrest of the heart, which stop or slow the beating heart with acceptable half-life and quick onset of effect. There is a need for compositions and methods for transient arrest of the heart which can be used in a variety of medical and surgical procedures conducted on the heart, vascular system, brain, or other major organs, where pulsatile flow, movement associated with arterial pulsations, or bleeding is undesirable during the procedure.

SUMMARY OF THE INVENTION

Methods, compositions and apparatus are provided which are useful for diagnostic and therapeutic medical and surgical applications. The methods, compositions and apparatus are useful for cardiac surgery and other procedures, such as, for example, vascular and neurosurgery procedures, imaging procedures, robotically assisted surgical procedures, and procedures involving delivery of medical devices such as intravascular stents, bypass grafts, stent grafts, and occlusive/embolic devices (e.g., cerebral aneurysm coils), which may benefit from precise control of cardiac contraction, and/or minimized pulsatile flow and bleeding. Using the methods, compositions and apparatus disclosed herein for conducting a medical or surgical procedure, such as a coronary bypass, a substantially motionless operative field is provided.

In one embodiment, a method of performing a procedure on a human patient is provided, the method comprising: administering an effective amount of a composition capable of inducing reversible ventricular asystole to the patient, while maintaining the ability of the heart to be electrically paced; electrically pacing the heart with an electrical pacing system, thereby to maintain the patient's blood circulation; selectively intermittently stopping the electrical pacing to allow ventricular asystole; and conducting the procedure during the time that the electrical pacing is intermittently stopped.

In another embodiment, a method of performing an aortic aneurysm repair procedure is provided in which a graft member is positioned within a region of a patient's aorta, comprising inducing, prior to or during the repair procedure, at least one period of reversible ventricular asystole, while maintaining the ability of the heart to be electrically paced; wherein the period of asystole has a duration of more than approximately one minute. In one embodiment, the at least one period of reversible ventricular asystole is induced prior to or during positioning of the graft member in the aorta.

In another embodiment, a method of performing transmyocardial revascularization (TMR) is provided in which at least one blood flow channel is formed in a wall of the heart of a patient and is in fluid connection with a chamber of the heart. Prior to or during formation of the channel, at least one period of reversible ventricular asystole is induced, while maintaining the ability of the heart to be electrically paced, wherein the period of asystole has a duration of more than approximately one minute. The at least one blood flow channel, thus, may be formed during the period of asystole. In one embodiment, the blood flow channel in the heart is created by irradiating an exterior surface of the heart with laser energy. In another embodiment, the blood flow channel in the heart is created by irradiating an interior surface of the heart with laser energy.

In another embodiment, a method of imaging at least one intracorporeal aspect of a patient is provided comprising inducing, prior to or during image acquisition (of one or more images), at least one period of reversible ventricular asystole, and wherein at least one step of the image acquisition is performed during the period of asystole. The imaging procedure may be, for example, a CT scan or an MRI procedure. In another embodiment, the imaging procedure is echocardiography, comprising administering an ultrasonic probe to a patient for imaging an anatomical structure within the patient's body by ultrasonic image acquisition. The echocardiography may be, for example, transesophageal echocardiography in which an ultrasonic probe is passed through a mouth of a patient and inserted into the patient's esophagus for imaging an anatomical structure within the patient's thoracic cavity by ultrasonic image acquisition.

In another embodiment, a procedure of introducing or inserting an occlusive material (which may comprise a substance(s) or a device) within a blood vessel of a patient is provided, comprising inducing, prior to or during the procedure, at least one period of reversible ventricular asystole. The material thus may be introduced or deployed during the period of asystole. In one embodiment, the at least one period of reversible ventricular asystole is induced prior to or during the deployment of the occlusive material. Where an occlusive device is used, it may comprise, for example, an intravascular coil. In one embodiment, the disease condition treated with the procedure may comprise an arteriovenous malformation. In another embodiment, the disease condition treated with the procedure may comprise an arteriovenous fistula. The occlusive material may be introduced into the blood vessel via a delivery catheter which is percutaneously introduced into the patient's vasculature system.

In one embodiment, a method of performing a robotically-assisted surgical procedure is provided in which a practitioner uses one or more robotically-controlled devices to perform a surgical procedure within a body of a patient, comprising performing a robotically assisted procedure and inducing, prior to or during the robotically assisted procedure, at least one period of reversible ventricular asystole.

For the diagnostic and therapeutic medical and surgical procedures disclosed herein, the period of asystole may have a duration of, for example, about 3 to 20 minutes. In one embodiment, the period of asystole is induced by administering an AV node blocker and a β-blocker to the heart at a sufficient dosage amount of each to induce asystole in the heart. The AV node blocker may comprise a cholinergic receptor agonist such as, for example, carbachol. The β-blocker may comprise, for example, propranolol. In one embodiment, the method comprises electrically pacing the heart to maintain the patient's blood circulation. The method may further comprise selectively intermittently stopping the electrical pacing during the asystole at least once during the procedure for an intermittent period, each of the one or more intermittent periods having a duration of, for example, about 1 to 30 seconds. In one embodiment, the β-blocker is administered prior to the AV node blocker. The β-blocker may be administered in an amount sufficient to substantially reduce the amount of AV node blocker required to induce asystole of the heart.

For the medical and surgical diagnostic and therapeutic procedures disclosed herein, the AV node blocker and the β blocker may be administered to the right or left coronary artery of the heart, for example, through a drug delivery catheter which has at least one discharge opening which is positioned in the right or left coronary artery. The discharge opening, in one embodiment, is positioned in the right coronary artery proximate to the AV node artery. The drug delivery catheter may be percutaneously inserted into the right coronary artery from a peripheral vascular access point, which may be, for example, a brachial artery, for example a femoral artery, for example a carotid artery, for example a radial artery.

For the medical and surgical diagnostic and therapeutic procedures disclosed herein, the propranolol may be administered as one or more bolus infusions at a total dosage amount of, for example, about 1 to 8 mg. The carbachol may be administered as one or more initial bolus infusions at a total dosage amount of, for example, about 0.001 to 1.0 mg per bolus. In another embodiment, the method comprises maintaining the period of asystole by administering a continuous intracoronary infusion of carbachol to the heart of the patient at a rate of, for example, about 0.001 to 0.3 mg/min over a time period of, for example, about 5 to 90 minutes.

In one embodiment, a system for performing a medical procedure on a patient is provided comprising: a drug delivery device; a transvenous pacing catheter; and at least one endoscopic instrument which is capable of performing a diagnostic or therapeutic interventional procedure within a vessel or bodily organ within the patient's body. In one embodiment, the system further comprises at least one guide catheter. The drug delivery device may have a sufficient length and flexibility to allow transluminal positioning of the device into a right or left coronary artery of the heart of the patient from a peripheral access vessel. The transvenous pacing catheter may have a sufficient length and flexibility to allow transluminal positioning of the catheter into a right (or left) ventricle of the heart of the patient from a peripheral access vessel.

In one embodiment, the system further comprises an energy source coupled to the endoscopic instrument, wherein the energy source may be, for example, a laser energy source. The endoscopic instrument may comprise, for example, a flexible lasing apparatus, for example an endoscopic viewing device, for example a transesophageal echocardiographic probe, for example an endograft aortic prosthesis delivery catheter, for example a neurovascular stent delivery catheter, for example a neurovascular coil delivery catheter, for example an electrophysiologic mapping catheter, for example an ablation catheter, for example a stent delivery catheter, for example an angioplasty catheter.

In one embodiment, the system further comprises at least a first container comprising a dosage amount of an AV node blocker, which may be a cholinergic receptor agonist such as, for example, carbachol. The system may further comprise a second container comprising a β-blocker such as, for example, propranolol.

In one embodiment, the system further comprises an electrical pacing system operatively coupled to the pacing catheter which may comprise, for example, an extracorporeal pacer, a switch remotely coupled to the pacer, and an actuator arranged remote from the pacer and coupled to the switch. In one embodiment, the actuator comprises a foot pedal.

The above is a brief description of some deficiencies in the prior art and advantages of the present invention. Other features, advantages and embodiments of the invention will be apparent to those skilled in the art from the following description, accompanying drawings and appended claims.

BRIEF DESCRIPTION OF THE DRAWINGS

FIG. 1D diagrammatically shows one outlet lead arrangement coupled to the heart of a patient;

FIG. 1E diagrammatically shows another outlet lead arrangement coupled to the heart of a patient;

DETAILED DESCRIPTION

Figure 1:
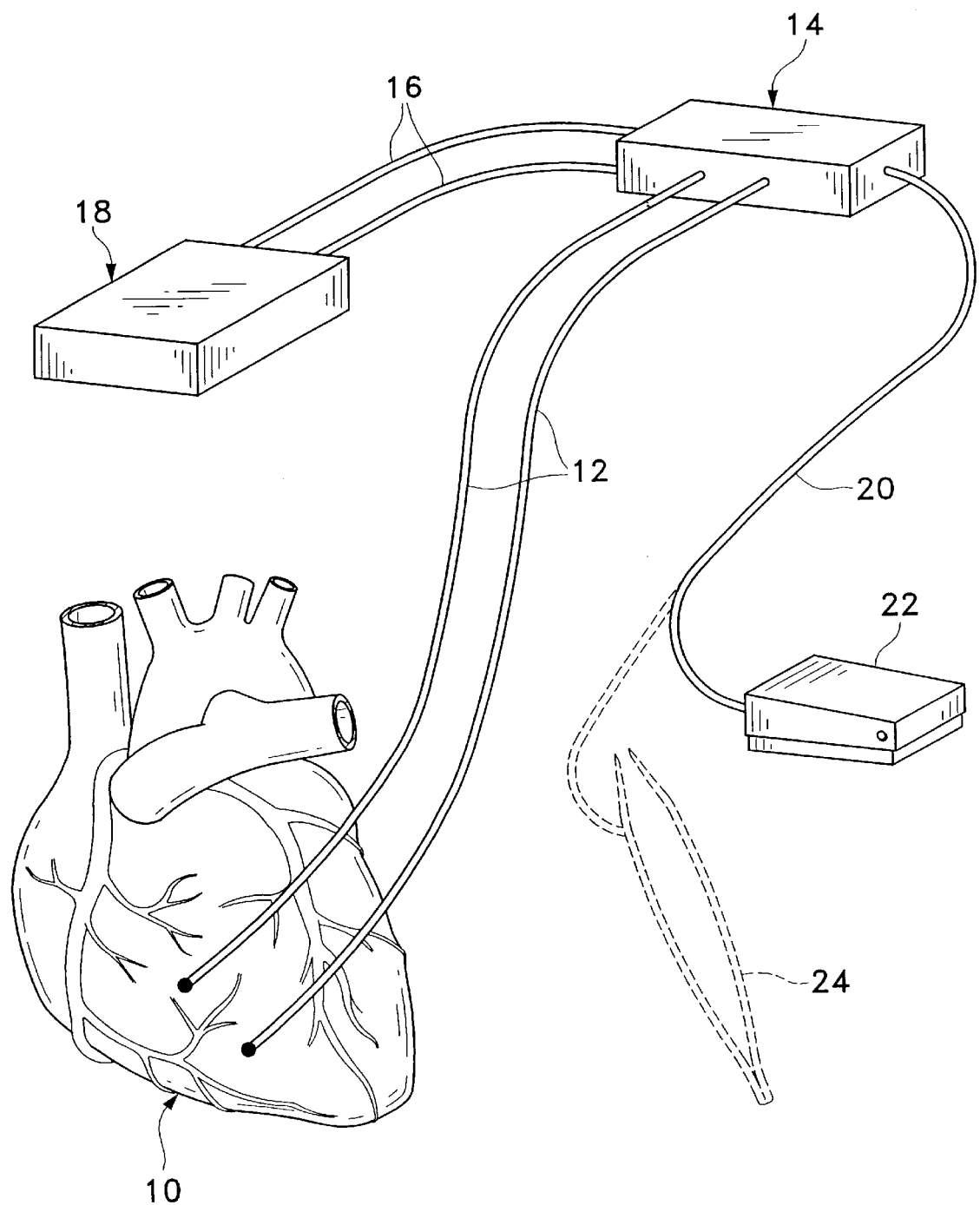
FIG. 1 diagramatically shows a pacing system in accordance with the principles of the invention.

Methods, compositions and apparatus are provided which are useful for diagnostic and therapeutic medical and surgical applications, examples of which are described hereinafter. In one embodiment, the compositions and methods are useful for coronary artery bypass procedures, with or without cardiopulmonary bypass. Using the methods, compositions and apparatus for conducting a coronary artery bypass disclosed herein, a motionless operative field is provided.

The methods, compositions and apparatus of the invention are useful for any procedure which requires or may benefit from controlled temporary complete heart block and suppression of ventricular escape beats. Nonlimiting examples of such procedures include coronary bypass surgery (with full or partial sternotomy or thoracotomy), transmyocardial laser revascularization, tachyarrhythmia operations such as electrophysiology lab procedures (diagnostic and therapeutic ablation of arrhythmias), imaging procedures of the heart and great vessels such as CAT scan, MRI, or transesophageal echocardiography procedures, percutaneous transluminal coronary angioplasty, placement of stents such as coronary, aortic, or carotid artery stents, for example placement of stents to treat left main coronary artery disease, placement of occlusive/embolic devices (e.g., embolic coils) or materials in blood vessels to occlude them such as at the site of an arteriovenous (AV) malformation, operations where uncontrollable hemorrhage is present or anticipated or control of significant hemorrhage is required during the surgical procedure (for example, treatment of injuries to the liver, spleen, heart, lungs, or major blood vessels, including iatrogenic and traumatic injuries to such organs or structures), other procedures including percutaneous aortic aneurysm graft placement, valve procedures such as mitral valve commissurotomy procedures, robotically assisted cardiac surgery procedures, atherectomy or roto-ablation procedures, transvascular procedures in which a stenosis in an artery is bypassed using a vein conduit, for example, developing cardiovascular angiogenesis procedures in which angiogenesis (blood vessel formation) agents are delivered to the heart to control formation of new blood vessels in the heart as one method to treat ischemic heart disease, and neurosurgical procedures, such as aneurysm repair. The methods and compositions are useful for any surgical procedure or intervention on the heart, vascular system, brain, or other major organs, where pulsatile flow, movement associated with arterial pulsations, or bleeding prevents or hinders successful completion of the operative procedure.

The compositions and methods can be used to induce ventricular asystole in a patient, for example, prior to or during a medical or surgical procedure. The term "ventricular asystole" as used herein refers to a state wherein autonomous electrical. conduction and escape rhythms in the ventricle are suppressed. Preferably, a state of the heart is induced wherein the heart beats less than about 25 beats per minute, for example, less than about 12 beats per minute. The induced ventricular asystole is reversible and after reversal, the heart functions are restored, and the heart is capable of continuing autonomous function. Preferred are pharmaceutically acceptable compositions which are capable of inducing transient reversible ventricular asystole reliably and predictably.

The compositions capable of suppressing autonomous ventrical electrical conduction and escape rhythms may in one embodiment comprise an atrioventricular (AV) node blocker. As used herein, the term "AV node blocker" refers to a compound capable of reversibly suppressing autonomous electrical conduction at the AV node, while still allowing the heart to be electrically paced to maintain cardiac output. Preferably, the AV node blocker, or composition comprising the AV node blocker, reduces or blocks ventricular escape beats and cardiac impulse transmission at the AV node of the heart, while the effect on depolarization of the pacemaker cells of the heart is minimal or non-existent. The AV node blocker preferably induces third degree, or complete AV block, or significantly slows AV conduction to the point where the ventricular beat is less than about 25 beats per minute, for example less than about 12 beats per minute. The AV node blocker, or composition comprising the AV node blocker, preferably induces reversible ventricular asystole, and renders the heart totally pacemaker dependent for a limited period of time, such that a pacemaker may be used to maintain pacing and to intermittently stop pacing during a step of a procedure. After the procedure is completed, for example, less than about 2 hours, the heart then can be returned to its normal intrinsic rhythm.

Exemplary AV node blockers include calcium channel blockers, adenosine A1 receptor agonists, adenosine deaminase inhibitors, cholinesterase inhibitors, monoamine oxidase inhibitors, serotoninergic agonists, antiarrythmics, cardiac glycosides, local anesthetics and combinations thereof. Examples of AV node blockers include adenosine, digoxin, digitalis, procaine, lidocaine, procainamide, quinidine, verapamil, chloroquine, amiodarone, ethmozine, propafenone, flecainide, encainide, pilocarpine, diltiazem, dipyridamole, ibutilide, zapranest, sotalol and metoclopromide and combinations thereof. AV node blocking also can be achieved by other methods including direct electrical stimulation, vagal nerve stimulation, stimulation with ultrasonic energy, and temporary cooling of the AV node using a cryonic agent. Cryonic agents include devices, such as cryostats, and cryogenic chemicals which are capable of inducing low temperatures at the AV node.

The AV node blocker, capable of causing ventricular asystole, in a preferred embodiment is a cholinergic agent. As used herein, the term "cholinergic agent" refers to a cholinergic receptor modulator, which is preferably an agonist. The cholinergic agent in a preferred embodiment is carbachol (carbamyl choline chloride). Other cholinergic agents which may be used include any naturally occurring cholinergic (acetylcholine) receptor agonists or synthetic derivatives. Exemplary cholinergic agents include acetylcholine, methacholine, bethanechol, arecoline, norarecoline, pyridostigmine, neostigmine, tensilon and other agents that increase cyclic GMP levels by direct or indirect receptor stimulation.

In one embodiment, compositions and methods are provided which are capable of slowing or preventing autonomous conduction of electrical impulses from the sinoatrial node to the ventricle, with suppression of escape beats in the AV node and the ventricle. Preferably, a state of the heart is induced wherein the heart beats less than about 25 beats per minute, for example, less than about 12 beats per minute.

As used herein, the term "β-adrenergic blocking agent," also referred to as a "β-blocker", is defined as an agent which is capable of blocking β-adrenergic receptor sites. In a preferred embodiment, the β-blocker is propranolol. Other β-blockers which can be used include atenolol, acebutolol, labetalol, metoprolol, nadolol, oxprenolol, penbutolol, pindolol, sotalol and timolol. Other exemplary β-blockers include celiprolol, betaxolol, bevantolol, bisoprolol, esmolol, alprenolol, carterolol, nadolol or teratolol, and mixtures thereof. The β-blocker may be any naturally occurring or synthetic analogue capable of blocking β-adrenergic receptor sites.

In one embodiment, reversible ventricular asystole in a beating heart in a human patient is induced by administering to a patient a composition capable of suppressing autonomous ventricular electrical conduction and escape rhythms. In one embodiment, the composition capable of inducing ventricular asystole may comprise a first compound capable of inducing ventricular asystole, such as an AV node blocker, and a β-blocker present in an amount sufficient to substantially reduce the amount of the compound required to induce ventricular asystole. In one embodiment, the combination of the compound, such as an AV node blocker together with the β-blocker provides a synergistic effect such that the amount of AV node blocker required to induce reversible ventricular asystole may be reduced in comparison to the amount of AV node blocker required alone. Methods also are provided wherein the β-blocker is administered either prior to or contemporaneously with the compound capable of inducing ventricular asystole, in an amount effective to substantially reduce the amount of the compound required to be administered to induce ventricular asystole.

In a particular embodiment, ventricular asystole is induced in a beating heart in a human patient by administering a cholinergic receptor agonist and a β-blocker to the heart of the patient in an effective amount to induce ventricular asystole, wherein the amount administered of the cholinergic receptor agonist alone or the β-blocker alone is not sufficient to induce ventricular asystole. In one embodiment, the co-administration of the β-blocker with the cholinergic agent provides a synergistic effect, such that the amount of cholinergic agent which is administered to induce reversible ventricular asystole can be reduced.

Reversible ventricular asystole in the heart of a human patient thus may be induced by administration of an AV node blocker, or mixture of AV node blockers, to the heart of the patient. Reversible ventricular asystole optionally is induced by administration of the combination of an AV node blocker, such as a cholinergic agent, and one or more β-blockers to the heart of the patient. The β-blocker is preferably administered either prior to or contemporaneously with the AV node blocker.

In an embodiment wherein a surgical procedure is to be conducted, after inducing reversible ventricular asystole, the method further includes electrically pacing the heart with an electrical pacing system, thereby to maintain the patient's blood circulation; selectively intermittently stopping the electrical pacing to allow ventricular asystole; and conducting the surgical procedure during the intervals of time that the electrical pacing is intermittently stopped.

The method may be used, for example, in a cardiac surgical procedure. Electrical pacing may be controlled by a surgeon conducting the surgical procedure by selectively manipulating a control that is functionally coupled to the electrical pacing system. Once reversible ventricular asystole is achieved, pacing of the heart may be implemented using a external pacemaker connected to the heart, and the pacemaker may be periodically deactuated, for example by way of a foot switch, to allow reversible ventricular asystole, thereby facilitating the performance of coronary artery bypass, with or without cardiopulmonary bypass, or other procedures elsewhere in the body of the patient.

For example, to conduct a coronary artery bypass, the patient's heart is provided with ventricular pacing electrodes connected to an electrical pacing device, which is controlled by the surgeon. A composition, for example, comprising an AV node blocker and a β-blocker, then is administered to the patient to induce reversible ventricular asystole. The surgeon then employs the pacing device to pace the heart and sustain the patient's circulation. The surgeon intermittently stops the electrical pacing for a few seconds to place a single suture, and re-starts it after each successive suture, thus permitting a precise coronary anastomosis to be performed. In this method, the ventricles (and/or atria) are electrically paced and maintain a normal cardiac output except for the brief periods of time that are required to accurately place a single suture in the coronary artery, preferably about 2 to 15 seconds, and more preferably about 2 to 5 seconds. Using the methods and compositions described herein, the rate and timing of ventricular contraction can be directly controlled.

In the method, the composition inducing ventricular asystole, such as an AV node blocker in combination with a β-blocker or AV node blocker administered after a β-blocker, may be infused through a catheter placed into the right coronary artery.

In one embodiment, the composition is delivered locally to the AV node of the heart upon which it acts via the AV node artery of the heart. Preferably the composition is delivered to the right coronary artery which feeds blood to the AV node artery. In a majority of patients, the right coronary artery is the main vessel supplying blood to the right side of the heart and to the AV node. However, where the right coronary artery is substantially totally occluded, and in a small subset of about 20% of patients, the first septal branch of the left anterior descending artery which originates from the left coronary artery may be the vessel which delivers blood to the AV node and can be selected as the delivery conduit for delivering the composition to the AV node. Additionally, other possible routes of administration to the AV node may include Kugel's artery and the right superior descending artery. Preferably, the composition is delivered to the right coronary artery or left coronary artery at a location near the bifurcation to the AV node artery and proximal to the right coronary artery's bifurcation into the posterior descending artery by any one of a number of drug delivery means, such as a drug delivery catheter suitably positioned within the right coronary artery. Other methods of administration may be used including hypodermic needle injection into, for example, any of the vessels noted above which may supply blood to the AV node, such as the right coronary artery or the first septal branch. Other methods of administration include needle injection into the aorta, needle injection directly into the AV node artery or the AV node itself, a transepicardial absorption pad, i.e., a myocardial patch which slowly releases the composition directly into the heart's myocardium, and for example, an intraoperative cannula or other similar guide introducer or sheath which can be surgically placed by a surgeon into the aorta or the ostium of a coronary vessel without the need for X-ray fluoroscopy.

As the composition achieves the desired effect of ventricular asystole, the ventricle is electrically paced to maintain a stable rhythm and blood pressure. To interrupt the electrical pacing of the heart, the surgeon uses a convenient control means, such as a foot pedal or hand held actuator, as shown in FIG. 1, and is thereby able to stop the heart as sutures are placed in the coronary arterial wall. Because the heart is motionless during the critical period as the surgeon places sutures, precision and safety are enhanced. The time required to place a single suture into the coronary artery preferably does not exceed 15 seconds, and is preferably about 2 to 5 seconds, most preferably about 2 to 4 seconds. Thus, the compositions can permit the elimination of the translational motion of the beating heart.

Compositions capable of inducing ventricular asystole in a patient are provided which in one embodiment include a cholinergic receptor agonist and a β-blocker, wherein the amount of the cholinergic receptor agonist alone or the β-blocker alone in the composition is not sufficient to induce ventricular asystole in the patient. Methods are provided wherein the cholinergic receptor agonist and the β-blocker may be administered, either sequentially or together, thereby to induce ventricular asystole in a patient, wherein the amount of the cholinergic receptor agonist administered alone or the β-blocker administered alone is not sufficient to induce ventricular asystole in the patient.

In one embodiment, wherein a cholinergic agent and a β-blocker are administered to the heart of a human patient to induce reversible ventricular asystole, when the β-blocker used is propranolol and the cholinergic receptor agonist used is carbachol, a continuous infusion rate of about 0.01 to 4.8 µg/kg/min, for example about 0.1 to 4.8 µg/kg/min of carbachol can be used, e.g., an infusion rate of carbachol of 0.1 to 2.1 µg/kg/min, or about 0.1 to 1.5 µg/kg/min, or in one preferred embodiment, about 1.5 to 2.1 µg/kg/min. When an initial bolus of propranolol is administered prior to or during administration of an initial bolus of carbachol, the ratio by weight of propranolol to carbachol in the bolus injections can range, for example, from about 1:2 to 35:1, or, in another embodiment, from about 1:1 to 15:1, or, in another embodiment, from about 2:1 to 10:1, or, in another embodiment, is about 5:1.

In another embodiment, compositions capable of inducing ventricular asystole in a patient are provided, comprising a compound, such as an atrioventricular (AV) node blocker, and a β-blocker, wherein the β-blocker is present in an amount sufficient to substantially reduce the amount of the compound required to induce ventricular asystole in the patient. The AV node blocker is preferably a cholinergic agent. Due to the synergistic effect of the presence of the β-blocker, the cholinergic agent may be present in the composition in a reduced amount which is, for example, about 1–90%, about 1–50%, or about 1–20%, or for example, about 2–14%, or in another embodiment about 80% or less, for example about 50% or less, or about 10% or less by weight of the amount of the cholinergic agent alone required to induce ventricular asystole in the patient. Advantageously, the co-administration of the β-blocker with the AV node blocker provides a synergistic effect, such that the amount of AV node blocker which is administered to induce ventricular asystole may be reduced.

Additionally, in the methods disclosed herein, ventricular asystole may be induced in a patient by administration, together, or sequentially, of a compound, such as an AV node blocker, together with a β-blocker, wherein the β-blocker is administered in an amount sufficient to substantially reduce the amount of the compound required to induce ventricular asystole in the patient. In a preferred embodiment, the compound is a cholinergic agent, such as carbachol. Due to the synergistic effect of the administration of the β-blocker, the cholinergic agent may be administered in reduced amount which is, for example, about 1–90%, about 1–50%, or about 1–20%, or in one embodiment, about 2–14%, or in another embodiment about 80% or less, about 50% or less, or about 10% or less by weight of the amount of the cholinergic agent alone required to induce ventricular asystole in the patient.

Additionally, due to the synergistic effect, the β-blocker may be present in combination with other compounds capable of inducing ventricular asystole, in an amount effective to reduce the amount of the compound required to induce ventricular asystole, for example to about 5–90%, e.g., 30–50% or less by weight of the amount alone required to induce ventricular asystole.

The administration of the β-blocker is preferably prior to, or contemporaneously with, the administration of the cholinergic agent, and in one embodiment results in a synergistic effect between the β-blocker and the cholinergic agent. The amount of β-blocker present is preferably not sufficient to induce ventricular asystole by itself, and is sufficient only to cause a local β-blockade, but has a minimal effect on electrical conduction of the heart, or is low enough to cause only a first degree heart block.

In another embodiment, in order to induce reversible ventricular asystole in the heart of a patient, while maintaining the ability of the heart to be electrically paced, an AV node blocker is administered in combination with an effective amount of a second compound, such as a β-blocker to reduce or suppress ectopic ventricular activity while maintaining the ability of the heart to be electrically paced. In one embodiment, the β-blocker, alone or in combination with the AV node blocker, is capable of substantially suppressing ectopic ventricular beats in the heart while maintaining the ability of the heart to be electrically paced. For example, an AV node blocker, such as an antiarrythmic, such as flecainide, and a β-blocker, such as propranolol, may be administered. In one preferred embodiment, the β-blocker is administered prior to the AV node blocker. In another embodiment, a composition is provided that includes an AV node blocker and a β-blocker in an amount effective to induce reversible ventricular asystole and wherein the β-blocker is present in an amount effective to reduce or suppress ectopic ventricular activity after administration.

The use of a cholinergic agent, such as carbachol, in combination with a β-blocker, such as propranolol, preferably produces ventricular asystole at significantly reduced dosages of the cholinergic agent, while maintaining a short half-life and rapid onset of effect. A preferred half-life is on the order of about one to ten minutes. A preferred onset of effect is less than one minute after administration. It is possible to induce onset of ventricular asystole within about thirty seconds after administration of carbachol and propranolol to the heart.

The compositions preferably are capable of inducing reversible transient ventricular asystole of a beating heart to facilitate the performance of minimally invasive surgical procedures, while still permitting the heart to be electrically paced. The compositions, including for example a cholinergic agent, preferably can reliably and in a dose-dependent fashion produce extended periods of reversible ventricular asystole, for example, for up to about two hours upon either administration of a single dose, or continuous infusion, depending upon the composition. In preferred embodiments, the ventricular asystole is chemically reversible. For example, in the case of carbachol, the ventricular asystole can be reversed by administering atropine, for example by an intravenous bolus injection, providing an important advantage of safety during the procedure.

In one preferred embodiment, to induce ventricular asystole, the β-blocker is administered to the heart before the cholinergic agent. For example, the β-blocker in one embodiment is administered in a single bolus injection into the right or left coronary artery, and then the cholinergic agent is administered by a single bolus injection followed by continuous infusion into the right or left coronary artery throughout the surgical procedure, to maintain the ventricular asystole. In another embodiment, where the β-blocker has a relatively short half life, such as esmolol, the β-blocker may be administered by continuous infusion, or a plurality of bolus infusions. The ventricular asystole continues as long as administration of the cholinergic agent is continued. In a preferred embodiment, due to the prior administration of the β-blocker, it is possible to administer a significantly reduced amount of the cholinergic agent and thereby reduce the occurrence of side-effects such as systemic hypotension. Moreover, depolarization of the pacemaker cells of the heart by the administered composition is preserved, thereby making it possible to selectively electrically pace the heart to permit the performance of a surgical procedure while the heart is under transient ventricular asystole.

The time between administration of the β-blocker and the cholinergic agent is preferably long enough to permit the β-blocker to cause a local β-blockade of the pacemaker cells of the heart. After bolus administration, the time interval can be, for example about two minutes. In the case of intravenous or other forms of administration, several minutes or even hours may be required to permit the β-blocker to affect the pacemaker cells of the heart. The subsequent administration of the cholinergic agent may be controlled by the surgeon. Bolus infusion of higher doses can be used to give a dose dependent effect, while continuous infusion of lower doses also may be given to maintain ventricular asystole. In another embodiment, the β-blocker may be administered by an initial intracoronary bolus followed by a continuous infusion.

In one embodiment, the AV node blocker, such as a cholinergic agent, such as carbachol, is administered in an initial intracoronary bolus of about 0.1 to 150 μg/kg body weight of patient, or about 2 to 20 μg/kg body weight of patient, for example, about 4 to 16 μg/kg, or about 6 to 14 μg/kg, or in one embodiment, about 8 to 12 μg/kg body weight, in a suitable pharmaceutically acceptable carrier. The AV node blocker, such as carbachol, is preferably administered over a time period of about 0.1 to 3 minutes, preferably about 0.5 to 1 minute. In a preferred embodiment, the AV node blocker, such as a cholinergic agent, such as carbachol, is administered in an intracoronary bolus of about 0.10 to 10 μg/kg body weight of patient, for example about 0.10 to 5.0 μg/kg body weight in a pharmaceutically acceptable carrier over a time period of about 0.1 to 3 minutes, preferably about 0.5 to 1 minute.

The bolus infusion of the AV node blocker such as a cholinergic agent is in one embodiment followed by a continuous intracoronary infusion at about 0.1–5 μg/kg body weight/ min of the AV node blocker, which in a preferred embodiment is a cholinergic agent. The infusion rate in one embodiment is about 0.01 to 4.8 μg/kg/min, for example about 0.1–4.8 μg/kg body weight of patient/min, for example about 0.1–2.1 μg/kg/min, or about 0.1–1.5 μg/kg/min, or about 0.1–1.0 μg/kg/min, or in another embodiment, about 0.1–0.5 μg/kg/min. Optionally, the cholinergic agent is combined with a β-blocker. In one embodiment, a typical total adult dosage of an AV node blocker, such as a cholinergic agent, such as carbachol, is about 0.1 to 15 mg, for example about 1 mg to 15 mg, for example about 0.1 to 2 mg in a preferred embodiment. This dosage can produce reversible ventricular asystole, for example, for a time period of about 5 to 120 minutes, for example, about 5 to 90 minutes, preferably about 30 to 90 minutes, e.g., about 75 minutes. The dosage may also be, for example, about 1 to 12 mg, or about 1 to 10 mg, or in one embodiment about 1 to 5 mg. The dosage may be adjusted depending on the surgical procedure.

The β-blocker, such as propranolol, in one embodiment is administered through the right or left coronary artery in a dosage of about 0.01 to 0.07 mg/kg body weight of patient, for example, 0.01 to 0.05 mg/kg, or about 0.01 to 0.04 mg/kg. The total amount of propranolol administered is in one embodiment about 1 mg to 8 mg, or 1 mg to 6 mg, e.g., about 1 mg to 5 mg, or, for example, about 2 to 4 mg, or about 3mg.

For example, one embodiment to induce transient reversible ventricular asystole in a patient is as follows. An intracoronary injection of 0.5 to 8 mg, e.g., about 0.5 to 4 mg, e.g., about 1.0 mg, of propranolol is administered by intracoronary infusion through a drug delivery catheter positioned in the right coronary artery just proximate to the AV node artery, over a time period of about 0.5–3 minutes, e.g., about 1 minute, preferably followed by a saline flush, such as a 2 mL saline flush. This is followed by an intracoronary bolus injection of about 0.01 to 0.5 mg, e.g., about 0.025 to 0.3 mg, e.g., about 0.1 mg carbachol administered over about 0.5 to 3 minutes, e.g., about 1 minute. The method may include repeating the above bolus drug dosing regimen one or more times during the procedure to induce a controlled and stable asystolic heart during the procedure. Alternatively, the bolus drug regimen above may be followed by an intracoronary infusion of carbachol at a rate of about 0.001 to 0.3 mg/min, for example about 0.005 to 0.3 mg/min, for example about 0.01 to 0.3 mg/min, e.g., about 0.025 to 0.3 mg/min, for example, about 0.005 to 0.1 mg/min, for example, about 0.01 to 0.1 mg/min, or, e.g., about 0.05 to 0.1 mg/min, e.g. about 0.0825 mg/min, for a time period of about 5 to 90 minutes, preferably about 30 to 90 minutes, e.g., about 75 minutes. Alternatively, carbachol may be delivered by intracoronary administration to the heart as one or more bolus infusions at a per bolus dosage of about 0.001 to 1.0 mg, e.g., about 0.01 to 0.5 mg, e.g., about 0.05 to 0.5 mg, e.g., about 0.025 to 0.30 mg, e.g., about 0.01 to 0.1 mg, e.g., about 0.05 mg to maintain ventricular asystole during the duration of the procedure. A dosage amount of phenylephrine in the range of about 0.1 to 1.0 mg if needed may be administered to counteract any hypotension effects associated with carbachol administration. Additionally, nitroglycerine may be required in some patients to counteract the coronary vasoconstrictive effects of systemic phenylephrine administration. Other intracoronary vasodilators for coronary artery spasm may also be used such as glyceryl trinitrate, papaverine, or verapamil.

Additionally, in one embodiment, where the patient is under prior therapeutic treatment with a β-blocker, lower amounts of β-blocker, or alternatively no β-blocker may be required prior to the surgical procedure. Moreover, in certain situations overdrive suppression (i.e., pacing at about 90 to 110 beats/min for about 10 seconds) may be used in addition to the initial intracoronary bolus of carbachol and propranolol to initiate ventricular asystole prior to carbachol continuous infusion.

Compositions may be administered by intravenous, intracoronary and intraventricular administration in a suitable carrier. Compositions may be administered locally to the heart, for example, by direct infusion to the right coronary artery as a single bolus injection, continuous infusion, or combination thereof. This can be achieved, for example by administration to the proximal or ostial portion of the right coronary artery, using a guiding catheter or drug delivery catheter, or by administration just proximal to the AV node artery by means of a drug delivery catheter positioned in the right coronary artery. Intraventricular (left side) injection also may be used. Continuous infusion can be continued as long as necessary to complete the procedure. In one embodiment, the infusion rate can range from about 0.01 to 0.5 mg-min$^{-1}$, e.g., about 0.01 to 0.3 mg-min$^{-1}$, or about 0.015 to 0.15 mg-min$^{-1}$, for example about 0.016 to 0.12 mg-min$^{-1}$. Methods of administration include intravenous, intra-atrial, intra-aortic, and administration via the aortic root, or coronary artery. Administration may be via any suitable route, for example via the left or right ventricle, for example proximal to the AV node artery, or via the aorta, pulmonary artery, pulmonary vein, middle cardiac vein, right atrium or the coronary sinus. In another embodiment, administration may be by direct administration into the AV node artery or AV node. In one embodiment, administration may be via a hypodermic needle to the AV node.

In addition to local delivery, systemic delivery routes of administration known in the art may be used, such as oral, transdermal, intranasal, suppository and inhalation. For example, in addition to injection as described above, the β-blocker may be administered orally in a suitable carrier for oral administration. The patient also may be on therapeutic treatment with a β-blocker prior to the surgical procedure and thus may require lower amounts, or even no additional β-blocker prior to the surgery.

The compositions capable of inducing ventricular asystole, such as an AV node blocker and β-blocker, may be provided in pharmaceutically acceptable carriers including diluents. A variety of carriers may be used that are known in the art, preferably in sterile form. Suitable carriers include sterile water, aqueous normal saline solutions, and aqueous solutions such as lactated Ringer's solution, or a solution of a sugar such as dextrose, for example 5% dextrose in water or saline. Other possible carriers, which may be provided, for example, in an aqueous solution, include sodium citrate, citric acid, amino acids, lactate, mannitol, maltose, glycerol, sucrose, ammonium chloride, NaCl, KCl, CaCl$_2$, sodium lactate, free radical scavengers (e.g., allopurinol, vitamin C, vitamin E, etc.) and sodium bicarbonate. In one embodiment, the carrier may be D5W, a solution of 5% dextrose in water. Other carriers include buffered aqueous solutions, such as an aqueous solution comprising 5 mM HEPES (N-[2-hydroxyethyl)piperazine-N'-[2-ethanesulfonic acid]). Antioxidants or preservatives such as ascorbic acid also may be provided in the compositions. Carriers known in the art, for example, for injection, oral delivery, delivery via a suppository, transdermal delivery and inhalation also may be used.

In one embodiment, compositions are provided which include an AV node blocker, such as a cholinergic agent and β-blocker either together or separately in a pharmaceutically acceptable carrier. In another embodiment, containers containing unit dosage forms of the AV node blocker, such as a cholinergic agent and the β-blocker, either in separate containers or in a single container are provided. In one embodiment, unit dosage forms of carbachol and propranolol are provided either in separate containers or in a single container for administration to a patient, optionally in combination with a pharmaceutically acceptable carrier. For example, carbachol can be present in a pharmaceutically acceptable carrier in a dosage form for administration to a patient in an amount of about 5 to 150 μg/kg body weight of the patient, or in a total amount of from about 1 to 20 mg, or in a total amount of about 5 to 10 mg. The propranolol can be present in a pharmaceutically acceptable carrier in a dosage form for administration to a patient in an amount of about 0.01 to 0.07 mg/kg body weight of the patient, or in a total amount of about 1 to 10 mg, or in a total amount of about 1 to 8 mg, or in a total amount of about 1 to 5 mg. Carbachol is available commercially from Sigma Chemical Company, St. Louis, Mo.

Thus, in one aspect of the invention, there is provided a composition comprising an AV node blocker or a β-blocker, or a combination thereof, in a pharmaceutically acceptable carrier. The composition, may be provided for example as an aqueous solution, or in the form of a suspension or emulsion. Optionally, the composition may include a mixture of AV node blockers and/or a mixture of β-blockers. The composition may be provided in a form suitable for parenteral administration. In the embodiment wherein the composition comprises water, the water is preferably processed, for example by compression distillation, to ensure that it is sufficiently purified to be suitable for parenteral administration. Methods for making compositions of a quality suitable for parenteral administration are disclosed for example, in Gennaro, "Remington: The Science and Practice of Pharmacy," Mack Publishing Co., Easton, Pa. 1995, Vol. 2, Chapter 87, the disclosure of which is incorporated herein. In one embodiment, the composition is provided in a form suitable for administration to the cardiovascular system during a surgical procedure. In one embodiment, the AV node blocker is a cholinergic agent. In a preferred embodiment, the AV node blocker is carbachol. The pharmaceutically acceptable composition comprising the AV node blocker or β-blocker, or combination thereof, may be provided, for example in an aqueous solution, in a container, such as a vial, at a concentration suitable for direct administration to a patient, or may be diluted, for example with saline.

In one embodiment, a pharmaceutically acceptable composition comprising an AV node blocker, such as cholinergic agent, is provided, which may be used to permit local cardiac administration of the AV node blocker. In one embodiment, there is provided a pharmaceutically acceptable composition comprising carbachol, wherein the composition is suitable for parenteral administration. Preferably, the carrier is suitable for intracoronary administration. The carbachol may be provided in an aqueous carrier, such as water. In the composition, which optionally may be diluted prior to local cardiac administration, the concentration of carbachol may range, for example, from about 0.01 mg/mL to 2.55 mg/mL, e.g., about 0.1 to 1.0 mg/mL. In one embodiment, the composition may further comprise a β-blocker, such as propranolol, at a concentration, for example, of about 0.5 to 6 mg/mL, for example about, 0.5 to 3 mg/mL, or, e.g., about 1.0 to 2.0 mg/mL or about 1.0 mg/mL. If needed, the composition may be diluted to a concentration suitable for local administration to the heart, e.g., via an intracoronary bolus or infusion.

Pharmaceutically acceptable compositions also are provided including an AV node blocker, such as a cholinergic agent and/or a β-blocker that are suitable for direct local cardiac administration. In one embodiment, there is provided a pharmaceutically acceptable composition comprising carbachol, wherein the composition is suitable for direct local administration, for example, to a coronary vessel such as the right coronary artery. The carbachol is, for example, provided in an aqueous carrier, such as water. In one embodiment, the carbachol is provided in physiologic saline. In the composition, the concentration of carbachol may range, for example, from about 0.001 to 2.55 mg/mL, for example, about 0.01 to 2.5 mg/mL, or about 0.05 to 1.0 mg/mL, e.g., about 0.01 to 0.5 mg/mL, for example, about 0.05 mg/mL to 0.2 mg/mL, or e.g., about 0.1 to 0.2 mg/mL, or about 0.075 mg/mL. The composition may optionally further comprise a β-blocker, such as propranolol, at a concentration, for example, of about 0.05 to 6.0 mg/ml, for example, 0.05 to 3.0 mg/ml, or, e.g., about 1.0 to 2.0 mg/ml, or about 1.0 mg/mL. In this embodiment, the composition is suitable without dilution for local administration to the heart, e.g., via an intracoronary bolus or infusion.

In another aspect of the invention, there is provided a surgical kit including a container comprising a dosage of a cholinergic agent, such as carbachol. In one embodiment, a surgical kit is provided that includes a first container comprising a cholinergic agent and a second container comprising a β-blocker, wherein in one preferred embodiment, the cholinergic agent is carbachol and the β-blocker is propranolol. The containers may include respectively a preferred dosage form of the carbachol and of the propranolol. The first container may include carbachol in a pharmaceutically acceptable carrier, and the second container may include propranolol in a pharmaceutically acceptable carrier. Alternatively, the cholinergic agent and the β-blocker may be provided in a single container, optionally in combination with a pharmaceutically acceptable carrier. The kit may further include epicardial or endocardial pacing electrodes or any other disposable items associated with the pacemaker. The kit also may include a drug delivery catheter and associated disposable items.

Referring to the drawings where like numerals indicate like elements, drug delivery and pacing apparatus are shown in accordance with the principles of the present invention. The pacing system generally includes pacer, a switch box and an actuator, which preferably can be readily controlled by the physician to remotely control the pacer through the switch box. The pacing system will be described with reference to the example illustrated in FIG. 1. However, it should be understood that other configurations may be used.

Referring to FIG. 1, a pacing system configured in accordance with the present invention is shown. The illustrative system generally includes a pacer 18, a switch or control box 14, and an actuator, such as actuator 22 or 24. Pacer 18 may be a conventional ventricular demand pacer or dual chamber (atrial-ventricular) pacer. Leads 16 couple the output of pacer 18 to switch box 14 and leads 12 couple switch box 14 to the patent's heart. The latter may be achieved for example, either endocardially or epicardially. Switch or control box 14 preferably is configured so that when actuated, it delivers the pacing signals or output of pacer 18 to leads 12. Conductor or lead 20 couples remote actuator 22 to switch box 14. Although a conventional foot pedal type actuator is shown, it should be apparent from the foregoing and following discussion that other actuators such as handle held actuator 24 (shown in phantom) may be used. Further, as an alternative to epicardially or endocardially placed pacing leads, the leads may be transvenously delivered for coupling to the heart. In a further alternative, electrodes, such as transarterial electrodes, can be incorporated into the drug delivery catheter.

This pacing system of the present invention preferably provides to the surgeon remote control of the on/off pacing function only. All other parameters which are user selectable (rate, output, etc.) preferably are not remotely programmable but must be adjusted by using controls on the pacemaker.

Figure 1A:
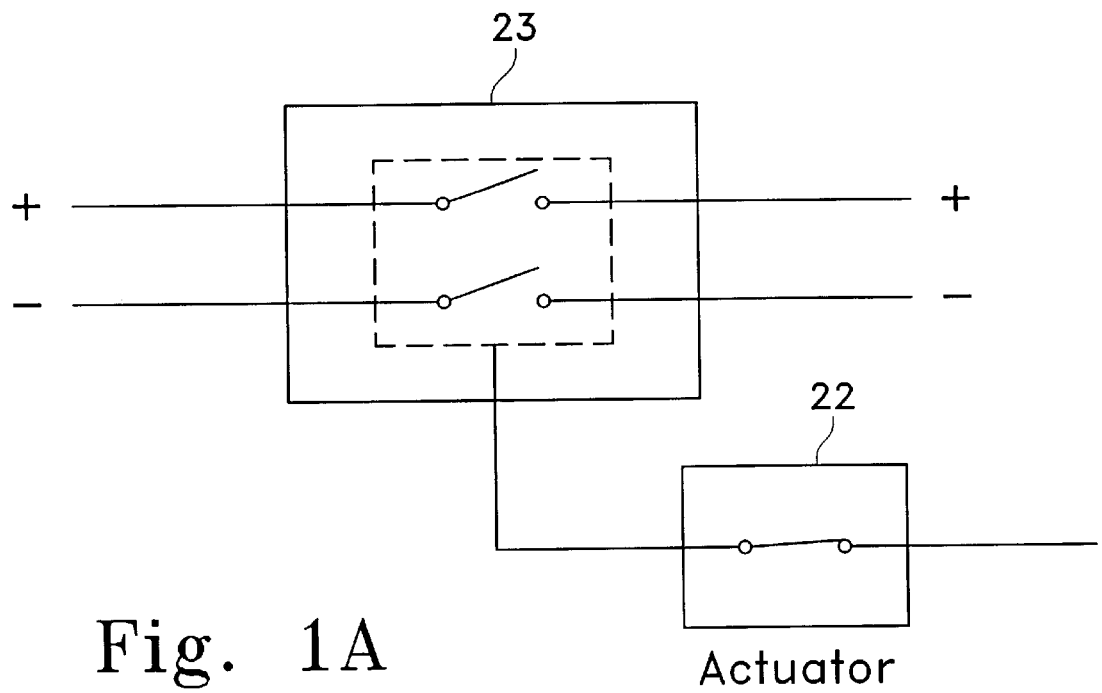
FIGS. 1A and 1B are circuit diagrams of a control switch and an actuator used in the pacing system of FIG. 1.
Figure 1B:
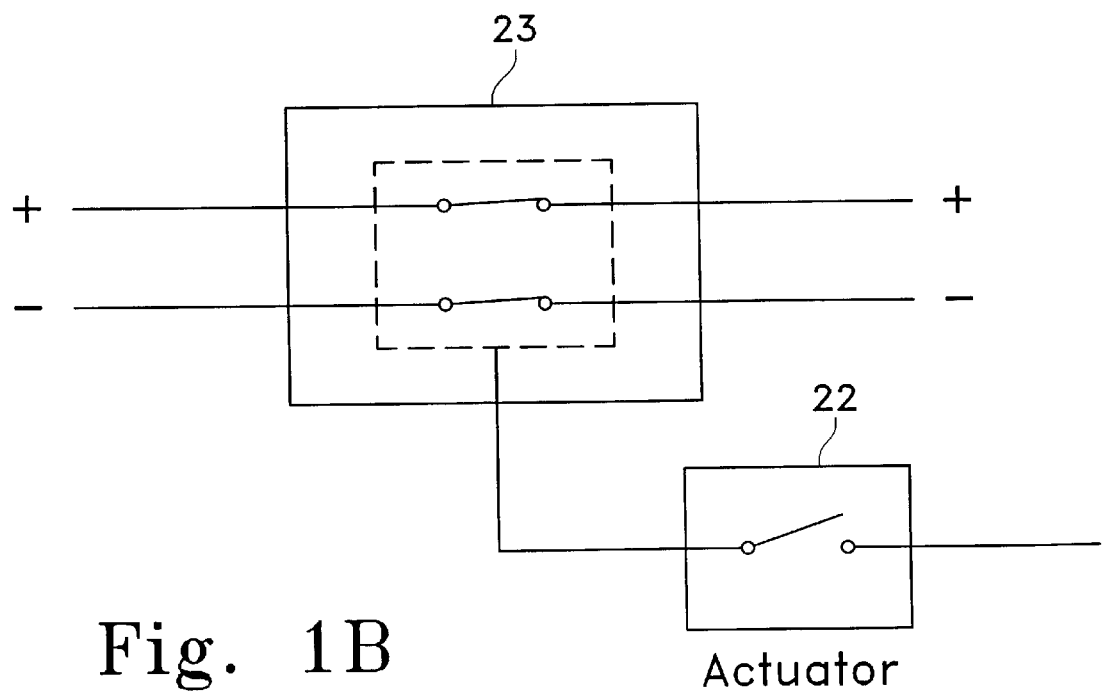

Referring to FIGS. 1A and 1B, circuit diagrams of the pacing system of FIG. 1 are shown. Switch box 14 includes an electrical or mechanical switch 23 to which actuator 22 couples. This coupling allows the switch to be energized or deenergized as would be apparent to one of ordinary skill. Preferably, foot pedal 22 is configured to be in an "Off" (electrically open) position when in its normal state and to be in an "On" (electrically closed) position to open switch 23 in switch box 14 and interrupt delivery of pacing signals to the heart when the pedal is depressed. Accordingly, if the power source to the pedal is interrupted, the heart will be paced. Alternatively, the foot pedal may be configured to be in an "On" position when in its normal state and to be in an "Off" position when the pedal is depressed.

Returning to FIGS. 1A and 1B, switch box 14 preferably is configured in a manner to allow the pacing signal to pass through the box, to leads 12 and, thus, to the patient while actuator 22 is in the "Off" position. As shown in Figure IA, the switch box's switch 23 opens when the actuator is activated (e.g., the foot pedal is depressed). This opening prevents the pacing signal from going to the patient. On the other hand, as shown in FIG. 1B, the switch box's switch 23 closes to again allow the pacing signal to pass through to the patient, when the actuator is released. Commercially available switch boxes and foot pedal actuators may be used. For example, a suitable switch box with foot pedal is the Treadlight 2, Catalogue No. T-91-S manufactured by Line Master Switch Corporation. This switch provides an open circuit when actuated as shown in FIG. 1A.

Safety features may be incorporated into the switch box. The first is a timer or override circuit, either programmable or factory set, that limits the time the switch or control box can interrupt the pacer. This circuit overrides the actuator, if the actuator should happen to be held down (i.e. in the "On" position) too long, i.e., longer than the preset maximum time. The override circuit may be set or configured to override the activator after an interval of time of about 0.1–60 seconds, more preferably about 5–30 seconds, or more preferably about 10–15 seconds.

A second safety feature is an indicator (visual and/or audible) that indicates the pacing signal is not being sent to the patient. A third safety feature is an indicator (visual or audible) that the pacing signal is going out from the control box to the patient, especially to signify the end of an interruption period (resumption of pacing). Preferably, the indicator or indicators are audible signals.

The control box could have additional features that may be more useful for the user than for safety. The first feature would be an indicator, preferably audible, preparing the user for the resumption of pacing. This could be a beeping tone that increases in frequency as the interruption period ends. Second, the control panel should be battery powered either by a disposable or re-chargeable battery. Other features include a control box that is preferably within 7"×10"×5", lightweight, less than 3 pounds, and easy to use with current pacer and pacing lead designs.

Figure 1C:
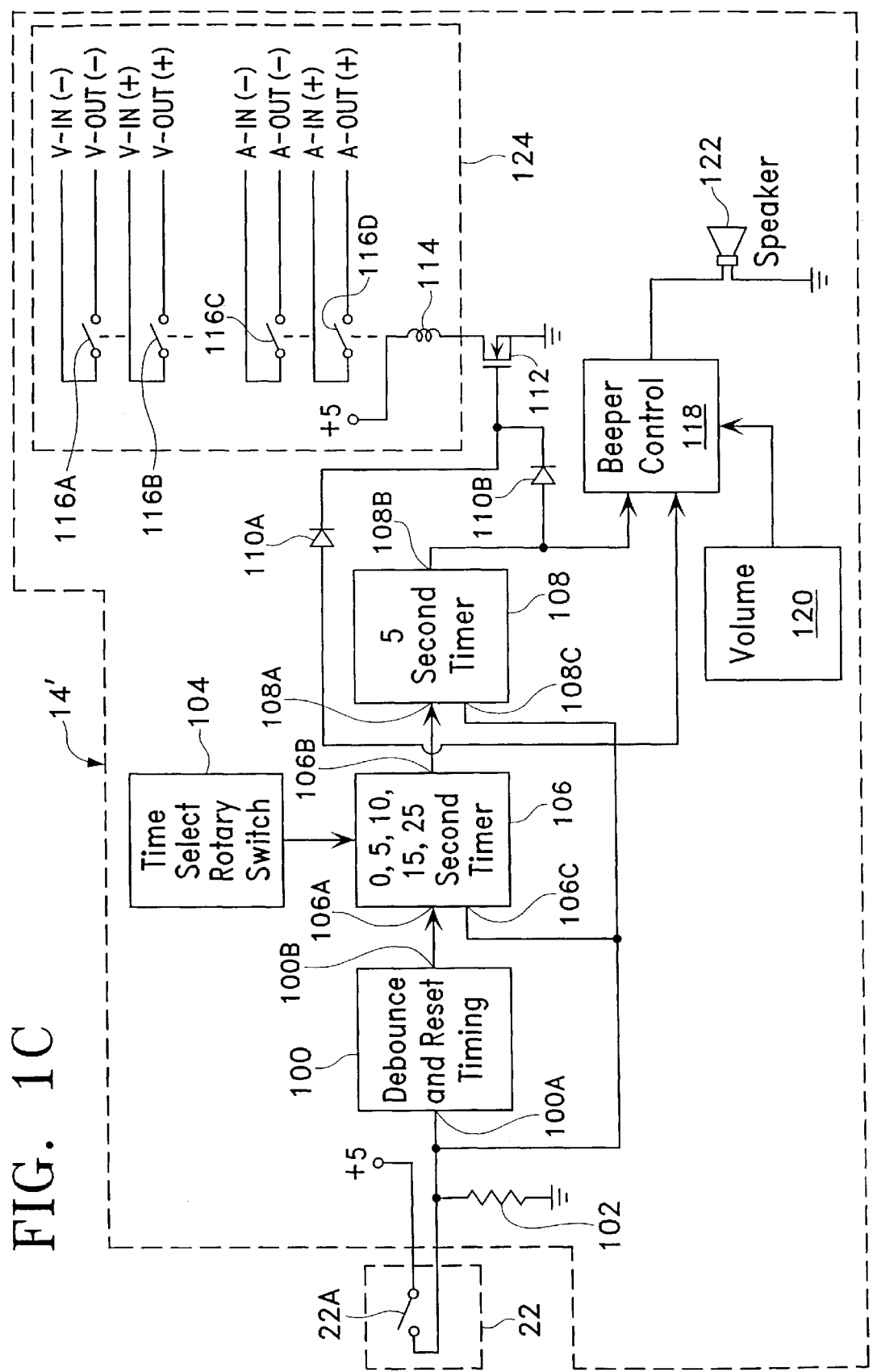
FIG. 1C is a schematic representation of a control box according to the present invention.

FIG. 1C presents one embodiment of the control box as schematically shown in FIGS. 1, 1A and 1B. As shown in FIG. 1C, a suitable control box 14' includes debounce circuit 100, pull-down resistor 102, timer select switch 104, first timer 106, second timer 108, diodes 110, transistor 112, inductive solenoid coil 114, switches 116, beeper control 118, volume control 120, and speaker 122.

Control box 14' uses debounce circuit 100 to generate a steady signal when mechanical foot pedal 22 is depressed. Debounce circuit 100 has an input terminal 100A and an output terminal 100B. The input terminal connects to pull-down resistor 102. This terminal also connects to the foot pedal switch 22A of foot pedal 22. When the foot pedal switch is open as shown in FIG. 1C (e.g., when the operator does not depress the foot pedal), the input terminal is pulled to ground through pull-down resistor 102. On the other hand, when the foot pedal switch closes (e.g., when the operator depresses the foot pedal), the input terminal connects to the power supply voltage source through the foot pedal switch 22 in order to receive the power supply voltage. In response to the power supply voltage provided by mechanical foot pedal 22, the debounce circuit generates a signal on its output terminal that it steadily maintains at one level (e.g., the ground level) until the foot pedal switch opens.

As shown in FIG. 1C, the output terminal 100B of the debounce circuit 100 connects to first timer 106. The voltage on this output terminal is usually in a first level (e.g., the power supply voltage) when the input to the debounce circuit is pulled to ground (i.e., when the foot pedal has not been depressed). However, this output terminal's voltage transitions to a second level (e.g., the ground voltage) when the input to the debounce circuit transitions to the power supply voltage (i.e., when the foot pedal has been depressed). As further described below, the voltage at the output terminal 100B in combination with the signal supplied to the reset pin 106C of the first timer circuit controls the operation of this timer circuit.

Control box 14' uses first and second timer circuits 106 and 108 in order to measure the lapse of a selected period of time. The amount of time selected on time select rotary switch 104 is the maximum amount of time that the physician can interrupt the supply of the pacing signal to the heart by depressing the foot pedal. Once the control box 14' determines, through the use of timers 106 and 108, that the maximum amount of time has expired, then the control box 14' overrides (i.e., ignores) the signal generated by the depressed foot pedal and resumes the supply of the pacing signal to the patient. The second timer counts the last five seconds in the selected period of time, while the first timer counts the remainder of time.

Both the timers 106 and 108 have reset pins (i.e., reset terminals) 1 06A and 108A that receive the signal supplied to input terminal 100A of debounce circuit 100. When the signal supplied to the reset pin of a timer is low (i.e., when the foot pedal has not been depressed), the timer enters its reset mode and resets its measured time value to its initial value. Each timer exits its reset mode and enters a standby mode when the signal supplied to its reset terminal is high (i.e., when the foot pedal has been depressed).

Also, each timer enters its operational modes when it receives a trigger signal at its input after it has entered its standby mode. Once the timers are in their operational modes, they start counting up or down to their expiration values when they receive an appropriate signal (e.g., a high voltage) on their input terminals 106A, 108A. First timer 106 receives its trigger signal from the output of the debounce circuit. Thus, the transition of the output of the debounce circuit from one state to another (e.g., goes from a high level to a low level) triggers the operation of the first timer 106. Once triggered, the first timer 106 starts to count towards its expiration value. The physician determines the expiration value of the first timer by operating the timer select switch 104, which connects to the first timer.

While the first timer operates (i.e., while it counts) and before it has reached its expiration value, the signal at this timer's output terminal 106B is at a first voltage level (e.g., the power supply level). The signal from output terminal 106B flows through diode 110A and is supplied to the gate of transistor 112 to turn ON this transistor. Transistor 112 can be any type of transistor. In FIG. 1C, this transistor is an NMOS device.

Once transistor 112 turns ON, it draws current from the power supply through the inductive solenoid coil 114. This coil serves as a relay (i.e., coil that when energized operates a mechanical switch). Thus, when current passes through the solenoid coil, it activates the relay which opens switches 116A–D of patient connect relay 124. When the relay is deactivated, switches A–D couple the signal from the pacer to the patient through leads 12.

Referring to the embodiment illustrated in FIG. 1C, switch 116A couples a ventricle inlet V-IN(−)) to a ventricle outlet (V-OUT(−)). Switch 116B couples a ventricle inlet (V-IN(+)) to a ventricle outlet (V-OUT(+)). Switch 116C couples an atrial inlet (A-IN(−)) to an atrial outlet (A-OUT(−)), while switch 116D couples an atrial inlet (A-IN(+)) to an atrial outlet (A-OUT(+)). The inlets are coupled to the pacer and the outlets are coupled to the patient. Referring to FIG. 1D, a schematic representation of an endocardial lead arrangement between the control box and the right atrium of a patient is shown, together with the coupling between the control box and the pacer. An actuator may be coupled to the control box as described above. The inlets (A-IN(−), A-IN(+)) may be coupled to the pacer 18 adapter cables and the outlets (A-OUT(−), A-OUT(+)) may be coupled to the patient with leads as shown in the drawing and as would be apparent to one of ordinary skill. Specifically, one lead may be coupled to positive terminal 140, which is in the form of a ring, and the other lead may be coupled to a negative terminal 142, which may have a generally hemispherical configuration. A similar arrangement can be used to couple the control box to the right ventricle. Although an endocardial lead configuration is shown in FIG. 1D, epicardial leads as shown in FIG. 1E may be preferred. Specifically, epicardial leads, which may be sutured to the heart (e.g., right atrium) as shown in FIG. 1E and generally designated with reference character "S", generally are preferred in open chest procedures since they can be readily sutured to the heart. Again, a similar arrangement can be used to couple the control box to the right ventricle.

Although the patient connect relay 124 is shown as a dual chamber pacing system, it should be understood that single chamber pacing systems can be used to pace the ventricle as would be apparent to one of ordinary skill in the art (e.g., by only using switches 16A and B shown in FIG. 1C).

The output of the first timer is also supplied to a beeper control circuit 118, which controls the output of a speaker 122. Hence, when the first timer's output is active (i.e., its at a first voltage level, such as the power supply level), it turns ON the beeper control circuit, which in turn generates a first audible signal through speaker 122.

When the first timer expires (i.e., when it has reached its expiration value), the signal at its output terminal transitions from the first voltage level to a second voltage level (e.g., transitions from the power supply level to ground level). The first timer then enters its standby mode, where it will stay until it is reset by the opening of the foot pedal switch.

The second timer has an edge detector (e.g., a negative edge detector) that detects this transition. Once it detects this transition, the second timer transitions into its operation mode, and thereby starts to count towards its expiration value. The second timer's expiration value is set at five seconds.

While the second timer is in its operation mode and has not reached its expiration value, the signal at its output terminal is at a first voltage level (e.g., the power supply level). In turn, diode 110B supplies this signal to the gate of transistor 112, and thereby keeps this transistor ON. While transistor 112 is ON, it continues to draw current through the coil 114, which, in turn, keeps switches 116A–D, which control delivery of the pacer signal to the patient, open.

The output of the second timer is also supplied to a beeper control unit. Hence, when this output is active (i.e., its at a first voltage level, such as the power supply level), it turns ON the beeper control unit, which in turn generates a second audible signal through speaker 122.

Finally, it should be noted that the output of the timers resets to the second voltage level (e.g., ground) whenever the foot pedal switch opens and the timers are reset. This resetting operation overrides the counting operation of the timers. Thus, if the timers are in the process of counting, the opening of the foot pedal makes these timers stop counting and reset. Any suitable timers may be used such as 555 timers manufactured by National Semiconductor (Santa Clara, Calif.).

As an alternative to foot pedal 22, a conventional needle holder 24 can be used to control the pacer switch box. In this case, the needle holder preferably is of the standard Castro-Viejo variety. However, any other manual switch actuator operable by the surgeon for opening and closing the switch in switch box 14 on demand can be used in accordance with the invention to electrically connect and disconnect pacer 18 with pacing leads 12. Thus, the actuator can be incorporated in or on one of the surgeon's instruments, such as surgical site retractor, or any other location easily and quickly accessed by the surgeon.

Any conventional pacer suitable for ventricular demand pacing and having external leads that can be electrically coupled to a switch box 14 may be used. An example of such a suitable pacer is the Medtronic model 5330 or 5375, Demand Pulse Generator manufactured by Medtronic Inc. (Mpls, Minn.)

It should be understood that although a particular pacing configuration is shown, other configurations may be used. For example, the pacer and switch box may be combined in a single unit. If the switch box is incorporated in a pacer (i.e., pacemaker), specifications of the pacemaker should be similar to currently manufactured external pacemakers (e.g., Ventricular or atrial-ventricular sequential; Rate range: 30 to 180 ppm (pulses per minute), continuously adjustable or in increments of 1 ppm; Output current range: 0.1 to 20 mA; Sensitivity range: 1.0 mV(maximum) to asynchronous; Pulse width: 1.8 ms maximum).

Pacer 18 preferably is an extracorporeal pacer and differs from implantable pacemakers in the following ways. Pacer 18 typically will be in excess of 400 grams, can use replaceable (battery life of approximately 500 hours) or rechargeable batteries (9v), may be line power designed to last several years, and need not be constructed with a biocompatible exterior shell or be hermetically sealed.

Further, the pacing system may be configured to synchronize activation and deactivation of the patient's ventilator (not shown) with pacing. For example, the control box may be configured for coupling to a ventilator so that pacing and ventilator signals are simultaneously delivered to the patient leads 12 and the ventilator when the actuator is in a first state (e.g., when the foot pedal is released). In this example, the pacing and ventilator signals are simultaneously interrupted when the actuator is in a second state (e.g., when the foot pedal is depressed). The synchronization of pacing with a ventilator may minimize or eliminate unwanted heart motion associated with a patient's breathing with a ventilator.

Figures 2, 2A:
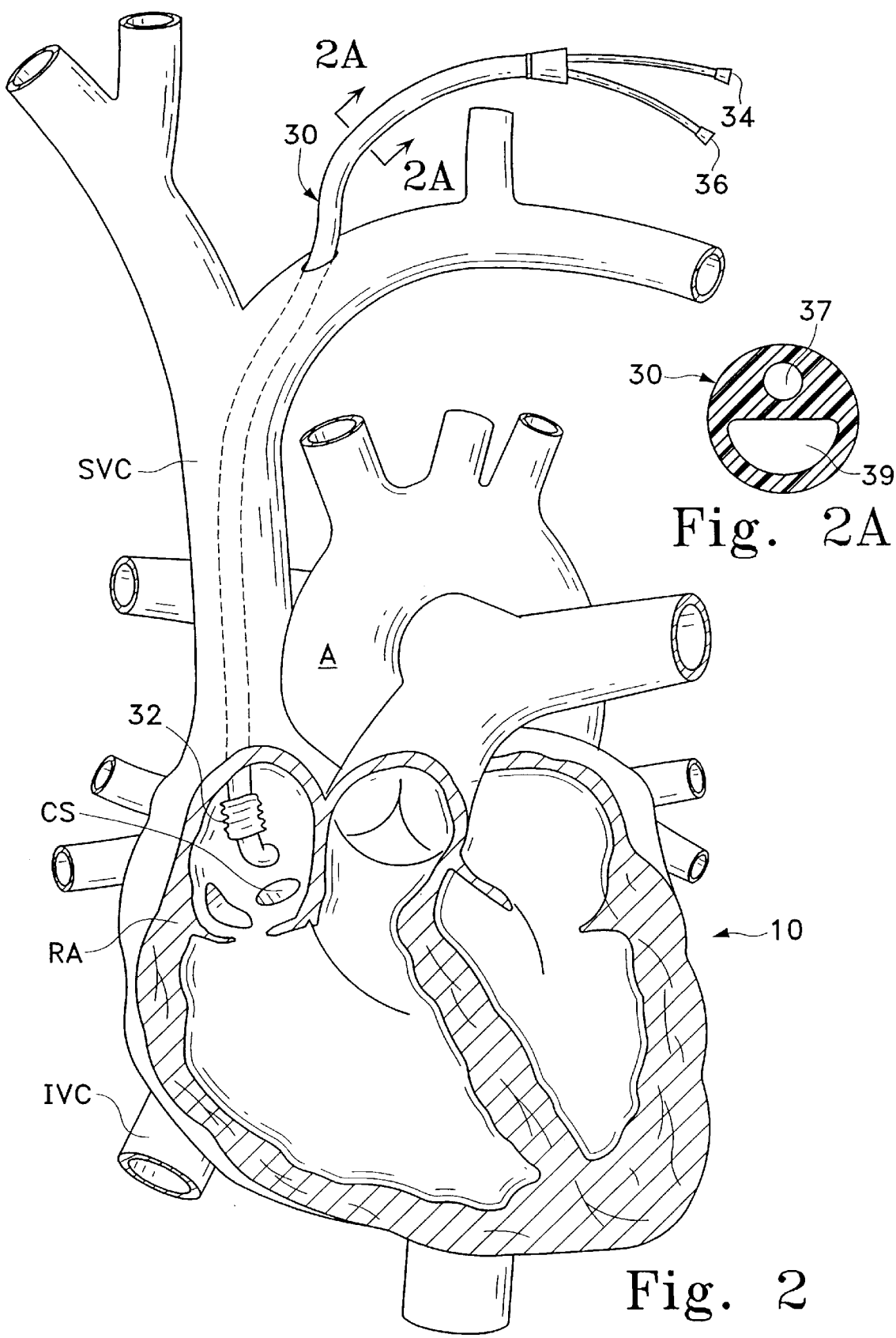
FIG. 2 illustrates a drug delivery catheter prior to insertion into the coronary sinus in accordance with the invention.
FIG. 2A is a sectional view of the catheter of FIG. 2 taken along line 2A—2A.
Figure 3:
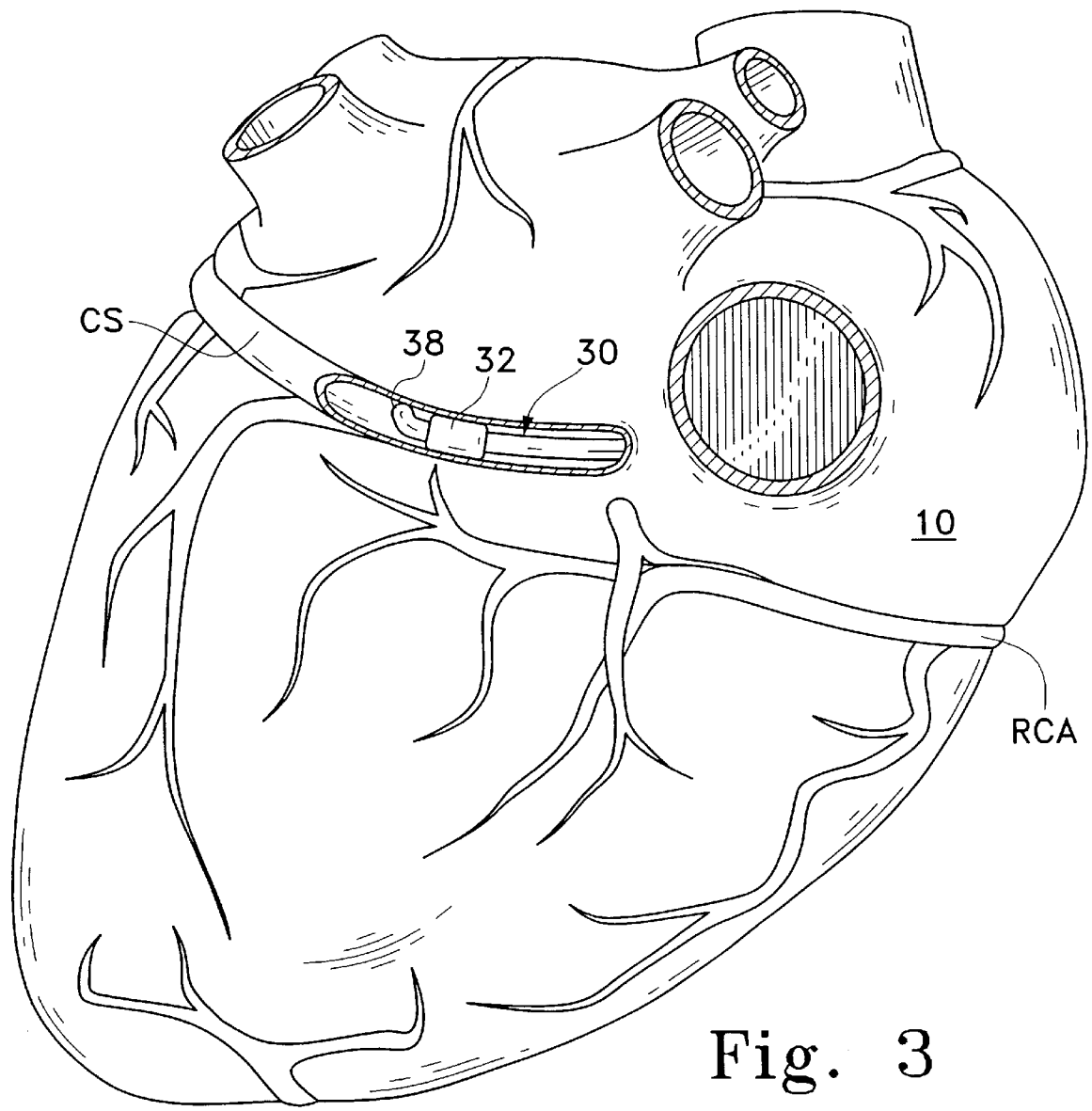
FIG. 3 illustrates placement of the distal end portion of the catheter of FIG. 2 in the coronary sinus.
Figure 3A:
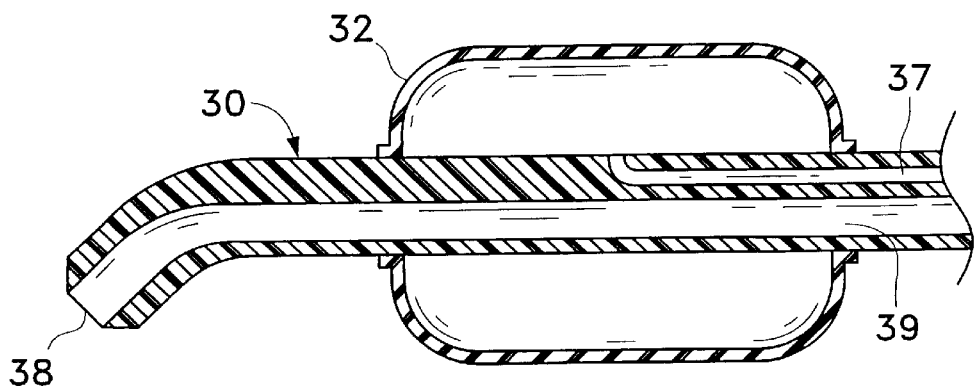
FIG. 3A is a sectional view of the distal portion of the catheter of FIG. 3.
Figure 4:
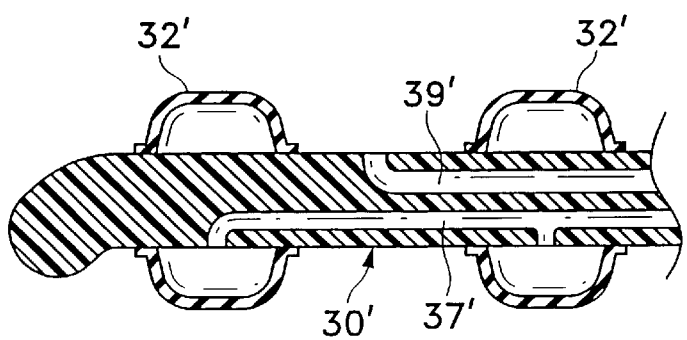
FIG. 4 illustrates another coronary sinus catheter configuration.
Figure 5:
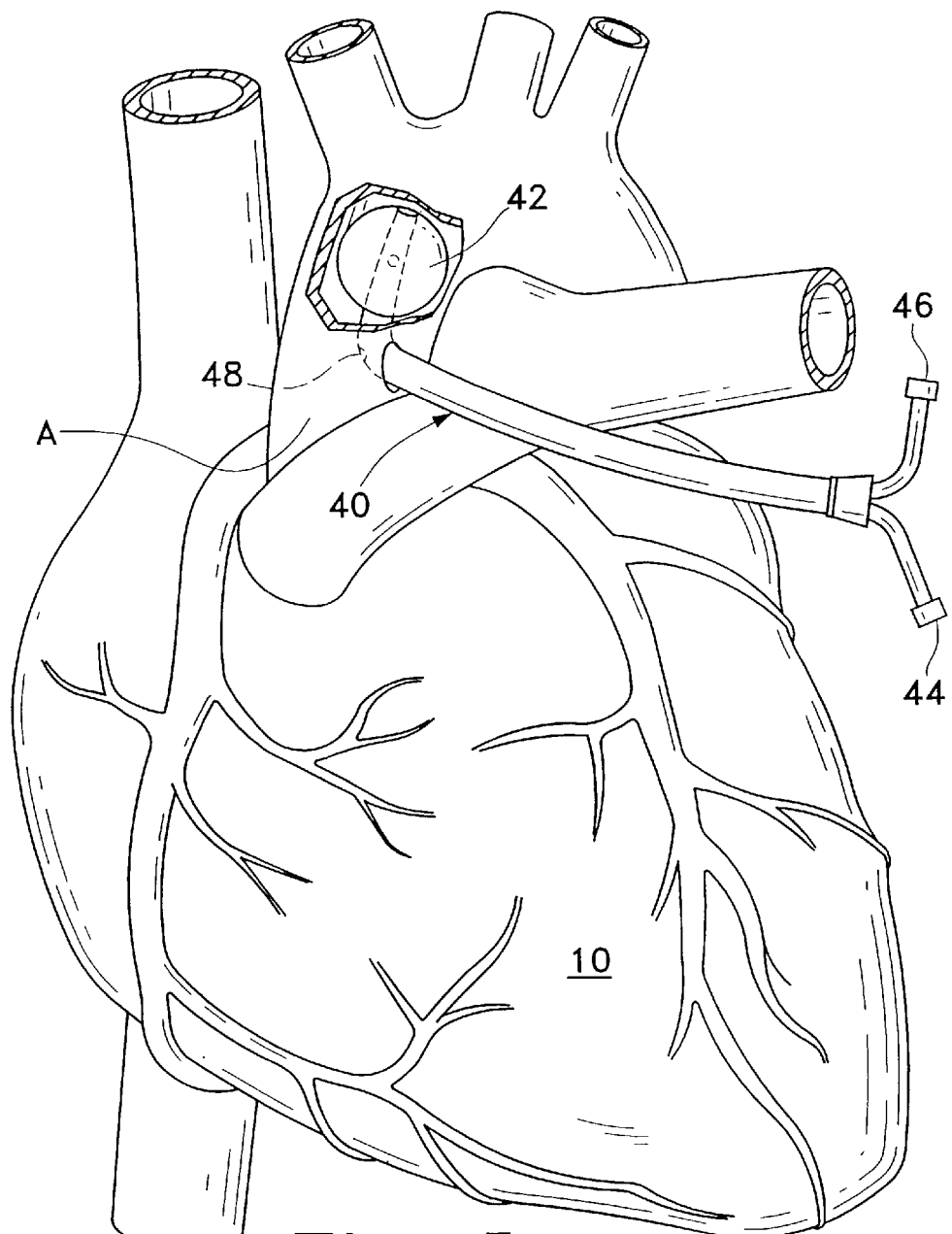
FIG. 5 depicts a drug delivery catheter positioned for intra-aortic drug delivery in accordance with the present invention.
Figure 6:
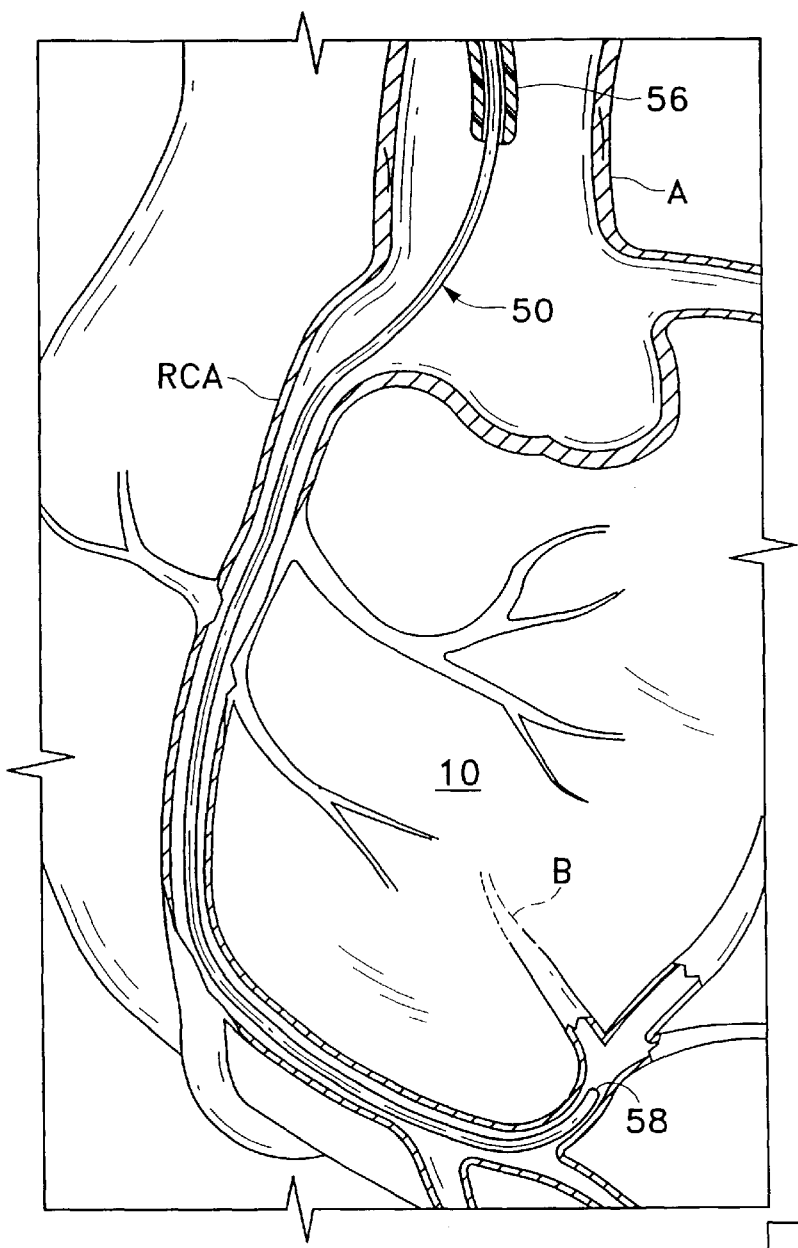
FIG. 6 illustrates a drug delivery catheter positioned for drug delivery local to the AV node branch in accordance with the present invention.
Figure 7:
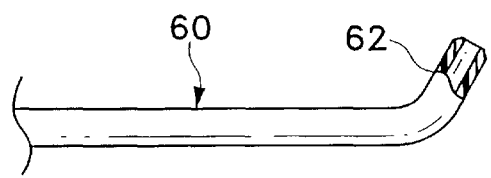
FIG. 7 illustrates another embodiment of the catheter of FIG. 6 showing a curved distal end portion for directing fluid toward the AV node.

With an understanding of the pacing system in hand, drug delivery according to the principles of the invention will be described with reference to FIGS. 2–7. Generally, FIGS. 2 and 3 show delivery into the coronary sinus (FIG. 4 shows an alternative balloon configuration); FIG. 5 shows intra-aortic delivery; and FIGS. 6 and 7 show delivery through the right coronary artery. Discussion of a further delivery procedure in accordance with the present invention, intraventricular injection, also will be provided.

Coronary Sinus Injection

Referring to FIGS. 2, 2A, 3, and 3A, a coronary sinus delivery catheter 30 is shown for local drug administration into the coronary sinus (CS) according to the present invention. Coronary sinus delivery catheter 30 preferably is a medium-diameter, e.g. about 6–8 French, single or dual lumen, flexible catheter. The tip of catheter 30 may be curved slightly to give a so-called hockey-stick appearance as shown in the drawings. This configuration facilitates, for example, introducing the catheter into the coronary sinus from the atrium as shown in FIG. 2 where the distal tip is shown prior to introduction into the coronary sinus. A low-pressure balloon 32 of up to about 2 cm in diameter is located near the tip of the catheter. Two ports 34, 36 are present at the proximal portion of catheter 30 for balloon inflation and drug injection, respectively. Catheter 30 further includes inflation lumen 37 and drug delivery lumen 39 (FIGS. 2A and 3A) which fluidly couple ports 34 and 36 to balloon 32 and delivery or discharge opening 38.

Any of three catheter lengths may be used depending on whether the catheter is introduced into the coronary sinus: (A) through the right atrium or atrial appendage; (B) via the internal jugular or subclavian vein; or (C) via the femoral vein. A guidewire (not shown) is used to facilitate transvenous placement, and a stiffer wire obturator (not shown) is provided for catheter insertion through the right atrial appendage.

Access to the right atrial appendage (approach A) requires an operative approach through the right chest or through the mediastinum. A plegeted pursestring suture (e.g. 4/0 polypropylene), which is conventional in the art, is placed on the right atrium (RA) or atrial appendage, and catheter 30 is secured in place with a Rumel-tourniquet. The transvenous approaches (approaches B and C) require expertise in coronary sinus cannulation over a guidewire using fluoroscopic or echocardiographic guidance. The internal jugular or subclavian approach accesses the coronary sinus via the superior vena cava (SVC) as shown in FIG. 2. The femoral vein approach accesses the coronary sinus via the inferior vena cava (IVC).

After the catheter is placed in the coronary sinus using any of the three approaches described above, the guidewire or obturator, which was used to introduce the catheter into the coronary sinus, is removed. Injection port b 36 is then connected to a three-way stopcock (not shown) for intermittent measurement of coronary sinus pressure and administration of the composition(s) provided in accordance with the present invention. With inflation of the low-pressure balloon within the coronary sinus (FIG. 3), a right ventricular pressure wave form is observed. The inventive composition(s) is then administered as a bolus injection through drug injection port 36 so as to be delivered at the delivery port 38. Coronary sinus pressure during bolus injection generally should not exceed about 30 mm Hg. Alternatively, the composition(s) may be administered as a bolus injection followed by continuous infusion or as a continuous infusion alone. Balloon inflation may be rapid inflation/deflation balloon synchronized with the electrocardiogram (ECG). Alternatively, the coronary sinus may be occluded, partially or completely, for a period of about one or two hours. Balloon 32 may have a much thinner wall construction than balloon 42 (discussed below) because it need not expand against arterial pressure. Previously placed pacing leads 12 permit ventricular pacing during drug induced ventricular asystole. Removal of the catheter simply requires deflation of the balloon and closure of the atriotomy with the pursestring suture.

Referring to FIG. 4, another coronary sinus catheter configuration is shown. Catheter 30' is provided with laterally spaced balloons 32' which are fluidly coupled to inflation lumen 39'. Drug delivery lumen 37' opens in a region between the balloons.

Intraventricular Injection

Another drug administration approach is intraventricular injection into the left ventricle via a catheter (not shown). With this approach, the catheter may be delivered in retrograde fashion through the arterial system, aorta and through the aortic valve into the left ventricle. In the alternative, a catheter or cannula may be inserted directly into the left ventricle (preferably the apex) through a hole made by the surgeon. In a further alternative, a needle may be inserted directly into the left ventricle.

Aortic Root Injection

Another drug administration approach is injection of drug into the aortic root with, for example, an intra-aortic delivery catheter 40 as shown in FIG. 5. This permits direct aortic administration of compositions in accordance with the invention during diastole while providing ventricular support analogous to an intra-aortic counterpulsation device. Catheter 40 preferably is a dual lumen catheter provided for rapid inflation and deflation of a durable, low-pressure balloon 42 arranged to inflate in synchronization with heart beat (e.g., electronically synchronized with ECG "P" waves so that balloon 42 inflates during diastole and deflates just before systole). Importantly, complete occlusion of the aorta by the catheter balloon 42 is not required for proper functioning of the device. Thus, risk of injury to the aortic wall, for example, the aortic dissection, is minimized. As in the embodiment discussed above, a balloon inflation port 44 and a drug injection port 46 are provided. Catheter 40 has drug delivery and inflation lumens similar to catheter 30 with the exception that the drug delivery lumen in catheter 40 terminates with a discharge opening 48 proximal to balloon 42 this configuration facilitates delivery of drugs in the vicinity of the coronary arteries. Catheter 40 may be inserted through a hole made by the surgeon in the wall of the aorta as shown in FIG. 5, for example, or endovascularly delivered via a percutaneous catheter insertion technique (e.g., the Seldinger technique) in the femoral artery. However, if a catheter is desired to be delivered in a retrograde fashion through the arterial system (e.g. femoral artery and the aorta), the balloon and lumen configuration of catheter 30 or 30', for example, is preferred. The balloon diameter may be larger to correspond with the larger size of the aorta and the balloon walls also may be constructed to withstand the greater pressures in the aorta.

Returning to FIG. 5, which illustrates placement of catheter 40, a pursestring suture (not shown) is placed on the aortic root and catheter 40 is inserted into the ascending aorta and secured with a Rumel tourniquet. The intra-aortic balloon is inflated during diastole and deflated during systole, using the patient's ECG signal for synchronization. Drug delivery is given with a bolus infusion and/or continuous infusion. With drug induced ventricular asystole, the heart is electrically paced, as detailed hereinbelow, permitting continued intra-aortic counterpulsation. When the accompanying procedure is a coronary artery bypass procedure, catheter 40 is removed after the distal anastomosis is completed. Then, a partially occluding clamp is placed on the aorta, and the aortitomy may be used for the proximal aortosaphenous anastomosis. Alternatively, the catheter 40 may be removed and the aortic pursestring simply tied.

Direct Infusion Into Right Coronary Artery

Another drug administration approach is direct infusion into the right coronary artery (RCA). This approach advantageously delivers drug more local to the AV node than the approaches described above. Other methods are generally less efficient because when mixed in the aorta, ventricle, or other parts of the cardiovascular system, significant drug dilution occurs by the time it reaches the AV branch of the RCA.

This approach can be achieved by either injection into the proximal or ostial portion of the RCA, by use of a guide catheter or drug delivery catheter, or by injection just proximal to the branch perfusing the AV node (AV node artery) by means of a drug delivery catheter positioned in the RCA as shown in FIG. 6. Alternatively, the drug delivery catheter can be positioned directly in the AV node artery through the RCA to delivery the drug more locally to the AV node. The catheter may be introduced into the coronary artery via the arterial system (femoral, radial, subclavian) with a larger diameter coronary guiding catheter. In cases of a left dominant system anatomy or occluded RCA, the catheter may be used in a similar fashion to deliver the drug into the left coronary artery to, for example, the circumflex branch.

Referring to FIG. 6, an exemplary catheter design is shown in the drawings. Catheter 50 is a small diameter (for example, about 3–4 French) single lumen catheter with a drug delivery opening 58 located at the distal end of the catheter. to provide selective coronary artery drug delivery. By avoiding the need for a separate channel for balloon inflation, catheter 50 maximizes the volume of catheter lumen dedicated to drug delivery while minimizing catheter diameter.

In use, catheter 50 is introduced into the right coronary artery under fluoroscopic guidance through a larger diameter (6–8 French) coronary guiding catheter 56, which is positioned at the ostium, and over a guidewire which is placed distally in the RCA.

After appropriate positioning of the catheter tip, just proximal to or within the take-off of the artery to the atrioventricular node branch (B) the guiding catheter is pulled back from the ostium of the RCA to provide blood flow to the RCA, the guidewire is removed, and a bolus dose is given. Alternatively, a continuous infusion of drugs can be administered into the distal right coronary artery. Coronary catheter 50 is small enough that blood flow is not significantly impeded to the RCA.

Figure 8:
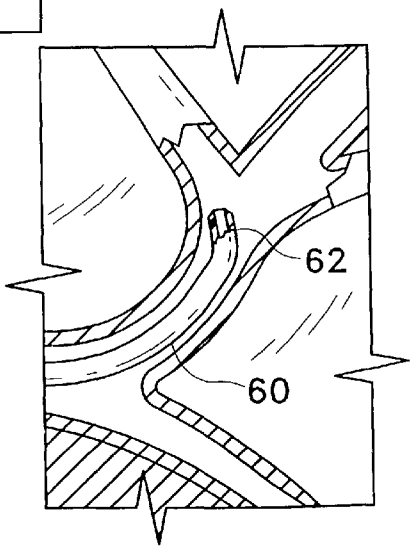
FIG. 8 depicts the catheter of FIG. 7 with its bent distal end portion directed toward the AV node branch.

Referring to FIGS. 7 and 8, another embodiment for the coronary delivery catheter is shown. Catheter 60 is the same as catheter 50 with the exception that catheter 60 has a bent distal end portion 62. Catheter 50 or portion 62 can be positioned within the branch (B) to the AV node. The bent distal end configuration minimizes or eliminates the possibility of the catheter entering the branch going down a posterior left ventricular branch.

Although particular drug administration routes have been described, it should be understood that other routes may be used including, without limitation, needle injection into the aorta, needle injection into the AV node, and trans-epicardial absorption (e.g., a trans-myocardial patch which slowly releases pharmaceutical agents into the myocardium).

Pacing

Prior to drug delivery, the heart is prepared for cardiac pacing as discussed above. In general, leads 12 may be temporarily affixed to the right ventricle of the heart such as by suturing or other manner as would be apparent to one of skill in the art. Drugs are administered to the heart through, for example, any one of catheters 30, 40, 50 or 60 to induce ventricular asystole. Pacing of the heart is established and maintained. The pacing can be transiently interrupted by temporarily deactivating the pacemaker using, for example, foot pedal 22. When the foot pedal is in its deactuated, raised position, the switch in the pacer switch box is closed, and current flows from the ventricular demand pacer 18, through the switch box 14 and the pacing wires 12 to the heart 10 without impediment. During this time, the heart preferably is paced at a rate between 90 to 110 beats/minute. When complete heart block is necessary, to enable a surgical procedure to be performed, pacing is disabled by depressing the foot pedal. In the illustrated and currently preferred embodiment, this opens the switch in pacer switch box 14, stopping the current flow from pacer 18 to pacing leads 12. Since no current reaches the heart while the foot pedal is depressed, ventricular asystole occurs, thus allowing precise suturing or other manipulative procedures to be performed. Once, e.g., a suture has been applied, the pacer may be reactuated by releasing the foot pedal, thereby to reestablish the electrical connection between the pacer 18 and the pacing wires 12 and resuming pacing of the heart at the prescribed rate until another precise manipulation is required. By providing a surgeon-controlled device, such as with a foot pedal, remote from the pacer for controlling the pacer, the surgeon can have complete and immediate control over when pacing is interrupted, even though the surgeon also has surgical instruments in his or her hands. This allows the surgeon to coordinate precisely the pacing of the heart to the manipulative step, thereby minimizing unnecessary and undesired cardiac arrest.

The pacer control box also may be configured to control interruption of a patient's ventilator so that the pacing may be synchronized (e.g., the actuator activates pacing and ventilating equipment (not shown) simultaneously and deactivates pacing and the ventilating equipment simultaneously). Thus, the switch box can be electrically coupled to a ventilator so that when the foot pedal described above is depressed pacing and ventilation are deactivated and when it is released, pacing and ventilation resume. This arrangement may eliminate some small motions of the heart associated with a patient's breathing during a surgical procedure.

As noted above, the methods and compositions of the invention are useful for any procedure which requires controlled temporary complete heart block and suppression of ventricular escape beats. More specifically, the methods, compositions and systems of the present invention may provide a significant clinical benefit and improve the clinical outcomes of a variety of therapeutic and diagnostic medical and surgical procedures which would benefit from a transiently arrested heart, the elimination of movements associated with pulsatile blood flow, or bleeding. Some of the examples of procedures discussed above are further discussed in more detail below.

Abdominal (or Thoracic) Aortic Aneurysm (AAA) Medical Procedures

The compositions, apparatus, systems and methods for heart rate and rhythm control management described herein can be used, for example, to assist in the deployment of prostheses during the repair of thoracic or abdominal aortic aneurysms.

An aortic aneurysm generally is an abnormal widening, stretching or ballooning of the thoracic or abdominal portion of the aorta, which is the major artery from the heart which delivers blood to the major organs of the body. The thoracic and abdominal portions of the aorta represent the upper, arched portion and lower, abdominal portion of the aorta, respectively. The exact cause of aneurysm is unknown, but risks include atherosclerosis and hypertension. A common complication is ruptured aortic aneurysm, a medical emergency in which the aneurysm breaks open, resulting in profuse bleeding. Aortic dissection occurs when the lining of the artery tears and blood leaks into the wall of the artery. An aneurysm that dissects is at even greater risk of rupture.

Generally, when an abdominal or thoracic aortic aneurysm reaches a size of about 5 cm, surgical intervention is necessary. To repair an abdominal or thoracic aortic aneurysm by intraoperative procedure, the thoracic cavity can be accessed by a midline or retroperitoneal incision in the case of an open procedure, or by percutaneous access in a minimally invasive endograft procedure, and a prosthetic graft is used to isolate the aneurysm from blood flow and pressurization, thus precluding aneurysm expansion and minimizing the risk of rupture.

Using the methods and compositions disclosed herein, minimally invasive endovascular repair procedures can be performed while minimizing the pulsatile flow of blood, movements associated with arterial pulsations, and/or bleeding, which make accurate deployment of aortic prostheses extremely difficult. Inaccurate deployment of aortic prostheses can lead to inadequate sealing of the aneurysm which can cause further aneurysm expansion due to blood flow around the graft, and/or inadvertent blockage of collateral vessels supplied by the aorta, for example, such as the renal arteries. The disclosed methods described can provide enhanced accuracy, for example, with respect to location and orientation, in the placement of the prostheses within a region of a patient's aorta having an aneurysm or other diseased or damaged condition therein, by overcoming and/or controlling the pulsatile movement of the stent graft deployment system.

Although the techniques of the present invention can be used to facilitate both open chest and minimally invasive closed chest abdominal or thoracic aortic aneurysm procedures, the following illustration describes only an endovascular minimally invasive repair procedure which is less traumatic to the patient than an open-chest procedure. One of ordinary skill in the art, however, will appreciate that the techniques disclosed can be readily applied to open chest procedures as well in which access to the thoracic cavity is achieved through a midline partial or median sternotomy, a mini-thoracotomy incision, or a retroperitoneal incision, for example.

Referring now to FIGS. 9A–9D, a system is schematically illustrated for inducing reversible ventricular asystole of the heart during a closed-chest abdominal or thoracic aortic aneurysm repair procedure.

In one embodiment, a patient is anesthesized and generally prepared for surgery in a conventional manner. With the patient in the supine position as shown, a drug delivery catheter 210 such as a Target Therapeutics Tracker™ Catheter (Boston Scientific, Natick, Mass.), Ultrafuse X Catheter (Scimed Corporation, Minneapolis, Minn.), or the novel catheter apparatus disclosed in co-pending patent application Ser. No. 09/276,312 entitled "Controllable Infusion Hole Catheter" and filed on Mar. 24, 1999, now abandoned the disclosure of which is incorporated herein by reference, is preferably subcutaneously inserted into a brachial or radial artery 264 in the arm using known techniques such as a direct cut-down or a percutaneous technique such as the Seldinger technique. Alternatively, the drug delivery catheter may also be percutaneously inserted from other peripheral vascular access points such as femoral or iliac artery 250, 252 in the groin area, or a carotid or subclavian artery 267 in the neck area of the patient.

A guidewire (not shown) is first inserted into the brachial or radial artery 264 and advanced toward the heart 258 under fluoroscopic guidance through the brachiocephalic artery 265 and thoracic aorta 256 until the distal end of the guidewire is in the coronary ostium of the right (or left) coronary artery (not shown in the drawing FIGS. 9A–D for clarity), as illustrated, for example, in FIG. 6. Drug delivery catheter 210 can then be positioned over the guidewire, introduced into brachial or radial artery 264, and advanced over the guidewire through the brachiocephalic artery 265 and thoracic aorta 256 and into the coronary ostium.

Alternatively, a guide catheter (not shown) can be used to facilitate positioning of the drug delivery catheter 210 into the coronary ostium of the right (or left) coronary artery. Where a guide catheter is employed, the guide catheter will be retracted from the ostium of the right (or left) coronary artery into the aorta following placement of the drug delivery catheter in the ostium. The guidewire can then be advanced to a suitable drug delivery location within the right coronary artery, for example proximal to the AV node artery, and the catheter tip advanced over the guidewire and positioned at the drug delivery location within the right coronary artery as shown, for example, in FIGS. 6 and 8 described herein.

The at least one discharge opening (not shown) of drug delivery catheter 210 is preferably positioned within about 8 cm from the AV node artery, for example about 1 to 3 cm proximal to the AV node artery, to minimize drug dilution to collateral vessels. As an alternative or supplement to fluoroscopic imaging, ultrasonic echocardiography may be used by, for example, positioning an echocardiographic transducer in the esophagus. The position of the drug delivery catheter 210 within the right coronary artery can be confirmed using fluoroscopic (or ultrasonic) techniques.

Figure 9A:
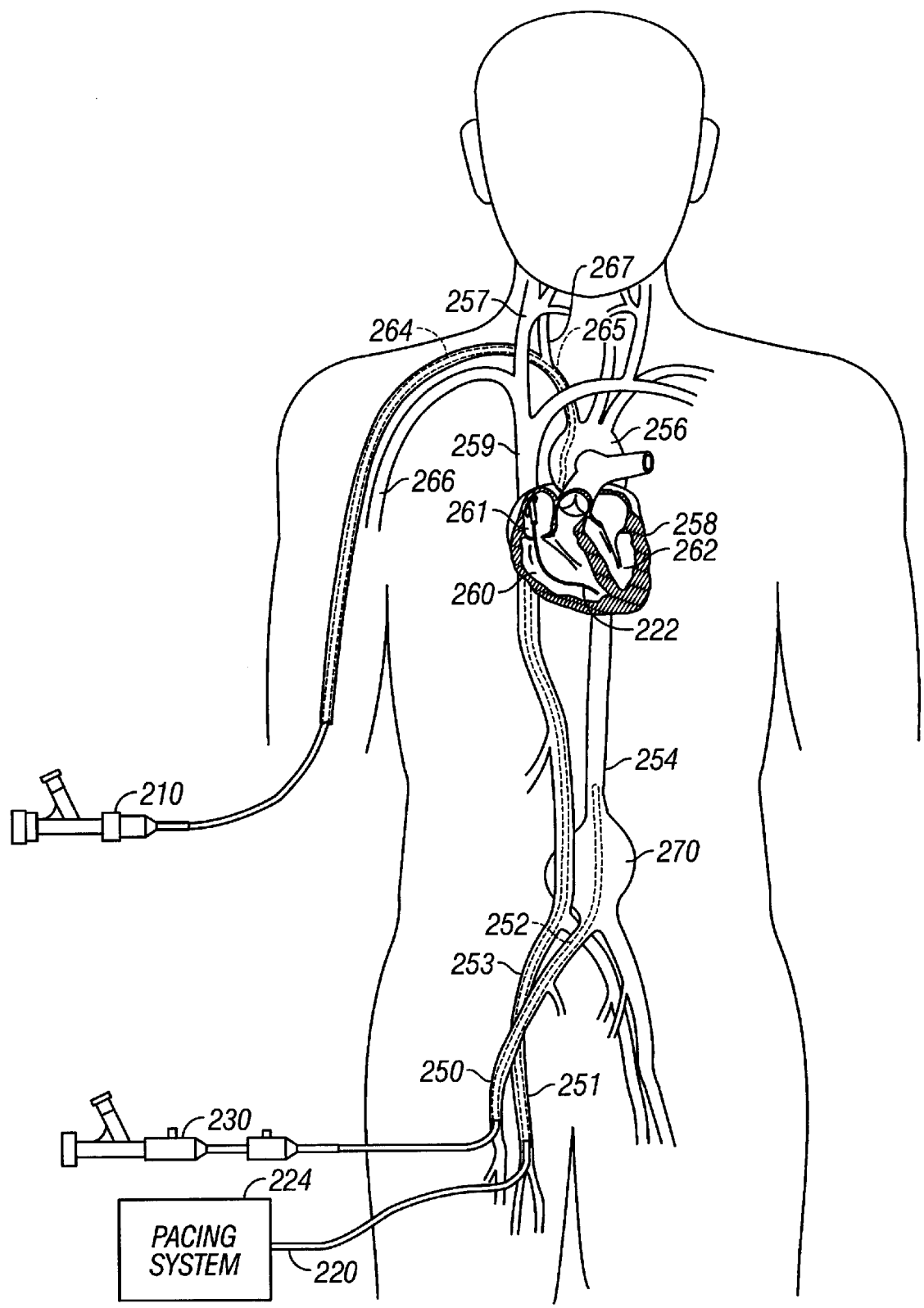
FIG. 9A diagrammatically illustrates an endovascular aortic prosthetic delivery system in accordance with the invention, illustrating prosthetic and drug catheters and pacing system arrangements.
Figure 9B:
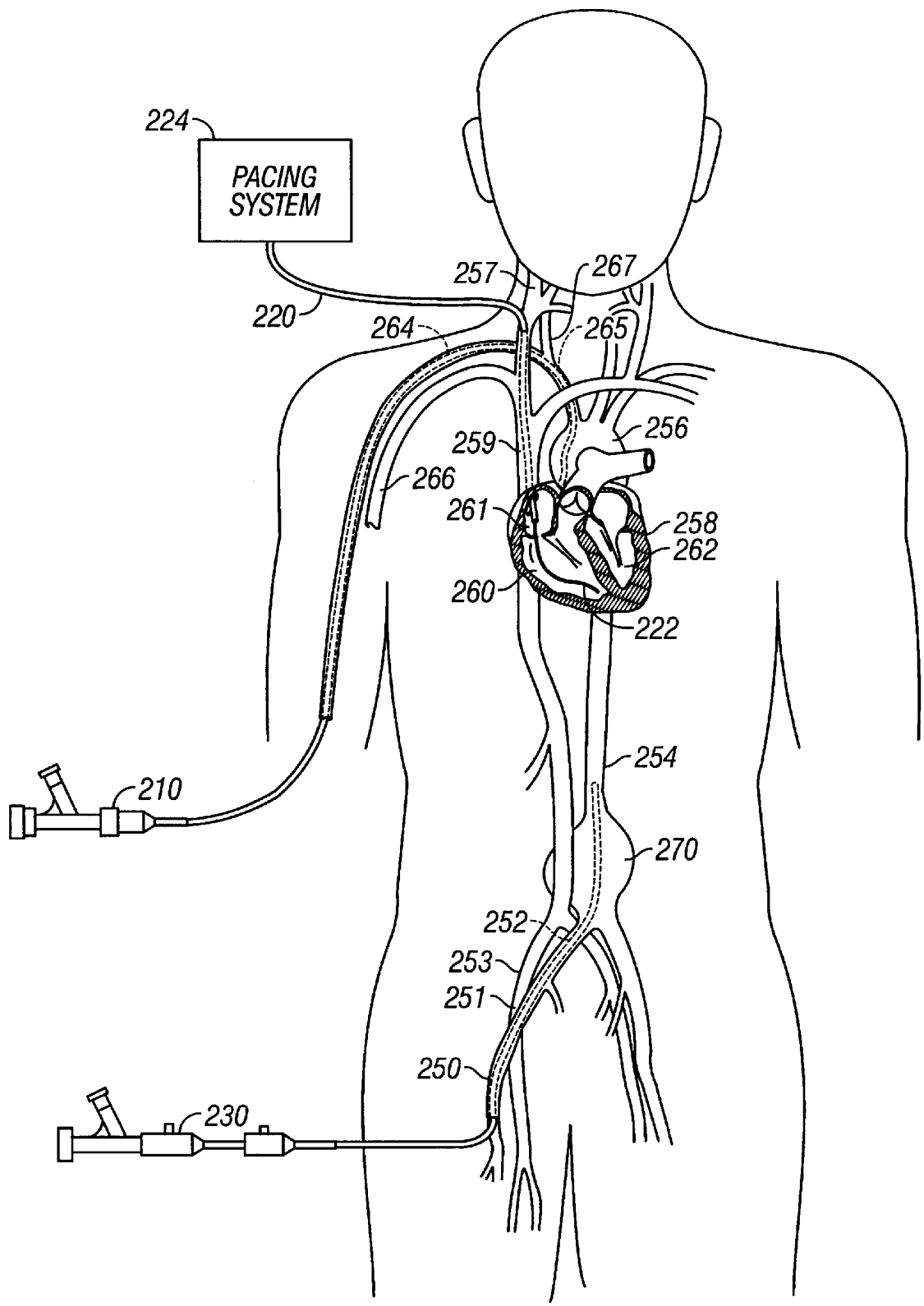
FIG. 9B illustrates an alternative route of introduction of the pacing system catheter of FIG. 9A.
Figure 9C:
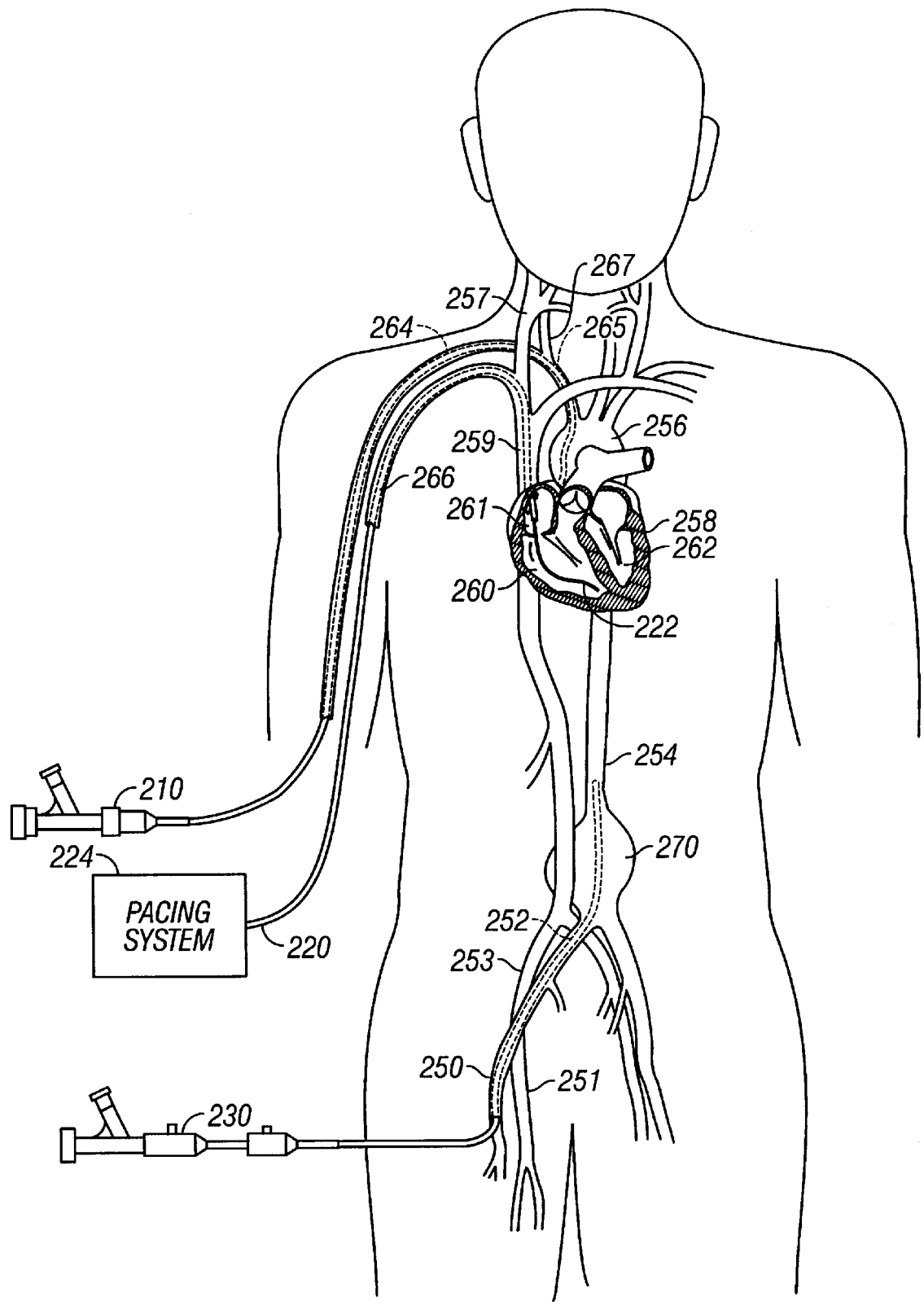
FIG. 9C illustrates an alternative route of introduction of the pacing system catheter of FIG. 9A.
Figure 9D:
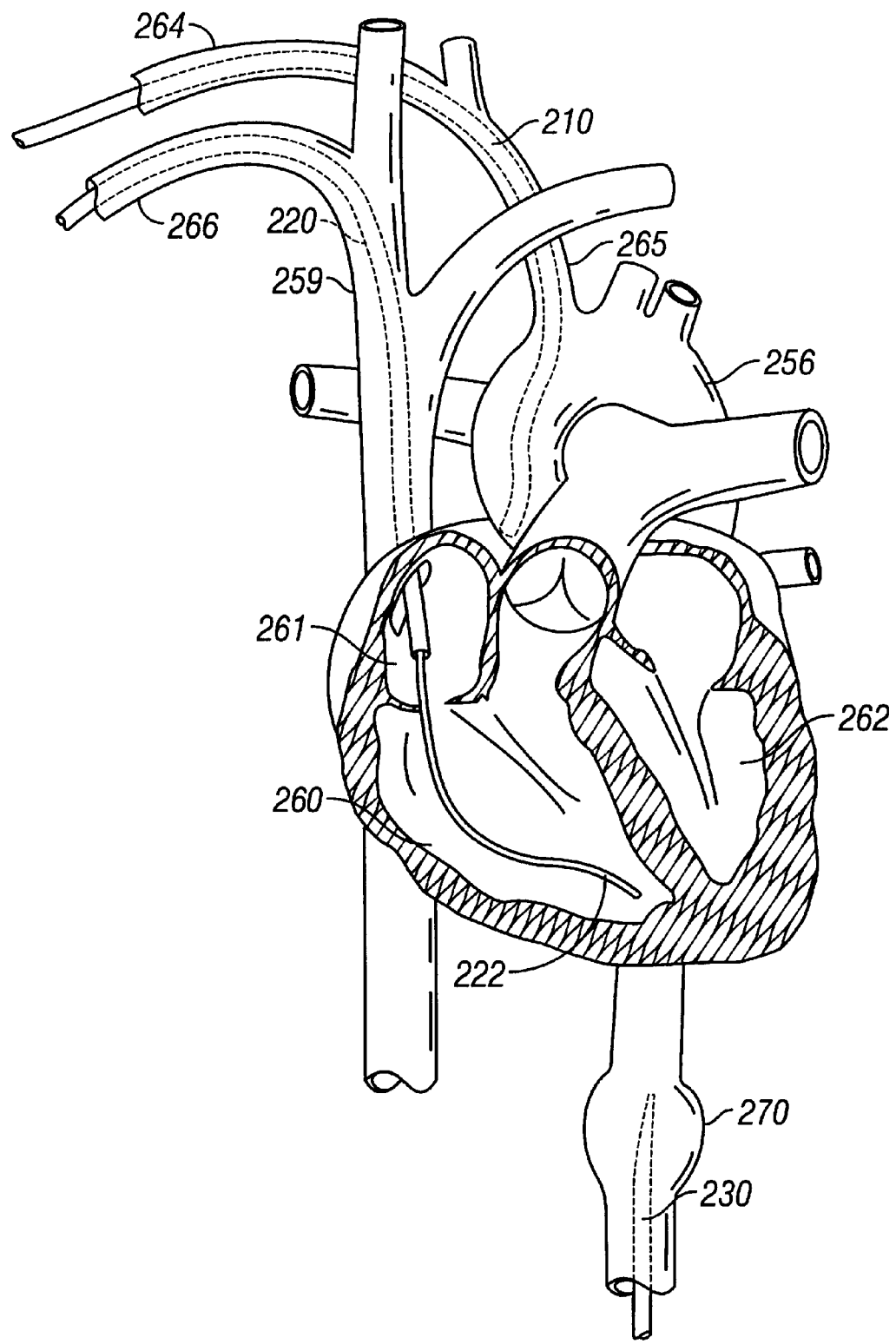
FIG. 9D is an exploded view of the heart of FIG. 9A showing the advancement of the drug delivery catheter through the aorta into the right coronary artery, the advancement of the pacing system catheter into the right ventricle, and the introduction of the endovascular aortic prosthetic delivery catheter into the aorta at the site of an aneurysm therein.

Next, a transvenous endocardial pacing catheter 220 which is conventional (e.g., a Daig Pacel™ bipolar endocardial pacing catheter from Daig Corporation, Minnetonka, Minn.) may be introduced into the internal jugular vein or saphenous vein 257 near the neck of the patient (FIG. 9B) by way of a cut-down or percutaneous technique (e.g., the Seldinger technique) and advanced through the superior vena cava 259 and into the right atrium 261 under fluoroscopic or echocardiographic guidance, as shown, for example, in FIG. 9B. With the help of a guidewire, the pacing catheter 220 can then be advanced across the tricuspid valve and into the right ventricle 260 of the heart. The distal end 222 of the pacing catheter 220 is then preferably positioned at the right ventricular apex as shown in the drawing figures. An introducer catheter (not shown) can be used to guide the transvenous endocardial pacing catheter 220 into the right ventricle 260 if required. As an alternative to internal jugular vein catheterization, the transvenous endocardial pacing catheter 220 could also be introduced through an alternative peripheral access site, such as median basilic vein 266 in the arm (FIG. 9C), or a femoral or iliac vein 251, 253 in the groin area (FIG. 9A). The transvenous endocardial pacing catheter 220 is operatively connected to an extracorporeal pacing system 224 which generally comprises a pacer switch or control box 14 and an extracorporeal pacer unit 18 described herein in connection with FIGS. 1–1E. It also should be understood that endocardial or epicardial pacing systems may be used.

The next step of the procedure involves positioning the stent graft deployment mechanism and stent graft within the abdominal aorta 254 (or thoracic aorta 256) at the site of aneurysm 270. Endovascular devices which can be used for aortic aneurysm repair include, for example, balloon-expandable or self-expandable devices. Balloon-expandable stent designs are described, for example, in Parodi et al.,*Ann. Vasc. Surg.* 1991; 5:491–499 and White et al.,*J. Endovasc. Surg.* 1994; 1:16–24, the disclosures of which are incorporated by reference herein. An example is the EGS System EndoGraft® Prosthesis (Endo Vascular Technologies, Inc., Menlo Park, Calif.). Devices using self-expanding stents include, for example, the Stentor graft (MinTec, Minimally Invasive Technologies, Freeport, Grand Bahama, The Bahamas) and the Corvita graft (Corvita Corp., Miami Lakes, Fla.), as well as the designs disclosed in Dake et al., *N. Eng. J. Med.* 1994; 331:1729–1734, which is incorporated by reference herein.

An example of one of many suitable deployment mechanisms is the Endovascular Technologies, Inc. (Menlo Park, Calif.) EGS® System Delivery Catheter 230 shown in FIGS. 9A–D and more fully described, for example, in U.S. Pat. No. 5,489,295, the disclosure of which is incorporated by reference herein. The EGS system generally consists of an endograft prosthesis (not shown) and a corresponding delivery catheter 230. The prosthesis is a vascular graft which isolates the aneurysm 270 from blood flow and pressurization, thus precluding aneurysm expansion and minimizing the risk of rupture. The delivery catheter 230 is an over-the wire system which is subcutaneously inserted into a femoral or iliac artery 250, 252 in the groin area using known techniques such as a cut-down or a percutaneous technique such as the Seldinger technique. The delivery catheter 230 is advanced into the aorta 254 under fluoroscopic or echocardiographic guidance to the site of the aneurysm 270 and is designed to transport the preloaded prosthesis to the aorta.

With the endograft delivery catheter 230 in place within the aorta at the site of the aneurysm 270, the next step in the procedure is to induce reversible ventricular asystole of the heart 258 to facilitate a controlled, accurate implantation across the aneurysm. It should be understood, however, that reversible ventricular asystole may be induced prior to placing the delivery catheter at the operative site as well. Any approved pharmaceutical agent(s) which is capable of inducing at least a brief period of cardiac asystole from several seconds to several minutes may then be used with the method. Preferably, the method includes providing a period of asystole which has a duration of more than approximately one minute, for example about 1 to 30 minutes, for example about 3 to 20 minutes. In one embodiment, the period of asystole is induced by administering an AV node blocker and a β-blocker to the heart at a sufficient dosage amount of each to induce asystole in the heart. The AV node blocker in one embodiment may comprise a cholinergic receptor agonist, such as carbachol, although other AV node blockers and other ways of inducing third degree block of the AV node (such as electrical, ultrasonic, or cryogenic stimulation of the AV node) are also contemplated by the present invention as disclosed in more detail herein. The β-blocker in one embodiment comprises propranolol, although other β-blockers may also be used.

The method may include electrically pacing the heart with, for example, the electrical pacing system 224, thereby to maintain the patient's blood circulation, and selectively intermittently stopping the electrical pacing at least once during the procedure to allow one or more intermittent periods of asystole of the heart, each of the one or more intermittent periods of asystole having a duration of from about 1 to 30 seconds, for example about 1 to 15 seconds. In one embodiment of the method, the pharmaceutical compounds are serially delivered to the heart, and the β-blocker is administered prior to the AV node blocker. The β-blocker may also be delivered simultaneously with or following the administration of the AV node blocker. The β-blocker preferably is administered in an amount sufficient to substantially reduce the amount of AV node blocker required to induce asystole of the heart.

The method can include delivering the AV node blocker and the β-blocker to the right or left coronary artery of the heart, e.g., proximal to the AV node artery as shown, for example, in FIGS. 6 and 8. The AV node blocker and β-blocker may be administered to the right or left coronary artery through drug delivery catheter 210 which has at least one discharge opening which is positioned in the right or left coronary artery. Where an open-chest procedure is used, the compounds may be delivered to the heart using any of the novel devices and techniques for fluid or drug administration disclosed, for example, in co-pending patent-application Ser. No. 09/196,636 filed on Nov. 19, 1998, now abandoned In one embodiment, the method described above comprises the intracoronary administration of propranolol to the coronary artery as one or more bolus infusions (e.g., at about 1 to 3 mg per bolus) at a total dosage amount of about 1 to 8 mg, for example about 1 to 6 mg, for example about 1 to 4 mg, for example about 2 to 3 mg. The method also comprises the serial intracoronary administration of carbachol to the coronary artery as one or more initial bolus infusions (e.g., about two to three bolus infusions) at a total dosage amount of about 0.001 to 1.0 mg per bolus, for example about 0.05 to 0.5 mg per bolus, for example about 0.025 to 0.30 mg per bolus. This should be sufficient to induce a period of asystole with a duration of about 1 to 30 minutes, for example about 3 to 20 minutes, which should be sufficient time for accurate release and implantation of the prosthesis in the aorta, such as at the site of the aneurysm 270, to thereby isolate the aneurysm from blood flow and pressurization, thus precluding aneurysm expansion and minimizing the risk of rupture. If necessary, the method may include repeating the above bolus drug dosing regimen one or more times during the procedure to induce a sufficient period of controlled and stable asystole to complete the procedure. For example, one or more repeat bolus doses of about 1 to 3 mg of propranolol and about 0.025 to 0.5 mg of carbachol per bolus can be given to the patient to maintain consistent and reliable arrest, as necessary.

Alternatively, if necessary, the method may further comprise maintaining the period of asystole for a longer duration by administering a continuous intracoronary infusion of carbachol to the heart of the patient at a rate of about 0.001 to 0.3 mg/min, for example about 0.005 to 0.3 mg/min, for example about 0.005 to 0.1 mg/min, over a period of about 5 to 90 minutes, for example, as appropriate.

The transvenous pacing catheter 220 is used to pace the heart 258 to maintain the patient's blood circulation except during the periods in which asystole would facilitate the procedure. Thus, for example, while the prosthetic graft is being deployed in the aorta 254, the surgeon can control the pacing of the heart and can controllably stop the heart to accurately approximate the prosthetic graft to the aortic wall around the aneurysm 270 while avoiding device movement during deployment. Thus, transient ventricular asystole induced by the techniques of the present invention is a simple and safe technique that facilitates accurate placement of prosthetic grafts, such as endovascular balloon-expandable or self-expanding stent grafts, in the thoracic or abdominal aorta.

An intravenous dosage of about 1.0 mg of phenylephrine or levofed can be systemically administered to the patient to control any hypotensive effects associated with carbachol administration. In most situations, atropine (about 1 mg) is used to reverse ventricular asystole and restore the heart to its normal function following the procedure. Intracoronary administration of vasodilators (e.g., nitroglycerine (e.g., about 200 mcg), glyceryl trinitrate, papaverine, verapamil) can also be administered to the heart to counteract any vasoconstrictive effects associated with phenylephrine or levofed administration. If necessary, a cardiac assist device, such as the Hemopump® (Medtronic, Minneapolis, Minn.), may be used to augment circulatory blood flow when the function of the heart is or may become compromised during the procedure.

Transmyocardial Revascularization Medical Procedures

The compositions, apparatus, systems and methods for heart rate and rhythm control management described herein can be used to assist in transmyocardial revascularization (TMR) procedures, such as transmyocardial laser revascularization (TMLR) or percutaneous transmyocardial revascularization (PTMR) procedures.

Transmyocardial revascularization (TMR) procedures, such as transmyocardial laser revascularization (TMLR) or percutaneous transmyocardial revascularization (PTMR) procedures, are generally used in patients with coronary artery disease who suffer from severe, stable angina not treatable by conventional coronary revascularization (e.g., coronary artery bypass graft surgery and/or angioplasty). In TMR procedures, surgeons typically use a high-powered carbon dioxide laser to create tiny holes in the heart muscle. These holes develop into channels, and blood from the patient's left (or right) ventricle flows through them to the diseased portion of the heart created by the narrowed or blocked arteries.

TMR procedures typically are performed on the beating heart. The operation can be performed using an open-heart technique, such as a TMLR procedure. In another form of TMR procedure, a PTMR procedure can be performed using a minimally invasive percutaneous technique in which the laser apparatus is inserted percutaneously and directed to the heart so that the tip of the catheter is placed inside a chamber of the heart, typically the left ventricle, where the holes or channels can be created from the inside toward but not through the outside of the heart.

Using the disclosed methods, TMR procedures may be performed while minimizing translational motion of the beating heart, which translational motion can make accurate positioning and focusing of the energy apparatus relative to the heart difficult. Inaccurate positioning of the energy apparatus can result, for example, in laser-induced trauma to the heart (e.g., thermal or mechanical damage to the heart) and insufficient or excessive channel propagation through the heart wall, which can decrease the patency of blood flow from the ventricular chamber into the myocardium and/or lead to bleeding. The disclosed techniques can be used to induce reversible ventricular asystole of the heart to create a motionless surface of the heart, facilitating the accurate deployment and energy administration of the appropriate energy source to obtain accurate channel propagation through the heart wall.

The transmyocardial revascularization procedure may be performed using an open chest technique in which the blood flow channel in the heart is created by irradiating an exterior surface of the heart with laser energy from an external laser apparatus. Access to the thoracic cavity is achieved through a partial or median sternotomy or more preferably through a left side mini-thoracotomy (e.g., a 6 to 12 cm incision on the left side of the chest cavity, preferably between the fourth and fifth intercostal spaces). For example, U.S. Pat. No. 5,380,316, the disclosure of which is incorporated by reference herein, describes a method for intra-operative TMLR which uses a flexible laser apparatus to deliver a beam of energy to the exterior wall of the heart through a small incision in the chest wall. The laser drills holes in the myocardium of one of the ventricles of the heart, typically the left ventricle. The holes or channels extend through the entire heart wall thickness from the outside through to the ventricle. The channels heal on the outside surface of the heart due to external pressure from the surgeon, but remain open on the inside, allowing blood to enter the heart wall tissue from the ventricle.

Figure 10A:
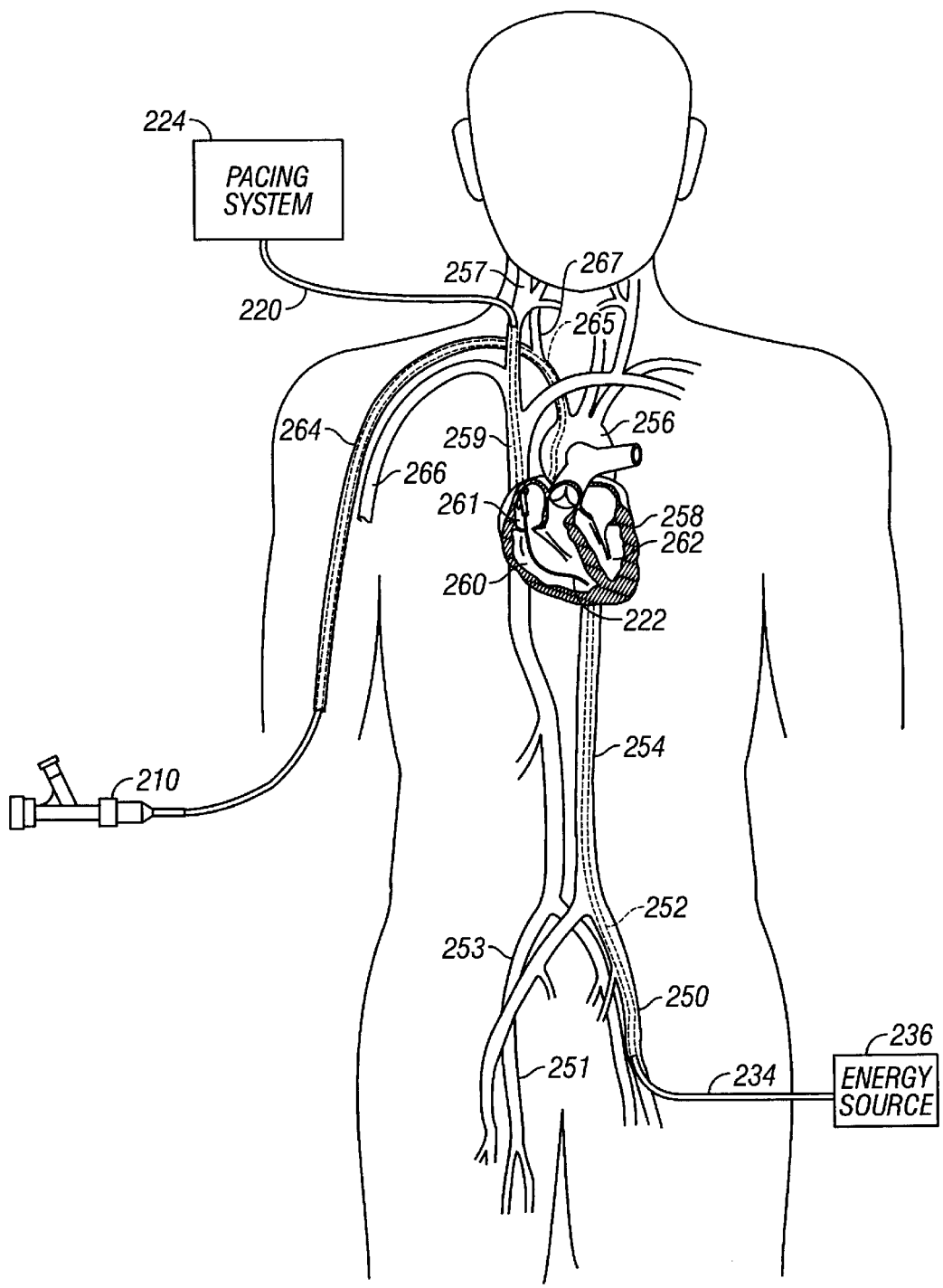
FIG. 10A diagrammatically illustrates a system for percutaneous transmyocardial revascularization in accordance with the invention.

The transmyocardial revascularization procedure may also be performed by a less invasive technique in which the laser (or other energy source) apparatus is percutaneously inserted into the heart, and wherein the blood flow channel in the heart is created by irradiating an interior surface of the heart with laser (or other) energy. For example, U.S. Pat. No. 5,389,096, the disclosure of which is incorporated by reference herein, describes a system and method for PTMR in which a flexible fiberoptic laser apparatus is used to deliver a beam of energy to the interior wall of the heart through a percutaneous approach, e.g., through a femoral artery. The method used to drill the channels can be mechanical, e.g., a needle; electrical, e.g., bipolar or unipolar electric current; r.f. microwave; or optical, e.g., a laser as described herein. Typically, a holmium (HO:YAG) laser or an excimer laser is used percutaneously. Referring now to FIG. 10A, a system is schematically illustrated for inducing reversible ventricular asystole of the heart during a PTMR procedure.

Similar to the previous embodiment, with the patient in the supine position as shown, a drug delivery catheter 210 such as described above in connection with the previous embodiment is preferably subcutaneously inserted into a brachial or radial artery 264 in the arm using known techniques such as a direct cut-down or a percutaneous technique such as the Seldinger technique. Alternatively, the drug delivery catheter may also be percutaneously inserted from other peripheral vascular access points such as femoral or iliac artery 250, 252 in the groin area, or a carotid or subclavian artery 267 in the neck area of the patient.

A guidewire (not shown) is first inserted into the brachial or radial artery 264 and advanced toward the heart 258 under fluoroscopic or echocardiographic guidance through the brachiocephalic artery 265 and thoracic aorta 256 until the distal end of the guidewire is in the coronary ostium of the right (or left) coronary artery (not shown for clarity). Drug delivery catheter 210 can then be positioned over the guidewire, introduced into brachial or radial artery 264, and advanced over the guidewire through the brachiocephalic artery 265 and aorta 256 and into the coronary ostium.

Alternatively, a guide catheter (not shown) can be used to facilitate positioning of the drug delivery catheter 210 into the coronary ostium. Where a guide catheter is employed, the guide catheter will be retracted from the ostium of the right (or left) coronary artery into the aorta following placement of the drug delivery catheter in the ostium. The guidewire can then be advanced to a suitable drug delivery location within the right coronary artery, for example proximal to the AV node artery as shown in FIG. 6, and the catheter tip advanced over the guidewire and positioned at the drug delivery location within the right (or left) coronary artery.

The at least one discharge opening (not shown) of drug delivery catheter 210 is preferably positioned within about 8 cm from the AV node artery, for example between about 1 to 3 cm proximal to the AV node artery, to minimize drug dilution to collateral vessels.

Next, a transvenous endocardial pacing catheter 220 as described above may be introduced into carotid vein or subclavian vein 257 near the neck of the patient by way of a cut-down or percutaneous technique and advanced through the superior vena cava 259 and into the right ventricle 260 of the heart 258. An introducer catheter (not shown) can be used to guide the transvenous endocardial pacing catheter 220 into the right ventricle 260 if required. As an alternative to carotid or subclavian vein introduction, the transvenous endocardial pacing catheter could also be introduced through an alternative peripheral access site, such as median basilic vein 266 in the arm, or a femoral or iliac vein 251, 253 in the groin area. The transvenous endocardial pacing catheter 220 is operatively connected to an extracorporeal pacing system 224 described herein. It also should be understood that endocardial or epicardial pacing systems may be used.

The next step of the procedure involves positioning the elongated flexible energy delivery catheter apparatus 234 coupled to energy source 236 (e.g., a laser source) into the left ventricle 262 having an area in need of increased blood circulation due to cardiovascular disease. The energy delivery catheter 234 is inserted into the vasculature of the patient through a peripheral access site such as the femoral or iliac artery 250, 252 and advanced under fluoroscopic or echocardiographic guidance to the left ventricle 262 via the aorta 256. Portions of the heart other than the ventricles might also be revascularized by the methods of the present invention. A flexible guide catheter may also be used to guide the catheter 234 into the proper position within the heart 258. The energy delivery catheter 234 preferably includes an optical fiber on the order of about 240 microns in diameter which is optically coupled to an extracorporeal laser energy source 236 at the proximal end of the optical fiber. The energy delivery catheter 234 may be a carbon dioxide laser, a holmium:YAG laser, an erbium laser, an Nd:YAG laser, an excimer laser, or any other appropriate energy source capable of making small channels in the heart wall. The catheter 234 may also include a lens to focus the laser energy as described more fully, for example, in U.S. Pat. No. 5,389,096 previously incorporated by reference herein.

With the energy delivery catheter 234 in place within the ventricle 262 at the operative site, the next step in the procedure is to induce reversible ventricular asystole of the heart to facilitate accurate and efficient channel formation in the ventricular endocardium and through a portion of the heart's myocardium. This can be accomplished by administering one or more pharmaceutical agents to the heart which is/are capable of inducing at least a brief period of asystole. It should be understood, however, that reversible ventricular asystole may be induced prior to placing the delivery catheter at the operative site as well.

In one embodiment, the method of performing a TMR procedure in the heart of a patient comprises creating at least one blood flow channel within a wall of the heart of the patient, the at least one blood flow channel having a fluid connection with a chamber of the heart, comprising inducing prior to or during the revascularization procedure at least one period of electrically paceable asystole in the heart which has a duration of more than approximately one minute.

The method can include, for example, providing a period of asystole which has a duration of about 1 to 30 minutes, for example about 3 to 20 minutes. In one embodiment, the period of asystole is induced by administering an AV node blocker and a β-blocker to the heart at a sufficient dosage amount of each to induce asystole in the heart. The AV node blocker in one embodiment may comprise a cholinergic receptor agonist, such as carbachol, although other AV node blockers and other ways of inducing third degree block of the AV node (such as electrical, ultrasonic, or cryogenic stimulation of the AV node) are also contemplated by the present invention. The β-blocker in one embodiment comprises propranolol, although other β-blockers may also be used.

The method may include electrically pacing the heart with, for example, electrical pacing system 224, thereby to maintain the patient's blood circulation, and selectively intermittently stopping the electrical pacing at least once during the procedure to allow one or more intermittent periods of asystole of the heart, each of the one or more intermittent periods of asystole having a duration of from about 1 to 30 seconds, for example about 1 to 15 seconds. In one embodiment of the method, the pharmaceutical compounds are serially delivered to the heart, and the β-blocker is administered prior to the AV node blocker. The β-blocker may also be delivered simultaneously with or following the administration of the AV node blocker. The β-blocker preferably is administered in an amount sufficient to substantially reduce the amount of AV node blocker required to induce asystole of the heart.

The method can include delivering the AV node blocker and the β-blocker to the right or left coronary artery of the heart, e.g., proximal to the AV node artery as schematically illustrated in FIG. 6, for example. The AV node blocker and β-blocker may be administered to the right or left coronary artery through drug delivery catheter 210 which has at least one discharge opening which is positioned in the right or left coronary artery.

In one embodiment, the method described above comprises the intracoronary administration of propranolol to the coronary artery as one or more bolus infusions (at about 1 to 3 mg per bolus) at a total dosage amount of about 1 to 8 mg, for example about 1 to 6 mg, for example about 1 to 4 mg, for example about 2 to 3 mg. The method also comprises the serial intracoronary administration of carbachol to the coronary artery as one or more initial bolus infusions (e.g., about two to three bolus infusions) at a total dosage amount of about 0.001 to 1.0 mg per bolus, for example about 0.05 to 0.5 mg per bolus, for example about 0.025 to 0.30 mg per bolus. This should be sufficient to induce a period of asystole with a duration of about 1 to 30 minutes, for example about 3 to 20 minutes, which should be sufficient time for accurate and precise channel creation in the heart. If necessary, the method may include repeating the above drug dosing regimen one or more times during the procedure to induce a sufficient period of asystole to complete the procedure. For example, one or more repeat bolus doses of about 1 to 3 mg of propranolol and about 0.025 to 0.5 mg of carbachol per bolus can be given to the patient to maintain consistent and reliable arrest, as necessary.

Alternatively, if necessary, the method may further comprise maintaining the period of asystole for a greater duration by administering a continuous intracoronary infusion of carbachol to the heart of the patient at a rate of about 0.001 to 0.3 mg/min, for example about 0.005 to 0.3 mg/min, for example about 0.005 to 0.1 mg/min, over a period of about 5 to 90 minutes, as appropriate.

With the heart in controlled ventricular asystole, a number of blood channels (e.g., about 10 to 40 channels) approximately 1.5 to 2.0 mm in diameter and approximately 1.0 to 3.0 cm deep may be easily and efficiently cut into the ventricular wall. The distal end of the energy delivery catheter 234 may be retained in position on the inner ventricular wall by gently applying pressure to the proximal end of the device to push it forward into the tissue or by applying a vacuum at the distal tip of the device. In one representative embodiment, when using a holmium:YAG laser, approximately 0.65 J pulses, at a frequency of at least about 2 Hz, are applied to penetrate the endocardium, and then approximately 0.2 J pulses are applied to form the channel in the myocardium. The laser parameters may, however, be varied depending on patient anatomy and according to clinical experience. Because the heart 258 is not moving during the period of ventricular asystole, the laser-created blood flow channels can be quickly and accurately probed with the laser device (and/or by using any of the techniques of monitoring the depth of channels created during the procedure which are fully described in U.S. Pat. No. 5,893,848, the disclosure of which is incorporated by reference herein) to verify sufficient and accurate penetration of the channels into the ventricular wall and to verify adequate fluid coupling between the blood flow channels and the ventricular chamber.

The transvenous pacing catheter 220 is used to pace the heart 258 to maintain the patient's blood circulation during the periods in which the surgeon is temporarily not performing the PTMR procedure. Thus, for example, while the channels are being formed in the endocardium and/or myocardium, the surgeon can control the pacing of the heart and can controllably stop the heart to accurately and efficiently form the channels. Thus, transient ventricular asystole induced by the disclosed techniques is a simple and safe technique that facilitates accurate formation of blood flow channels in the ventricular wall in an ischemic region of the heart to thereby improve blood flow to the ischemic region.

Figure 10B:
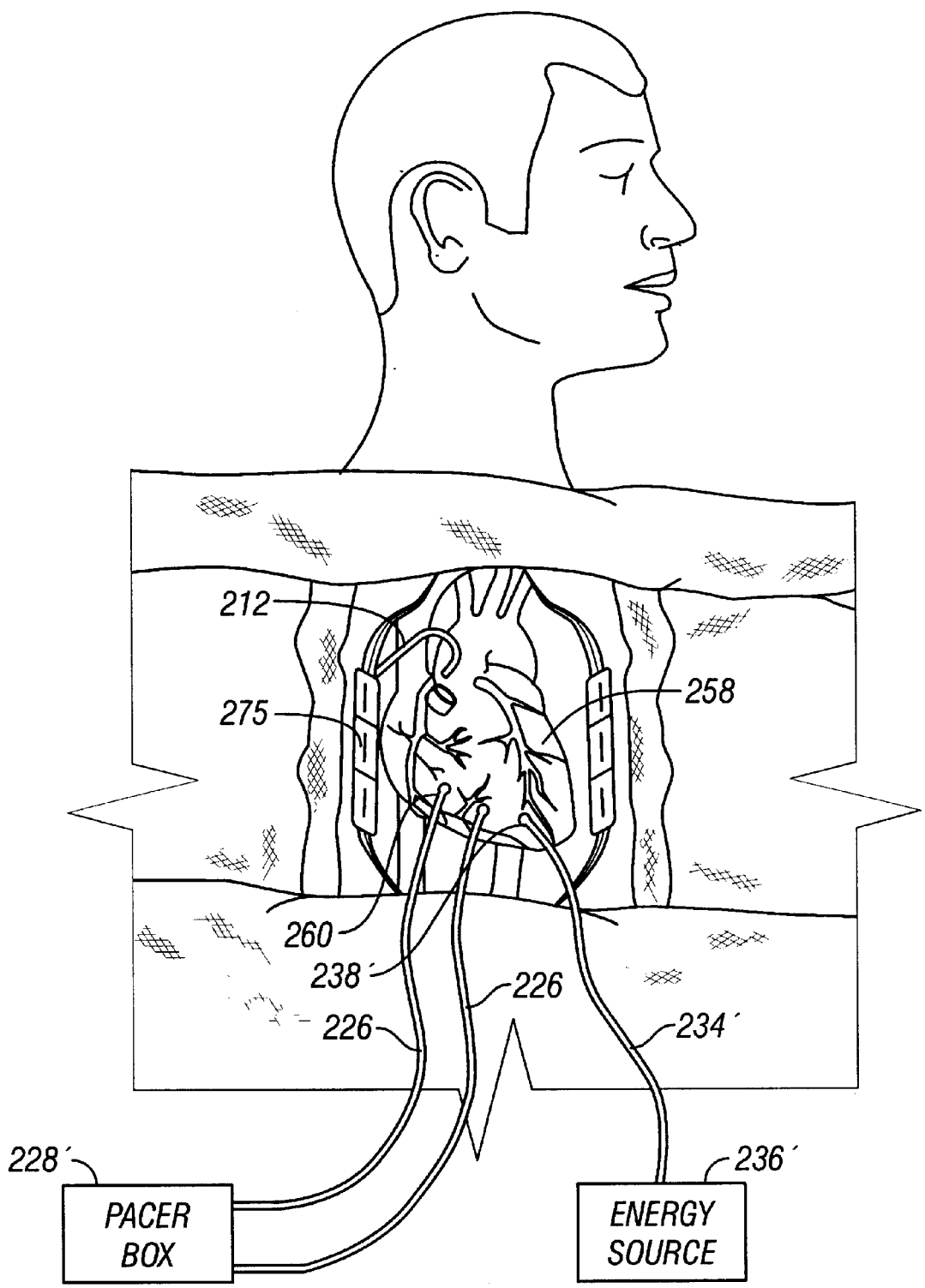
FIG. 10B diagrammatically illustrates a system for open-chest transmyocardial revascularization in accordance with the invention.

It is to be appreciated that the blood flow channels can be created from the interior of the heart by the PTMR procedure described above or from the exterior of the heart in an open-chest or minimally invasive thoracoscopic surgical procedure such as is schematically illustrated in FIG. 10B. For example, in the open-chest procedure of FIG. 10B, the heart is exposed by a median or partial sternotomy and the thoracic cavity is kept open using surgical retractor 275. Surgical retractor 275 is used to spread the ribs to provide direct access to the thoracic cavity. An example of a suitable surgical retractor 275 is disclosed, for example, in any one of U.S. Pat. Nos. 4,726,356, 4,829,985, and 5,025,779, the disclosures of which are incorporated by reference herein.

When creating the blood flow channels from the exterior of the heart as shown in FIG. 10B using the distal end 238' of energy delivery catheter 234', the pharmaceutical compositions required to achieve reversible ventricular asystole can be administered to the heart using any one of the open-chest catheterization techniques described herein (e.g., by needle injection), by any one of the novel catheterization devices and techniques disclosed, for example, in co-pending patent application Ser. No. 09/196,636 filed on Nov. 19, 1998, now abandoned.

Epicardial pacing electrode leads 226 coupled to pacer box 228 are sewn into place on the ventricle 260 (and, optionally, the right atrium), and are used to pace the heart to maintain the patient's blood circulation as described herein. The channel propagation procedure is then conducted using a similar drug dosing regimen and similar techniques as described herein for a PTMR procedure.

Computed Tomography (CT) Scan and Magnetic Resonance Imaging (MRI) Procedures The compositions, apparatus, systems and methods for heart rate and rhythm control management described herein can be used to assist in imaging procedures of various bodily organs such as the brain, chest, heart, lungs, abdomen, pelvis, liver, spleen, kidneys, pancreas, etc. using CT scanning or MRI imaging equipment.

A CT (computed tomography) scan, or CAT (computed axial tomography) scan, is an X-ray procedure which provides detailed anatomical images of the body. However, CT (or CAT) scans are far more detailed and accurate than a standard X-ray. In standard CT, each revolution of the X-ray tube around the patient produces a single visual image "slice" that demonstrates the tissue that was traversed by the X-ray beam during that exposure. When imaging the body (e.g., the chest or abdomen), the patient is often instructed to hold their breath during the image acquisition time to minimize blurring of the image by motion. This image acquisition time, or exposure, usually takes only a few seconds. After the exposure, the table moves a small amount so that the next continuous slice of tissue can be exposed. The delay between slices usually takes about 5 to 10 seconds. The process is repeated numerous times until the full extent of the portion of the body being studied is imaged.

A recent advance in CT technology is the advent of spiral (or helical) CT. During spiral CT, the X-ray tube rotates continuously as the patient is smoothly moved through the X-ray scan field. Unlike the separate data sets produced for each individual slice in standard CT, spiral CT produces one continuous volume set of data for the entire region scanned. Since the patient is moving continuously through the scanner, the duration of the exam is markedly shortened for spiral CT versus standard CT. The entire chest (e.g., heart) or abdomen can be scanned in about 30 seconds or less, usually during a single breath-hold.

Unlike a CT scan or other radiology devices, an MRI scan requires the use of a very strong magnetic field and does not use radiation. The magnet (e.g., a superconducting magnet) is contained in the housing of the scanner and creates a magnetic field down the center the magnet. The patient is placed within the magnetic field by lying on a table which is placed through a large donut-shaped opening in the magnet similar to a CT scanner. The patient is often asked by the MRI technologist to lie as still as possible during the image acquisition process to enhance the quality of the anatomical images.

Using the methods disclosed herein, MRI or CT scan procedures can be performed while minimizing cardiac and/or respiratory motion, which motion may, in some situations, render inexact MRI or CT scan images. The disclosed methods are believed to be the first attempt to transiently arrest the heart to facilitate diagnostic imaging procedures. Although the disclosed techniques may be applied to imaging procedures of a variety of anatomical structures such as the brain, chest, lungs, heart, abdomen, pelvis, etc., the disclosed techniques may be particularly applicable to diagnostic cardiac imaging applications which might most benefit from a transiently arrested heart and/or the cessation of blood flow. The techniques of the present invention may be particularly useful, for example, with cardiovascular diagnostic applications of MRI and CT, which may, in some cases, be immediately followed by a surgical procedure to correct the demonstrated abnormality.

Nonlimiting examples of cardiac imaging procedures that might benefit from the disclosed techniques include the accurate assessment of cardiac dimensions and function such as the precise demonstration and quantification of global and regional function of the right and left ventricles, the precise demonstration of cardiac abnormalities such as segmental myocardial wall thinning that is indicative of previous myocardial infarction, the quantification of valvular heart disease, the measurement of blood flow in the heart and great vessels, the evaluation of the patency of coronary artery bypass grafts, the evaluation of diseases of the thoracic aorta such as aortic dissection, true and false aneurysms, aortic arch abnormalities, and coarctation of the aorta, the characterization of myocardial tissue, the detection of calcification in the coronary arteries to predict the presence of coronary stenosis, the demonstration of congenital abnormalities such as absence of the pericardium and pericardial cyst, the diagnosis of loculated pericardial effusions, the detection of blood clots in the vessels that go to the lungs (e.g., pulmonary emboli), the detection of growths and tumors in the chest that may or may not involve the heart, and the assessment of myocardial perfusion and even coronary blood flow. Precise demonstration of anatomical dimensions and function in the heart is useful for the evaluation of patients with, for example, ischemic heart disease, cardiomyopathies, pericardial disease, neoplastic disease, congenital heart disease, and thoracic aortic disease.

Figure 11:
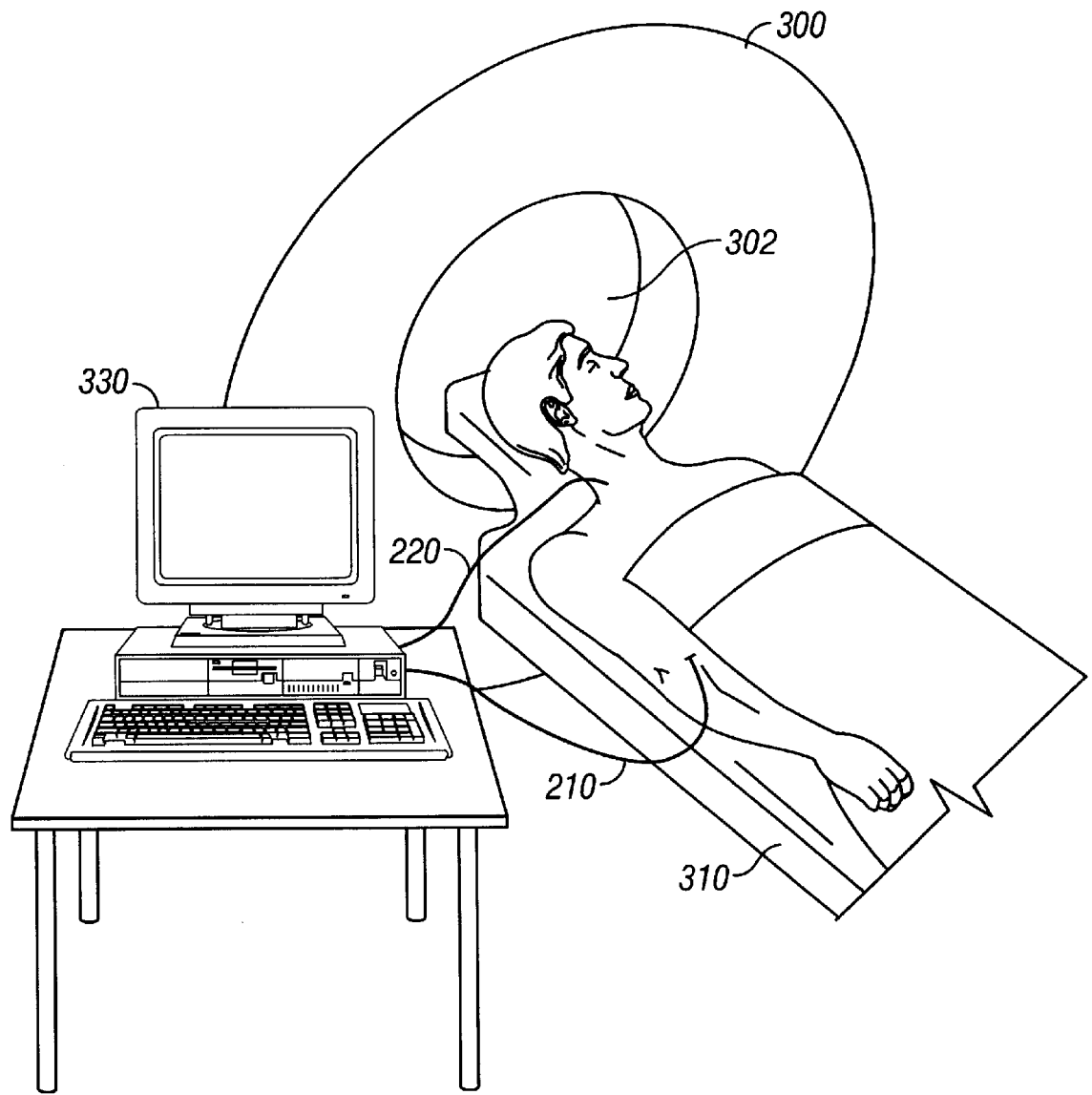
FIG. 11 diagrammatically illustrates an imaging system such as an MRI or CT scan system in accordance with invention.

To perform a CT scan or MRI imaging procedure using disclosed techniques, a closed chest endoscopic technique is used to arrest the heart similar to a PTMR procedure described above. Referring now to FIG. 11, a perspective view is shown of a patient being inserted into an imaging apparatus such as an MRI or CT scan device 300 following placement of a drug delivery catheter and a pacing system catheter into the patient's heart.

The patient is first catheterized for the procedure using similar catheterization techniques as to those described herein. A drug delivery catheter 210 such as described herein is inserted into the patient's vasculature system from a peripheral access point such as a femoral or iliac artery 250, 252 in the leg (as shown), a brachial or radial artery 264 in the arm (as shown in FIG. 11), or a carotid or subclavian artery 267 near the neck, and guided with the aid of fluoroscopy or echocardiography into place in the right (or left) coronary artery, preferably proximal to the AV node artery.

A transvenous pacing catheter 220 such as the Pacel® catheter described herein is next introduced into the vasculature system of the patient via a suitable peripheral access point such as via the basilic vein in the arm 266 and the superior vena cava 259 and positioned in the right ventricle 260 of the heart. The transvenous pacing catheter 220 may also be introduced into the right ventricle 260 from other peripheral access points such as via the jugular vein 257 in the neck (as shown in FIG. 11) or the femoral or iliac vein 251, 253 in the leg by a direct cut-down or percutaneous insertion technique. It also should be understood that endocardial or epicardial pacing systems may be used.

With the patient fully catheterized as described above, the patient is positioned in the supine position on the appropriate scanner table 310 and then slowly moved into the large opening 302 in the CT scan or MRI scanner 300. The patient may be given an injection of oral contrast material which enhances the visibility of the structures within the body. The contrast material may be given by mouth, by injection, or both. A computer and monitor system 330 is used by the practitioner to process and view the anatomical structures of the body imaged by scanning apparatus 300.

Once the patient has been inserted into the scanner body 300 through opening 302 and is ready for image acquisition, the next step in the procedure is to induce at least a brief period of reversible ventricular asystole of the heart for a sufficient time period to facilitate accurate and reliable imaging of the anatomical structure to be viewed, such as the heart, for example. As noted herein, any approved pharmaceutical agent(s) which is capable of inducing at least a brief period of cardiac asystole from several seconds to several minutes may then be used with the method. In one embodiment, the method can include providing a period of asystole which has a duration of about 1 to 30 minute, for example about 3 to 20 minutes. In one embodiment, the period of asystole is induced by administering an AV node blocker and a β-blocker to the heart at a sufficient dosage amount of each to induce asystole in the heart. The AV node blocker in one embodiment may comprise a cholinergic receptor agonist, such as carbachol, although other AV node blockers and other ways of inducing third degree block of the AV node (such as electrical, ultrasonic, or cryonic stimulation of the AV node) are also contemplated by the present invention as disclosed in more detail herein. The β-blocker in one embodiment comprises propranolol, although other β-blockers may also be used. Preferably, a combination of an AV node blocker (and/or other AV node blocking techniques such as electrical, ultrasonic or cryogenic stimulation of the AV node) and one or more of the β-blockers described herein may then be used to induce at least a brief period of reversible ventricular asystole.

The procedure may include electrically pacing the heart with an electrical pacing system coupled to catheter 220, thereby to maintain the patient's blood circulation, and selectively intermittently stopping the electrical pacing at least once during the procedure to allow one or more intermittent periods of asystole of the heart, each of the one or more intermittent periods of asystole having a duration of from about 1 to 30 seconds, for example about 1 to 15 seconds. In one embodiment of the method, the pharmaceutical compounds are serially delivered to the heart, and the β-blocker is administered prior to the AV node blocker. The β-blocker may also be delivered simultaneously with or following the administration of the AV node blocker. The β-blocker preferably is administered in an amount sufficient to substantially reduce the amount of AV node blocker required to induce asystole of the heart.

The method can include delivering the AV node blocker and the β blocker to the right or left coronary artery of the heart, e.g., proximal to the AV node artery. The AV node blocker and β-blocker may be administered to the right or left coronary artery through drug delivery catheter 210 which has at least one discharge opening which is positioned in the right or left coronary artery. The at least one discharge opening (not shown) of drug delivery catheter 210 is preferably positioned within about 8 cm from the AV node artery, for example about 1 to 3 cm proximal to the AV node artery, to minimize drug dilution to collateral vessels.

In one embodiment, the procedure described above comprises the intracoronary administration of the β-blocker propranolol to the coronary artery as one or more bolus infusions (at about 1 to 3 mg per bolus) at a total dosage amount of about 1 to 8 mg, for example about 1 to 6 mg, for example about 1 to 4 mg, for example about 2 to 3 mg. The procedure also comprises the serial intracoronary administration of the AV node blocker carbachol to the coronary artery as one or more initial bolus infusions (e.g., about two to three bolus infusions) at a total dosage amount of about 0.001 to 1.0 mg per bolus, for example about 0.05 to 0.5 mg per bolus, for example about 0.025 to 0.30 mg per bolus. This should be sufficient to induce a period of asystole with a duration of about 1 to 30 minutes, for example about 3 to 20 minutes, which should be sufficient time for accurate and reliable image acquisition using the MRI or CT scanner 300. If necessary, the procedure may include repeating the above drug dosing regimen one or more times during the procedure to induce a sufficient period of controlled and stable asystole to complete the procedure. For example, one or more repeat bolus doses of about 1 to 3 mg of propranolol and about 0.025 to 0.5 mg of carbachol per bolus can be given to the patient to maintain consistent and reliable arrest, as necessary.

Alternatively, if necessary, the method may further comprise maintaining the period of asystole for a longer duration by administering a continuous intracoronary infusion of carbachol to the heart of the patient at a rate of about 0.001 to 0.3 mg/min, for example about 0.005 to 0.3 mg/min, for example about 0.005 to 0.1 mg/min, over a period of about 5 to 90 minutes, for example, as appropriate.

Alternatively, if the entire image acquisition process lasts for only about 1 minute or less, as may be the case with more sophisticated imaging technology such as, for example, with spiral (or helical) CT, the patient can be immediately returned to normal sinus rhythm by administering atropine (e.g., about 1 mg) to the patient, thereby not requiring cardiac pacing or pacing catheter 220. Pacing, however, may also be used as a recovery mechanism to assist the heart in returning to its normal sinus rhythm.

Thus, transient ventricular asystole induced by the techniques of the present invention is a simple and safe technique that facilitates accurate image acquisition during diagnostic imaging procedures, such as CT scan or MRI procedures.

Transesophageal Echocardiography Procedures

The compositions, apparatus, systems and methods for heart rate and rhythm control management described herein may also be used to facilitate a variety of other medical procedures of the type which employ an intraluminal probe for imaging, diagnostic, or therapeutic procedures. The commonality among such procedures is the introduction of an elongate device, such as a catheter, endoscope, transesophageal probe, cystoscope, urethroscope, or other conventional probe, through an orifice into an internal body lumen, cavity, or hollow organ. The orifice may be natural, such as the patient's mouth, colon, urethra, or may be performed by percutaneous (or direct cut-down) penetration using conventional techniques such as the Seldinger technique.

Imaging procedures which may be advantageously performed in conjunction with the disclosed methods and might benefit from an intermittent stoppage of blood flow include those in the field of cardiology, such as transesophageal echocardiography (described below), intravascular ultrasound, angioscopy, and electrophysiology; those in the field of radiology, such as the mapping of blood vessels feeding tumors, the location of sites for subsequent surgery or interventional radiology, and vascular sampling for hormonal studies, e.g., renal vein renins; those in the field of urology, such as cystoscopy; ureteroscopy, and prostatic ultrasound; those in the field of oncology, such as catheter drug delivery; those in the field of gastroenterology, such as upper and lower gastrointestinal endoscopy; and those in the field of pulmonology, such as bronchoscopy. While this list is representative of a wide variety of imaging procedures which can be performed in conjunction with the methods of the present invention, it is not intended to be exhaustive and other similar procedures which may be performed with the disclosed methods will be apparent to those skilled in the art.

Of particular interest to the disclosed techniques are ultrasonic imaging procedures, and in particular transesophageal echocardiographic procedures which utilize ultrasound to examine various organs of the body, such as the heart. Transesophageal echocardiography (TEE) procedures can be performed while minimizing the movement of the heart and/or lungs and pulsatile blood flow through the heart's circulation system, which movement may limit the clarity and precision of the images of the heart (or other organs).

TEE, for example, is a procedure that utilizes a transesophageal ultrasound probe (such as described in U.S. Pat. No. 4,633,882, the disclosure of which is incorporated by reference herein) that is inserted into the esophagus (e.g., the food tube that connects the mouth with the stomach) and which uses high frequency sound waves to capture images of anatomical body structures such as the heart. By this technique an ultrasonic transducer is inserted through the patient's mouth and into the esophagus or stomach. From such a position within the thoracic cavity, the ribs do not pose an impediment to the reception and transmission of ultrasound. The typical transesophageal scanhead includes a control mechanism external to the body which can be manipulated by the practitioner to direct the probe as desired towards the heart. The most common uses of TEE include searching for an abnormality in the heart or major blood vessels that might lead to a stroke, looking for infections on the heart valves, and evaluating the aorta for possible dissection or tear. It is also frequently used to monitor the heart during cardiac and noncardiac surgery, and can be used to facilitate the placement of catheters within the coronary vasculature system during cardiac surgical procedures such as, for example, coronary artery bypass graft procedures.

Figure 12A:
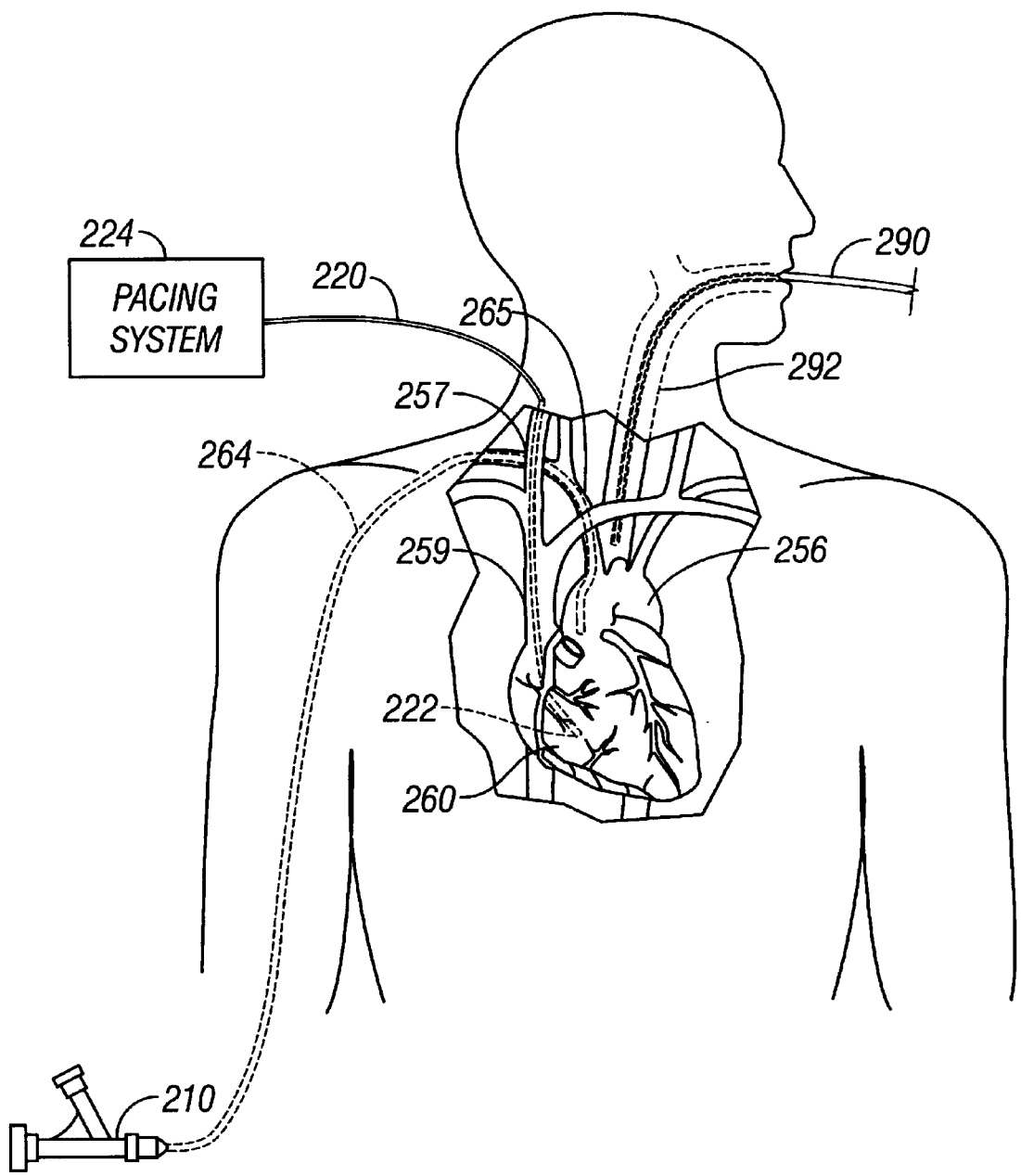
FIG. 12A diagrammatically illustrates a system for transesophageal echocardiography in accordance with the present invention.
Figure 12B:
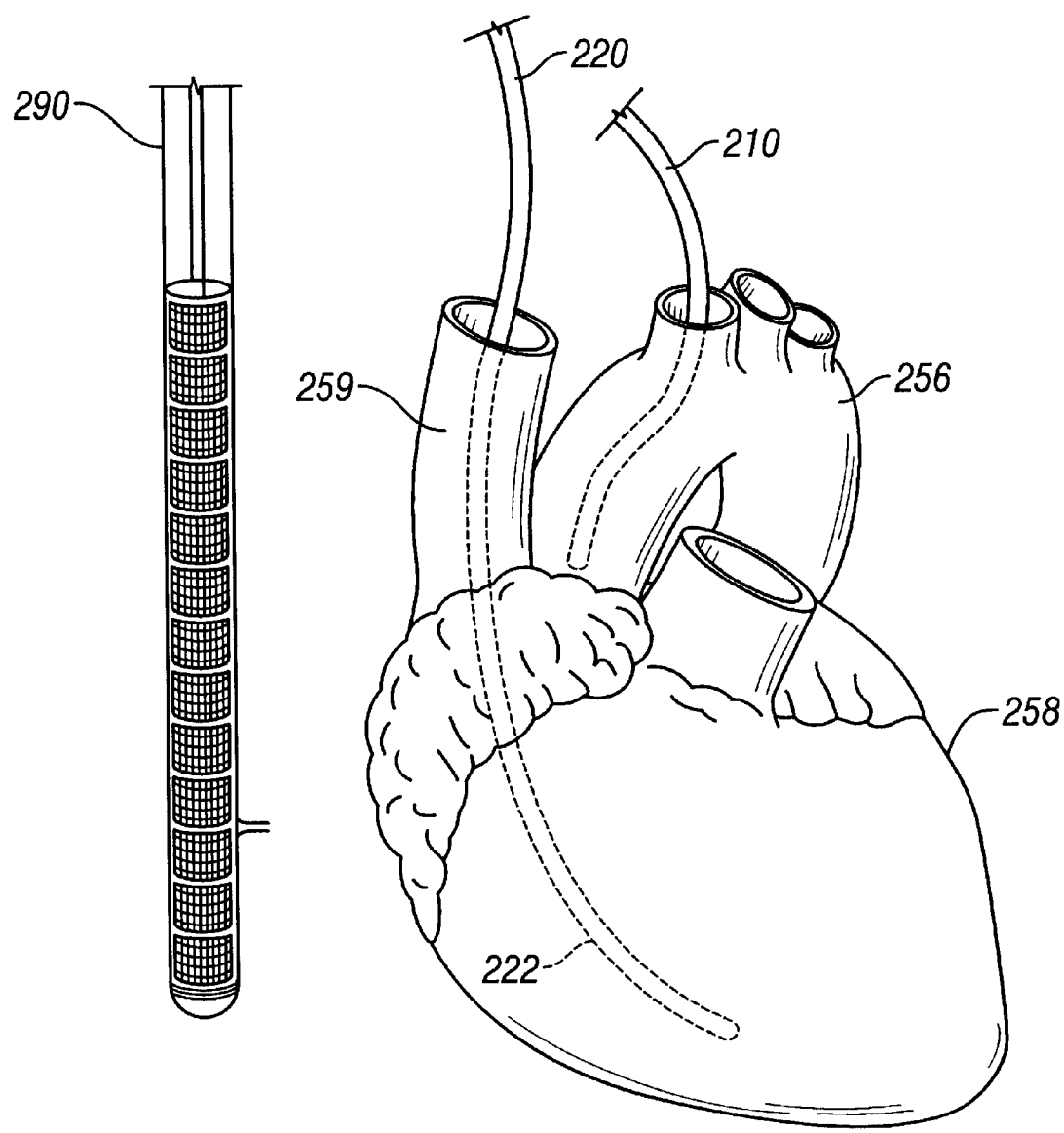
FIG. 12B is a detailed view of the heart of FIG. 12A showing a distal end of an endoscopic device in position near the heart.

FIGS. 12A and 12B schematically illustrate application of the disclosed systems and methods to a conventional TEE procedure.

The patient is first catheterized for the procedure using similar catheterization techniques as to those described herein. A drug delivery catheter 210 such as described herein is inserted into the patient's vasculature system from a peripheral access point such as a femoral or iliac artery 250, 252 in the leg, a brachial or radial artery 264 in the arm (as shown in FIG. 12A), or a carotid or subclavian artery 267 near the neck, and guided with the aid of fluoroscopy or echocardiography into place in the right (or left) coronary artery, preferably proximal to the AV node artery.

A transvenous pacing catheter 220 such as the Pacel™ TM catheter described herein is next introduced into the vasculature system of the patient via a suitable peripheral access point such as via the basilic vein in the arm 266 and the superior vena cava 259 and positioned in the right ventricle 260 of the heart. The transvenous pacing catheter 220 may also be introduced into the right ventricle 260 (and/or right atrium) from other peripheral access points such as via the jugular vein 257 in the neck (as shown in FIG. 12A) or the femoral or iliac vein 251, 253 in the leg by a direct cut-down or percutaneous insertion technique. It also should be understood that endocardial or epicardial pacing systems may be used.

A TEE probe, such as indicated with the reference numeral 290 in FIGS. 12A and B, is passed through the patient's mouth into the esophagus 292 and oriented towards the heart 258 to direct ultrasonic energy towards the heart (FIG. 12B). The specific construction of the probe is well described in the medical and patent literature and is well within the ability of one of ordinary skill in the art.

The next step in the procedure is to induce at least a brief period of reversible ventricular asystole of the heart for a sufficient time period to facilitate accurate and reliable imaging of the anatomical structure to be viewed, such as the heart, for example. It should be understood, however, that reversible ventricular asystole may be induced prior to placing the TEE probe in the patient's esophagus as well. As noted herein, any approved pharmaceutical agent(s) which is capable of inducing at least a brief period of cardiac asystole from several seconds to several minutes may then be used with the method. In one embodiment, the method can include providing a period of asystole which has a duration of about 1 to 30 minutes, for example about 3 to 20 minutes. In one embodiment, the period of asystole is induced by administering an AV node blocker and a β-blocker to the heart at a sufficient dosage amount of each to induce asystole in the heart. The AV node blocker in one embodiment may comprise a cholinergic receptor agonist, such as carbachol, although other AV node blockers and other ways of inducing third degree block of the AV node (such as electrical, ultrasonic, or cryonic stimulation of the AV node) are also contemplated by the present invention as disclosed in more detail herein. The β-blocker in one embodiment comprises propranolol, although other β-blockers may also be used. Preferably, a combination of an AV node blocker (and/or other AV node blocking techniques such as electrical, ultrasonic or cryogenic stimulation of the AV node) and one or more of the β-blockers described herein may then be used to induce at least a brief period of reversible ventricular asystole.

The procedure may include electrically pacing the heart with an electrical pacing system coupled to catheter 220, thereby to maintain the patient's blood circulation, and selectively intermittently stopping the electrical pacing at least once during the procedure to allow one or more intermittent periods of asystole of the heart, each of the one or more intermittent periods of asystole having a duration of from about 1 to 30 seconds, for example about 5 to 30 seconds, enabling precise ultrasonic real time visual image acquisition using the TEE probe 290.

In one embodiment of the method, the pharmaceutical compounds are serially delivered to the heart, and the β-blocker is administered prior to the AV node blocker. The β-blocker may also be delivered simultaneously with or following the administration of the AV node blocker. The β-blocker preferably is administered in an amount sufficient to substantially reduce the amount of AV node blocker required to induce asystole of the heart.

The method can include delivering the AV node blocker and the β blocker to the right or left coronary artery of the heart, e.g., proximal to the AV node artery. The AV node blocker and β-blocker may be administered to the right or left coronary artery through drug delivery catheter 210 which has at least one discharge opening which is positioned in the right or left coronary artery. The at least one discharge opening (not shown) of drug delivery catheter 210 is preferably positioned within about 8 cm from the AV node artery, for example about 1 to 3 cm proximal to the AV node artery, to minimize drug dilution to collateral vessels.

In one embodiment, the procedure described above comprises the intracoronary administration of the β-blocker propranolol to the coronary artery as one or more bolus infusions (at about 1 to 3 mg per bolus) at a total dosage amount of about 1 to 8 mg, for example about 1 to 6 mg, for example about 1 to 4 mg, for example about 2 to 3 mg. The procedure also comprises the serial intracoronary administration of the AV node blocker carbachol to the coronary artery as one or more initial bolus infusions (e.g., about two to three bolus infusions) at a total dosage amount of about 0.001 to 1.0 mg per bolus, for example about 0.05 to 0.5 mg per bolus, for example about 0.025 to 0.30 mg per bolus. This should be sufficient to induce a period of asystole with a duration of about 1 to 30 minutes, for example about 3 to 20 minutes, which should be sufficient time for accurate and reliable image acquisition using the TEE probe 290. If necessary, the procedure may include repeating the above drug dosing regimen one or more times during the procedure to induce a sufficient period of controlled and stable asystole to complete the procedure. For example, one or more repeat bolus doses of about 1 to 3 mg of propranolol and about 0.025 to 0.5 mg of carbachol per bolus can be given to the patient to maintain consistent and reliable arrest, as necessary.

Alternatively, if necessary, the method may further comprise maintaining the period of asystole for a longer duration by administering a continuous intracoronary infusion of carbachol to the heart of the patient at a rate of about 0.001 to 0.3 mg/min, for example about 0.005 to 0.3 mg/min, for example about 0.005 to 0.1 mg/min, over a period of about 5 to 90 minutes, for example, as appropriate.

Occlusion of Blood Vessels in the Brain and Other Organs of the Body

The compositions, apparatus, systems and methods for heart rate and rhythm control management described herein can further be used in the treatment of various diseases and conditions of the circulatory system and other organs of the body that are beneficially treated by the occlusion of blood vessels. Examples of the numerous diseases that can be treated by blocking associated blood vessels using, for example, intravascular coils, and whose treatment would benefit from elimination of movements caused by pulsatile blood flow include arteriovenous (AV) fistulas, AV malformations, aneurysms and pseudoaneurysms, patent ductus arteriosus, gastrointestinal bleeding, renal and pelvic bleeding, and tumors.

Placement of various substances (e.g., a liquid adhesive such as isobutylcyanoacrylate (IBCA)) within the blood vessels is one of the methods of encouraging the formation of thrombus (clot) which leads to the complete occlusion of the vessels. Occlusive coils have also been used to occlude blood vessels. The purpose of the coil is to encourage quick formation of a thrombus around the coil.

Of the many diseases that may be treated with embolic coils, cerebral aneurysms are of particular interest. Ruptured and unruptured cerebral aneurysms may in some cases be treated by a surgical approach in which the aneurysm is visualized directly and then surgically clipped thereby blocking blood flow into the aneurysm. Once the aneurysm is eliminated from the blood flow the risk of hemorrhage is eliminated. Another less invasive approach to the treatment of cerebral aneurysms is an endovascular approach, in which a catheter is introduced into the cerebral vascular system from a peripheral access point, such as a femoral artery, to access the aneurysm internally. The catheters can be used to deliver embolic devices, such as a balloon or a coil, to the site of the aneurysm to block blood flow into the aneurysm.

Although the present methods are discussed in relation to its use in the treatment of cerebral aneurysms, it is to be appreciated that the systems and methods of the present invention may be used in connection with a variety of other embolotherapy procedures in various blood vessels and organs of the body where an embolic device, such as a coil or embolic material, may be deployed.

Figure 13:
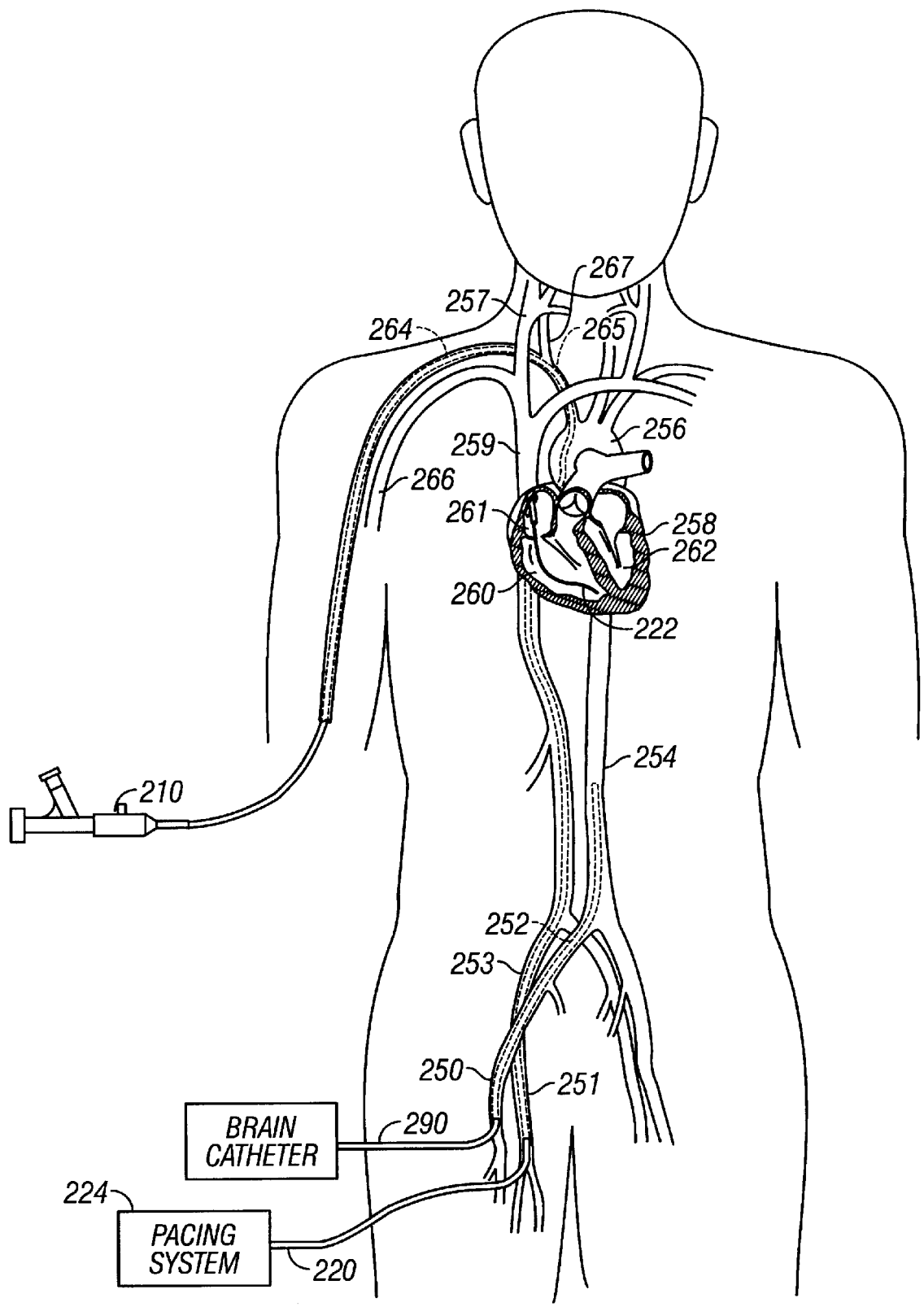
FIG. 13 illustrates a system for neurovascular aneurysm treatment in accordance with the invention.
Figure 14:
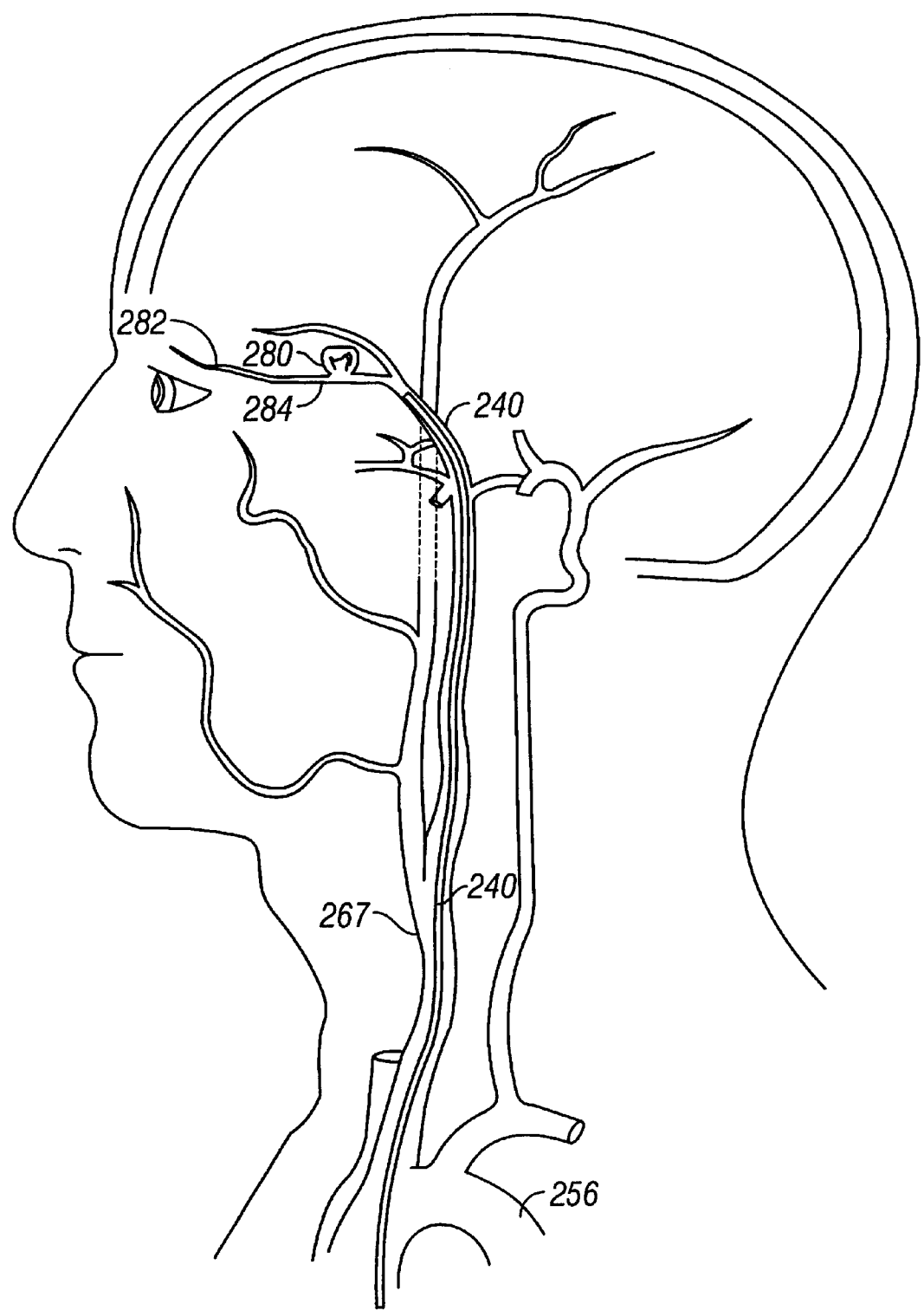
FIG. 14 is a detailed view of a patient's head showing advancement of the neurovascular delivery catheter of FIG. 13 to the site of an aneurysm in the brain.

For example, the systems and methods disclosed can be used to facilitate the accurate deployment of embolic devices and/or materials within the cerebral vasculature system of a patient, such as at the site of an aneurysm, as schematically illustrated in FIGS. 13 and 14. The systems and methods disclosed help to eliminate the movements caused by pulsatile blood flow at the vascular site, thereby making embolic device or material implantation more precise and controllable.

In this approach, the interior of the aneurysm is entered by the use of a catheter such as those shown in U.S. Pat. Nos. 4,739,768 and 4,884,575, the disclosures are of which are incorporated by reference herein. These procedures use catheters introduced into the cerebral vascular system from a peripheral access point, e.g. a femoral artery, to access the aneurysm internally. The catheters can be used to deliver embolic occlusive devices, such as balloons or coils, to the site of the aneurysm to block blood flow into the aneurysm. An example of a system for delivering a coil to a vasculature site is found in Guglielmi et al. U.S. Pat. No. 5,122,136, the disclosure of which is incorporated by reference herein. The embolic device, such as a coil, may be detached from the endovascular delivery catheter in a variety of ways, such as by an electrolytic process as described in U.S. Pat. No. 5,122,136, by mechanically detaching it from the delivery device such as shown in U.S. Pat. No. 5,354,295, both of which are hereby incorporated by reference herein, or by other detachment means.

In one embodiment, the patient is first catheterized for the procedure using similar catheterization techniques as those described herein. For example, a drug delivery catheter 210 and guidewire such as described herein is inserted into the patient's vasculature system from a peripheral access point such as a femoral or iliac artery 250, 252 in the leg (as shown), a brachial or radial artery 264 in the arm, or a carotid or subclavian artery 267 near the neck, and guided with the aid of fluoroscopy or echocardiography into place in the right coronary artery, preferably proximal to the AV node artery. The at least one discharge opening (not shown) of drug delivery catheter 210 is preferably positioned within about 8 cm from the AV node artery, for example about 1 to 3 cm proximal to the AV node artery, to minimize drug dilution to collateral vessels.

A transvenous pacing catheter 220 such as the Pacel™ catheter described herein is next introduced into the vasculature system of the patient via a suitable peripheral access point such as via the basilic vein 266 in the arm and the superior vena cava 259 and positioned in the right ventricle 260 of the heart 258. The transvenous pacing catheter 220 may also be introduced into the right ventricle 260 from other peripheral access points such as via the jugular vein in the neck or the femoral or iliac vein 251, 253 in the leg. It also should be understood that endocardial or epicardial pacing systems may be used.

With the patient fully catheterized as described above, the next step in the procedure is to introduce the embolic delivery catheter 240 into a blood vessel in the brain having an aneurysm or other disease condition therein. The diseased site may be an aneurysm 280 as shown in FIG. 14, or a fistula, AV malformation, or other disease distal to the site of deployment. To accomplish this, FIGS. 13 and 14 show one exemplary use in which the embolic device, in this case a coil 284, is placed via the delivery catheter 240 into the aneurysm 280 within the artery, in this case the opthalmic artery 282. The catheter 240 is typically introduced into the cerebral vasculature system of the patient from a peripheral access point such as a femoral artery 250 and guided with the aid of fluoroscopy to the brain through the aorta 256 and through one of the carotid (or vertebral) arteries 267 in the neck.

Once the insertion catheter 240 and the embolic coil are threaded through the vasculature system to the site of the aneurysm 280 in the brain, the next step in the procedure is to induce at least a brief period of reversible ventricular asystole of the heart for a sufficient time period to facilitate accurate and reliable placement of the coil into the aneurysm. It should be understood, however, that reversible ventricular asystole may be induced prior to placing the insertion catheter at the operative site as well. As noted herein, any approved pharmaceutical agent(s) which is capable of inducing at least a brief period of cardiac asystole from several seconds to several minutes may then be used with the method. In one embodiment, the period of asystole is induced by administering an AV node blocker and a β-blocker to the heart at a sufficient dosage amount of each to induce asystole in the heart. The AV node blocker in one embodiment may comprise a cholinergic receptor agonist, such as carbachol, although other AV node blockers and other ways of inducing third degree block of the AV node (such as electrical, ultrasonic, or cryonic stimulation of the AV node) are also contemplated by the present invention as disclosed in more detail hereinafter. The β-blocker in one embodiment comprises propranolol, although other β-blockers may also be used. Preferably, a combination of an AV node blocker (and/or other AV node blocking techniques such as electrical or ultrasonic stimulation of the AV node) and one or more of the herein described β-blockers may then be used to induce at least a brief period of reversible ventricular asystole. For example, similar to the previous embodiments, the procedure can include providing a period of asystole which has a duration of about 1 to 30 minutes, for example about 3 to 20 minutes.

In one embodiment of the method, the pharmaceutical compounds are serially delivered to the heart, and the β-blocker is administered prior to the AV node blocker. The β-blocker may also be delivered simultaneously with or following the administration of the AV node blocker. The β-blocker preferably is administered in an amount sufficient to substantially reduce the amount of AV node blocker required to induce asystole of the heart.

The method can include delivering the AV node blocker and the β blocker to the right or left coronary artery of the heart, e.g., proximal to the AV node artery. The AV node blocker and β-blocker may be administered to the right or left coronary artery through a drug delivery catheter which has at least one discharge opening which is positioned in the right or left coronary artery.

In one embodiment, the method described above comprises the intracoronary administration of the β-blocker propranolol to the coronary artery as one or more bolus infusions (at about 1 to 3 mg per bolus) at a total dosage amount of about 1 to 8 mg, for example about 1 to 6 mg, for example about 1 to 4 mg, for example about 2 to 3 mg. The method also comprises the serial intracoronary administration of the AV node blocker carbachol to the coronary artery as one or more initial bolus infusions (e.g., about two to three bolus infusions) at a total dosage amount of about 0.001 to 1.0 mg per bolus, for example about 0.05 to 0.5 mg per bolus, for example about 0.025 to 0.30 mg per bolus. This should be sufficient to induce a period of asystole with a duration of about 1 to 30 minute, for example about 3 to 20 minutes, which should be sufficient time for accurate and reliable placement of the embolic material or device within the blood vessel to occlude it. If necessary, the method may include repeating the above drug dosing regimen one or more times during the procedure to induce a sufficient period of controlled and stable asystole to complete the procedure. For example, one or more repeat bolus doses of about 1 to 3 mg of propranolol and about 0.025 to 0.5 mg of carbachol per bolus can be given to the patient to maintain consistent and reliable arrest, as necessary.

Alternatively, if necessary, the method may further comprise maintaining the period of asystole for a longer duration by administering a continuous intracoronary infusion of carbachol to the heart of the patient at a rate of about 0.001 to 0.3 mg/min, for example about 0.005 to 0.3 mg/min, for example about 0.005 to 0.1 mg/min, over a period of about 5 to 90 minutes, for example, as appropriate.

The method may include electrically pacing the heart with an electrical pacing system 224, thereby to maintain the patient's blood circulation, and selectively intermittently stopping the electrical pacing at least once during the procedure to allow one or more intermittent periods of asystole of the heart, each of the one or more intermittent periods of asystole having a duration of from about 1 to 30 seconds, for example about 1 to 15 seconds, enabling precise embolic device deployment. Alternatively, if the entire deployment process lasts for only about 1 minute or less, the patient can be immediately returned to normal sinus rhythm by administering atropine (e.g., about 1 mg) to the patient, thereby not requiring cardiac pacing. Pacing, however, may also be used to assist in recovering the heart and returning it to its normal sinus rhythm.

Thus, transient ventricular asystole induced by the techniques disclosed is a simple and safe technique that facilitates accurate occlusion of a blood vessel during an embolotherapy procedure. Aneurysms, fistulas, AV malformations, and tumors occurring in the brain, in the intracranial portion of the carotid arteries, vertebral arteries (and the portion of those arteries distal to the siphons) and basilar artery, in the circle of Willis, or even deeper in the brain and elsewhere may be treated by the techniques described above.

The methods disclosed may be used to facilitate endovascular insertion of an embolic device to a treatment site, or may be used to facilitate surgical interventions as well, such as the surgical placement of a metal clip at the site of an aneurysm under direct visualization. The techniques disclosed may also be used to facilitate placement of embolic devices and/or materials in other blood vessels of a patient's circulatory system as well as within other body organs.

Other Exemplary Procedures Which May be Advantageously Performed in Conjunction With the Methods of the Present Invention The compositions, apparatus, systems and methods for heart rate and rhythm control management described herein may also be used to facilitate a variety of other medical and surgical procedures that would benefit from a transiently arrested heart and/or a transient interruption of pulsatile blood flow. For example, the present methods are ideally suited to complement new emerging robotically-assisted surgical procedures such as those pioneered by Intuitive Surgical, Inc. (Mountain View, California) and described, for example, in U.S. Pat. Nos. 5,792,135, 5,797,900 and 5,807,377, the disclosures of which are incorporated by reference herein. As described in those patents, the Intuitive™ System generally consists of two main components: a surgeon's viewing and control console and a surgical arm unit that positions and maneuvers detachable surgical instruments. These straw-sized instruments include computer-enhanced mechanical wrists that are designed to provide the flexibility of the surgeon's wrist at the operative site through tiny ports in the chest wall. Using the Intuitive™ system, for example, surgeons will be able to perform procedures seated at the console, while viewing a high resolution 3D image of the surgical field. The surgeon's hands hold instruments that provide the flexibility of those used in open surgery. The surgeon's hand movements are transferred from the console to precise movements of the instruments at the operative site. The disclosed methods can beneficially provide a stable surgical field on the heart on which to operate using such advanced robotically controlled surgical instruments.

The techniques disclosed may also complement emerging transvacular approaches to bypass surgery such as those pioneered by Transvascular, Inc. (Menlo Park, Calif.) and described, for example, in U.S. Pat. No. 5,830,222, the entire contents of which is incorporated by reference herein. As described in that patent, methods and apparatus are provided for utilizing the vascular system as a conduit to reach other vascular and extravascular locations within the body. A method of coronary revascularization is provided wherein extravascular passageways are created to permit blood flow around a stenosed region in a coronary vessel and between vascular or non-vascular intracorporeal locations. The systems and methods disclosed herein can provide a convenient minimally invasive mechanism to eliminate movements caused by pulsatile blood flow and thus can facilitate the formation, modification, valving, maintaining, or closing of the disclosed extravascular passageways.

The methods disclosed may also be used in operations where uncontrolled hemorrhage is present including iatrogenic or traumatic injuries to bodily organs. For example, the techniques disclosed can be used in emergency trauma situations where the patient may be faced with the extreme risk of excessive blood loss from a severely damaged or ruptured internal organ. In such trauma cases, where there may not be sufficient time to cannulate the coronary vasculature system with a drug delivery catheter and/or a pacing catheter, the pharmaceutical agent(s) described herein can be immediately injected into the right (or left) coronary artery, aorta, AV node artery, or other blood vessel by direct injection using a syringe and needle assembly, for example, following proper surgical exposure of these vessels. The immediately induced asystole will stem the rapid loss of blood from the patient and provide the trauma personnel with adequate time to stabilize the patient for emergency surgery or other appropriate relief. The transiently induced cardiac arrest could then be reversed immediately following stabilization of the patient to restore the patient's heart to normal sinus rhythm and recirculate the blood through the patient's circulatory system, by delivering atropine to the patient by injection or otherwise. Pacing may not be required in such emergency instances. Pacing, however, may be used in certain situations to help restore the heart to normal sinus rhythm.

The systems and methods disclosed herein may also be used to control excessive bleeding associated with brain tumor surgery, in controlling bleeding associated with tumors that are apt to bleed a lot, such as prostatic tumors, and in procedures where blood conservation is important, such as procedures performed on, for example, Jehovah's Witnesses.

While the above list is representative of a wide variety of diagnostic and therapeutic procedures which can be performed in conjunction with the methods disclosed herein, it is not intended to be exhaustive and any other procedures which may be performed with the methods disclosed herein and which would benefit from a transiently arrested heart and/or transient interruptions in pulsatile blood flow will be apparent to those skilled in the art.

In addition, novel systems are disclosed for inducing transient arrest of the heart which can be used in conjunction with the above-described medical procedures. In one embodiment, a system for performing a medical or surgical procedure on a patient is provided which generally comprises a drug delivery device, a transvenous pacing catheter, and at least one endoscopic instrument which is capable of performing a surgical, diagnostic, or therapeutic interventional procedure within a vessel or bodily organ within the patient's body. The system may also comprise at least one guide catheter to facilitate positioning of the drug delivery device and/or pacing catheter into the patient's coronary vasculature system. The drug delivery device preferably has a sufficient length and flexibility to allow transluminal positioning of the device into a right or left coronary artery of the heart of the patient from a peripheral access vessel, such as a femoral or iliac artery in the leg, a brachial or radial artery in the arm, or a carotid or subclavian artery in the neck area of the patient. The transvenous pacing catheter preferably has a sufficient length and flexibility to allow transluminal positioning of the catheter into a right (or left) ventricle of the heart of the patient from a peripheral access vessel, such as a median basilic vein in the arm, a femoral or iliac vein in the leg, or a jugular or subclavian vein in the neck area of the patient.

The endoscopic instument may include a lasing apparatus coupled to an energy source, such as a laser energy source, for performing a transmyocardial revascularization procedure on the heart. The endoscopic instrument may also comprise an endoscopic viewing device such as a transesophageal echocardiographic probe. The endoscopic instrument may comprise an endograft aortic prosthesis delivery catheter, a neurovascular coil delivery catheter, an electrophysiologic mapping catheter, an endoscopic ablation catheter, a stent delivery catheter, an angioplasty catheter, or any other catheter which is capable of performing a wide variety of interventional surgical, therapeutic or diagnostic procedures within a body of a patient.

The above-described system may further comprise at least a first container comprising a dosage amount of an AV node blocker. The AV node blocker may comprise, for example, a cholinergic receptor agonist such as, for example, carbachol.

The system may further comprise a second container comprising a β-blocker such as, for example, propranolol.

The system may comprise an electrical pacing system operatively coupled to the transvenous pacing catheter. The electrical pacing system may comprise an extracorporeal pacer, a switch remotely coupled to the pacer, and an actuator arranged remote from the pacer and coupled to the switch. The actuator may comprise, for example, a foot pedal.

All publications and patent documents referred to herein are incorporated herein by reference in their entirety. The invention will now be described in more detail by reference to the following non-limiting examples.

EXAMPLES

Example 1

In Vivo Studies

The following comparative in vivo studies demonstrated the synergistic effect of the use of the cholinergic agent carbachol in combination with the β-blocker propranolol in stimulating ventricular asystole according to the present invention.

Eleven male crossbred swine weighing 20–25 kg were studied, eight of which received carbachol alone and three of which received carbachol plus propranolol. The swine were sedated using 10 mg/kg IV ketamine. After 20 minutes, the animals were induced with 10 mg/kg IV thiopental sodium and orotracheally intubated. The proper anesthetic plane was maintained with 1% Isoflurane. Periodic arterial blood gas samples were obtained to guide ventilator management. The electrocardiograph was continuously monitored. Through a 7 Fr sheath in the left femoral artery, arterial blood samples were obtained and a micromanometer was inserted to monitor central aortic blood pressure (Millar Instruments, Inc., Houston, Tex.). The heart was exposed through a median sternotomy and suspended in a pericardial cradle. Two temporary epicardial pacing wires were affixed to the right ventricle and connected to an external pacemaker (Medtronic, Inc., Minneapolis, Minn.). The pacemaker was modified to permit deactuation by means of depressing a foot pedal. Through the femoral sheath, an AR-1 guide (Cordis Corp., Miami Lakes, Fla.) was placed into the right coronary artery. An 0.014-inch floppy guide wire was then advanced into the right coronary artery to the level of the posterior descending coronary artery. The AR-1 guide was removed and a 2.5 Fr Tracker (Cordis Corp., Miami Lakes, Fla.) catheter was inserted over the guide wire. Using dye injection, the catheter was positioned just proximal to the take-off of the atrioventricular node artery. Carbachol (Sigma St. Louis, Mo.) solution was prepared the day of the experiment and infused at a constant rate using a Harvard pump.

Animals received either carbachol alone or carbachol in combination with propranolol (Inderal®, Wyeth Ayerst, Philadelphia, Pa.). All animals were instrumented and allowed 10 minutes of hemodynamic stability. Before carbachol was administered, each subject received a 500 ml IV bolus of 0.9% sodium chloride. In the animals receiving carbachol alone, carbachol was continuously infused through the Tracker catheter at increasing doses of 0.44, 0.62, 0.88, and 1.72 mg/min, until ventricular asystole was observed.

In the animals receiving carbachol plus propranolol, a 1 mg dose of propranolol (0.04–0.05 mg/kg) was administered through the Tracker catheter. Carbachol was then administered as a 0.5 mg intracoronary bolus (0.02 mg/kg) followed by a constant infusion. The infusion rate necessary to achieve ventricular asystole was 0.03 mg/min (1 to 1.2 μg/kg/min). After carbachol-mediated ventricular asystole was observed, the heart was paced at 100 beats/minute. At 60-second intervals, the pacemaker was turned off for five seconds to determine the underlying cardiac rate and rhythm. The systolic blood pressure (SBP), diastolic blood pressure (DBP), and main arterial pressure (MAP) were recorded every five minutes. The duration of ventricular asystole, defined in this example as a heart rate less than twelve beats per minute, was recorded. Profound hypotension (SBP<60 mmHg) after the administration of carbachol was treated with normal saline, intravenous bolus injections of phenylephrine (0.02 mg/kg), or both. After 75 minutes, the carbachol infusion was stopped and the time required to return to normal sinus rhythm was recorded. The results are set forth in Table 1 below.

TABLE 1

| animal | weight (kg) | infusion rate of carbachol (mg/min) | carbachol dose (μg/kg/min) | duration of ventricular asystole (min) | time to NSR[1] (min) |
|---|---|---|---|---|---|
| CARBACHOL INTRACORONARY INFUSION ||||||
| 1 | 41 | 0.44 | 10.7 | 76 | |
| 2 | 41 | 0.44 | 10.7 | 75 | |
| 3 | 20 | 0.62 | 31.0 | 47 | |
| 4 | 20 | 1.72 | 86.0 | 87 | |
| 5 | 36 | 0.44 | 12.2 | 75 | 8 |
| 6 | 45 | 0.44 | 9.7 | 53 | |
| 7 | 21 | 0.44 | 20.9 | 24 | |
| 8 | 21 | 0.88 | 41.9 | 76 | 3 |
| CARBACHOL AND PROPRANOLOL INTRACORONARY INFUSION ||||||
| 1 | 25 | 0.03 | 1.2 | 75 | 5 |
| 2 | 27 | 0.03 | 1.1 | 75 | 7 |
| 3 | 26 | 0.03 | 1.2 | 63 | 15 |

[1]NSR = normal sinus rhythm. Blank entries indicate data not recorded.

Example 2

Treatment of Human Patients

Ten human patients were treated pursuant to an investigational new drug clinical trial following Institutional Review Board and FDA approval and informed consent.

Repair of a leaky distal anastomosis was performed on 9 human patients (designated Patients 101–109) with stable coronary artery disease (CAD) following open-chest coronary artery bypass graft (CABG) surgery. The study was conducted to assess the ability to induce pacemaker-dependent reversible ventricular asystole in patients on cardiopulmonary bypass (CPB) utilizing an aortic cross clamp undergoing an open-chest CABG procedure. Established institutional techniques for preparation and conduct of CABG were used. At the end of the surgical procedure, and after the aortic cross clamp was removed, the AV-node blocker carbachol and the β-blocker propranolol were serially administered to the patients to induce pacemaker-dependent ventricular asystole. In Patients 101–109, the propranolol and carbachol were used at the end of the CABG surgery only during repair of leaking distal vascular anastomoses, while the patients were still on cardiopulmonary bypass (CPB) subsequent to the removal of the aortic cross clamp. In the tenth patient (designated Patient 201), the carbachol and propranolol drugs and temporary pacing were used for the CABG procedure itself, and the aortic cross clamp was avoided.

The patients were selected based on the following key criteria. Patients were selected ranging between 18 and 70 years in age with a normal sinus rhythm with β-wave-R-wave interval not exceeding 0.16 sec. Men or women were selected who had a stable coronary artery disease and were undergoing elective CABG revascularization of distal target(s) in the left anterior descending (LAD) artery system, right coronary artery (RCA) and/or the left circumflex (LCX) artery. Patients were selected with right dominant coronary circulation or an expectation that their AV node was supplied by the RCA, and with the presence of at least two of the following angiographic criteria: (1) coronary arteries greater than 2 mm in diameter, (2) noncalcified coronary arteries, or (3) an LAD that was not intramyocardial.

Patients with any of the following conditions were intended to be excluded from the study: (1) significant left main coronary artery stenosis, (2) left dominant coronary circulation, (3) RCA with proximal chronic total occlusion or inability to pass drug infusion catheter past proximal RCA stenosis, (4) presence of any significant hemodynamic instability, including, but not limited to, unstable angina or active ischemia requiring maximal medical management, malignant ventricular arrhythmias currently requiring medical management or cardiogenic shock requiring blood pressure support, (5) presence of any significant condition that increases the risk of the CABG procedure or other study procedure, including but not limited to, a history of peripheral vascular disease, hypertensive heart disease, cardiomyopathy, New York Health Association (NYHA) Class 3 or 4 congestive heart failure, chronic renal insufficiency or failure, prior CABG, valvular heart disease, unusual body habitus (e.g., morbid obesity), presence of acute pulmonary infection/pneumonia, metastatic cancer, thyrotoxicosis, sepsis, history of stroke or transient ischemic attack (TIA) or asymptomatic carotid bruit, (6) recent (within 2 weeks) acute myocardial infarction, (7) documented cardiac ejection fraction <30% within 30 days of planned procedure, (8) presence of any significant condition that would make the determination of the efficacy and/or safety endpoints of the study more difficult, including, but not limited to, first or second degree heart block, left or right bundle branch block or other IVCD, (9) presence of any significant condition that increases the risk of exposure to any of the components of the drugs as follows: Propranolol—This includes, but is not limited to, significant asthma, obstructive lung disease, congestive heart failure, hypersensitivity to propranolol or other β-adrenergic antagonists; Carbachol—This includes, but is not limited to, asthma, obstructive lung disease, epilepsy, Parkinsonism, peptic ulcer disease, hepatic insufficiency, hypersensitivity to carbachol or other cholinergic agonists (i.e., cholinomimetics or acetyl-cholinesterase inhibitors), (10) presence of any significant condition that increases the risk of use of a temporary pacemaker. This includes, but is not limited to, implanted permanent pacemaker, history of ventricular tachycardia or fibrillation requiring current antiarrhythmic therapy, other arrhythmia or condition that increases the risk of cardiac pacing, e.g., Wolfe-Parkinson-White syndrome, and (11) pregnant or nursing women.

For Patients 101–109, CABG surgery was performed using well established traditional methods. Patients were placed on CPB, the aorta was cross-clamped and cardioplegic arrest was administered. After distal and (if applicable) proximal anastomoses were sutured, the cross-clamp was removed and (if necessary) the heart defibrillated with patients still on CPB. When a leak requiring repair was detected at the distal anastomotic site(s), epicardial pacemaker leads were sewn into place on the ventricles and, optionally, the right atrium, of the patients and the pacing thresholds determined and recorded. A temporary pacemaker was connected to the epicardial leads. The pacing voltage was set at 10 times the pacing threshold. The pacemaker was first placed in ventricular-ventricular inhibited (VVI) mode with a rate of 60±15 bpm and pacing ensued for 2 minutes. Hemodynamic acceptability of the VVI-paced rhythm was assessed. The pacemaker was then set in ventricular-atrial triggered (VAT) mode and pacing ensued for another 2 minutes. Hemodynamic acceptability of the VAT-paced rhythm was assessed.

During surgery and prior to administration of the drug protocol, fluoroscopy was used to position an appropriate catheter, e.g., a Tracker™ (Target Therapeutics, Freemont, Calif.) catheter with an appropriate guide wire, in the proximal right coronary artery. This catheter was used for intracoronary administration of the study drugs. If at any time during the procedure, catheter displacement was noted, repeat angiography was used to reposition the catheter. Adequate supplies of phenylephrine, other adrenergic agents and volume repletion fluids were available at the bedside during and following drug administration in the event of unexpected adverse events, to control blood pressure, and/or to protect against inadvertent overdose.

The propranolol solution used was an injectable solution of Inderal® (Wyeth-Ayerst, Philadelphia, Pa.). The initial propranolol dose was 1 mg of a 1 mg/mL solution. Carbachol was provided in a vial containing 6 mL of a 0.255% solution (mg/dL). Each vial contained 2.55 mg/ml of carbachol in 5 mM sodium citrate and was adjusted to pH=7.0 using citric acid. The carbachol infusion solution was prepared by adding 5 mL of this solution to 250 mL of sterile saline. After reconstitution, the resulting concentration of the carbachol solution was 0.005%, or 0.05 mg/mL. The initial dose of carbachol was 0.025 mg or 0.5 mL and the initial infusion rate was 0.025 mg/min or 0.5 mL/min of the 0.005% solution.

A loading dose of propranolol ranging between 1–6 mg first was given to patients over a period of 1–3 minutes. Carbachol was administered as an intracoronary low dose bolus and as an infusion. For Patients 101–108, the bolus dose of carbachol used to initiate reversible ventricular asystole was in the range of 0.05–0.225 mg and the sustained infusion of carbachol used to maintain ventricular asystole was in the range of 0.05–0.15 mg/min. In one of the patients studied, overdrive pacing was used in conjunction with the loading dose of carbachol to induce ventricular asystole. Once complete heart block was achieved with no ventricular escape beats, and a pacemaker-dependent rhythm established, for patients 101–108 the distal anastomosis(es) were repaired during brief (up to 5 seconds) interruptions of pacing.

For Patient 201, the drugs and temporary pacing were used for the CABG procedure itself. A loading dose of 4 mg propranolol and 0.15 mg of carbachol were administered via intracoronary delivery to Patient 201 to initiate reversible ventricular asystole. Subsequently, an infusion of carbachol at a rate of 0.1 mg/min was given via intracoronary delivery to the patient to maintain ventricular asytole for a period of about 45 minutes. During this arrest period, a left internal mammary artery and obtuse marginal graft procedure were performed by the surgeon using intermittent pacing interruptions to successfully place the distal graft anastamosis sutures on a substantially still rather than moving heart, producing the benefit of an improved technical result and avoidance of cross-clamping of the aorta.

A dose of phenylephrine ranging between about 0.24–0.80 mg was administered to Patients 101, 103, 105–109 and 201 to control hypotension. When a satisfactory technical result had been achieved, the drug infusion was stopped and atropine was administered to determine the reliability of pharmacologic reversal of complete heart block with the exception of Patient 201, who was allowed to return to normal sinus rhythm naturally, over less than 15 minutes. The dosage amount of atropine used to reverse arrest in Patients 101–108 was about 1.0 mg. At the close of the pharmacologic protocol, after resumption of normal A-V conduction, CPB was removed. Established procedures for closing of the chest were followed.

In one patient, Patient 109, no arrest was achieved, however retrospective review of the post-operative angiogram revealed that the patient was a left dominant patient, i.e., having the AV node fed from the left coronary artery rather than the right coronary artery, where the catheter was placed. Transesophageal echocardiography (TEE) revealed normal left and right ventricular function, i.e., with no reported global or regional wall motion abnormalities in each patient in which arrest was achieved.

The results are shown in Table 2 below.

TABLE 2

| Patient | Minutes of Arrest | Propranol total dose - mg | Carbachol bolus - total mg | Carbachol Infusion mg/min | Arrest | Hypotension-phenylephrine used |
|---|---|---|---|---|---|---|
| 101 | 7 | 3 | 0.15 | 0.10 | Yes | Yes |
| 102 | 13 | 1 | 0.05 | 0.05 | Yes | No |
| 103 | 10 | 2 | 0.075 | 0.05 | Yes | Yes |
| 104 | 4 | 3 | 0.225 | 0.1 | Yes | No |
| 105 | 8 | 2 | 0.075 | 0.075 | Yes | Yes |
| 106 | 12 | 3 | 0.1 | 0.075 | Yes | Yes |
| 107 | 5 | 4 | 0.125 | 0.15 | Yes | Yes |
| 108 | 2 | 3 | 0.2 | 0.1 | Yes | Yes |
| 109 |  | 6 | 0.5 | 0.125 | No | Yes |
| 201 | 45 | 4 | 0.15 | 0.1 | Yes | Yes |

Although the foregoing invention has been described in some detail by way of illustration and example for purposes of clarity and understanding, it will be apparent those skilled in the art that certain changes and modifications may be practiced. therefore, the description and examples should not be construed as limiting the scope the invention.

What is claimed is:

1. A method of performing an aortic aneurysm repair procedure in which a graft member is positioned within a region of a patient's aorta, comprising:
    positioning a graft member within a patient's aorta in a region of an aneurysm, and
    inducing, prior to or during positioning the graft member in the aorta in a region of an aneurysm, at least one period of reversible ventricular asystole, while maintaining the ability of the heart to be electrically paced, wherein the period of asystole has a duration of more than approximately one minute.

2. The method of claim 1 wherein the graft is positioned in the region of the aneurysm during the at least one period of reversible ventricular asystole.

3. The method of claim 1 wherein the period of asystole has a duration of about 3 to 20 minutes.

4. The method of claim 1 wherein the period of asystole is induced by administering an AV node blocker and a β-blocker to the heart at a sufficient dosage amount of each to induce asystole in the heart.

5. The method of claim 4 wherein the AV node blocker comprises a cholinergic receptor agonist.

6. The method of claim 5 wherein the cholinergic receptor agonist comprises carbachol.

7. The method of claim 6 wherein the β-blocker comprises propranolol.

8. The method of claim 4 further comprising electrically pacing the heart to maintain the patient's blood circulation.

9. The method of claim 8 further comprising selectively intermittently stopping the electrical pacing during the asystole at least once for about 1 to 30 seconds prior to or during positioning the graft member in the region of the aneurysm.

10. The method of claim 4 wherein the β-blocker is administered prior to the AV node blocker.

11. The method of claim 4 wherein the β-blocker is administered in an amount sufficient to substantially reduce the amount of AV node blocker required to induce asystole of the heart.

12. The method of claim 4 wherein the AV node blocker and the β blocker are administered to the right or left coronary artery of the heart.

13. The method of claim 12 wherein the AV node blocker and β-blocker are administered to the right or left coronary artery through a drug delivery catheter which has at least one discharge opening which is positioned in the right or left coronary artery.

14. The method of claim 13 wherein the discharge opening is positioned in the right coronary artery proximate to the AV node artery.

15. The method of claim 13 wherein the drug delivery catheter is percutaneously inserted into the right coronary artery from a peripheral vascular access point.

16. The method of claim 15 wherein the peripheral vascular access point is a brachial artery.

17. The method of claim 15 wherein the peripheral vascular access point is a femoral artery.

18. The method of claim 15 wherein the peripheral vascular access point is a carotid artery.

19. The method of claim 15 wherein the peripheral vascular access point is a radial artery.

20. The method of claim 7 wherein the propranolol is administered as one or more bolus infusions at a total dosage amount of about 1 to 8 mg.

21. The method of claim 7 wherein the carbachol is administered as one or more initial bolus infusions at a total dosage amount of about 0.001 to 1.0 mg per bolus.

22. The method of claim 21 further comprising maintaining the period of asystole by administering a continuous intracoronary infusion of carbachol to the heart of the patient at a rate of about 0.001 to 0.3 mg/min over a time period of about 5 to 90 minutes.

23. A method of performing transmyocardial revascularization, comprising:
 forming at least one blood flow channel in a wall of the heart of a patient, where the at least one blood flow channel has a fluid connection with a chamber of the heart, and
 inducing, prior to or during formation of the channel, at least one period of reversible ventricular asystole, while maintaining the ability of the heart to be electrically paced, wherein the period of asystole has a duration of more than approximately one minute, and wherein the at least one blood flow channel is formed during the period of asystole.

24. The method of claim 23 wherein the period of asystole has a duration of about 3 to 20 minutes.

25. The method of claim 23 wherein the period of asystole is induced by administering an AV node blocker and a β-blocker to the heart at a sufficient dosage amount of each to induce asystole in the heart.

26. The method of claim 25 wherein the AV node blocker comprises a cholinergic receptor agonist.

27. The method of claim 26 wherein the cholinergic receptor agonist comprises carbachol.

28. The method of claim 27 wherein the β-blocker comprises propranolol.

29. The method of claim 25 further comprising electrically pacing the heart to maintain the patient's blood circulation.

30. The method of claim 29 further comprising selectively intermittently stopping the electrical pacing during the asystole at least once for about 1 to 30 seconds prior to or during formation of the channel.

31. The method of claim 25 wherein the β-blocker is administered prior to the AV node blocker.

32. The method of claim 25 wherein the β-blocker is administered in an amount sufficient to substantially reduce the amount of AV node blocker required to induce asystole of the heart.

33. The method of claim 25 wherein the AV node blocker and the β blocker are administered to the right or left coronary artery of the heart.

34. The method of claim 33 wherein the AV node blocker and β-blocker are administered to the right or left coronary artery through a drug delivery catheter which has at least one discharge opening which is positioned in the right or left coronary artery.

35. The method of claim 34 wherein the discharge opening is positioned in the right coronary artery proximate to the AV node artery.

36. The method of claim 34 wherein the drug delivery catheter is percutaneously inserted into the right coronary artery from a peripheral vascular access point.

37. The method of claim 36 wherein the peripheral vascular access point is a brachial artery.

38. The method of claim 36 wherein the peripheral vascular access point is a femoral artery.

39. The method of claim 36 wherein the peripheral vascular access point is a carotid artery.

40. The method of claim 36 wherein the peripheral vascular access point is a radial artery.

41. The method of claim 28 wherein the propranolol is administered as one or more bolus infusions at a total dosage amount of about 1 to 8 mg.

42. The method of claim 28 wherein the carbachol is administered as one or more initial bolus infusions at a total dosage of about 0.001 to 1.0 mg per bolus.

43. The method of claim 42 further comprising maintaining the period of asystole by administering a continuous intracoronary infusion of carbachol to the heart of the patient at a rate of about 0.001 to 0.3 mg/min over a duration of about 5 to 90 minutes.

44. The method of claim 23 wherein the blood flow channel in the heart is formed by irradiating an exterior surface of the heart with laser energy.

45. The method of claim 23 wherein the blood flow channel in the heart is formed by irradiating an interior surface of the heart with laser energy.

* * * * *